United States Patent [19]

Gengenbach et al.

[11] Patent Number: 6,069,298
[45] Date of Patent: May 30, 2000

[54] METHODS AND AN ACETYL COA CARBOXYLASE GENE FOR CONFERRING HERBICIDE TOLERANCE AND AN ALTERATION IN OIL CONTENT OF PLANTS

[75] Inventors: Burle G. Gengenbach, St. Paul; David A. Somers, Roseville; Donald L. Wyse, Wyoming; John W. Gronwald, Shoreview; Margaret A. Egli, Roseville; Sheila M. Lutz, St. Paul, all of Minn.

[73] Assignees: Regents of the University of Minnesota, Minneapolis, Minn.; The United States of America, Washington, D.C.

[*] Notice: This patent is subject to a terminal disclaimer.

[21] Appl. No.: 08/417,089

[22] Filed: Apr. 5, 1995

Related U.S. Application Data

[63] Continuation-in-part of application No. 08/014,326, Feb. 5, 1993, Pat. No. 5,498,544.
[51] Int. Cl.[7] ........................... C12N 15/29; C12N 15/52; C12N 15/70; C12N 15/74; C12N 15/81; C12N 15/82
[52] U.S. Cl. ........................... 800/278; 435/468; 435/471; 435/483; 435/69.8; 435/455; 536/23.2; 536/23.6; 800/281; 800/300
[58] Field of Search ........................... 435/320.1, 172.3, 435/419, 468, 69.1, 243, 254.2, 257.2, 348, 471, 69.8, 483, 455; 536/23.2, 23.6; 800/205, DIG. 52, DIG. 56, 278, 281, 300

[56] References Cited

U.S. PATENT DOCUMENTS

| | | | |
|---|---|---|---|
| 4,326,358 | 4/1982 | Lawrence, Jr. et al. | 47/58 |
| 4,731,499 | 3/1988 | Puskaric et al. | 800/200 |
| 4,761,373 | 8/1988 | Anderson et al. | 435/172.3 |
| 4,874,421 | 10/1989 | Kleschick et al. | 71/94 |
| 4,940,835 | 7/1990 | Shah et al. | 800/205 |
| 5,107,065 | 4/1992 | Shewmaker et al. | 800/205 |
| 5,162,602 | 11/1992 | Somers et al. | 800/235 |
| 5,190,931 | 3/1993 | Inouye | 435/91 |
| 5,290,696 | 3/1994 | Somers et al. | 436/240.5 |
| 5,498,544 | 3/1996 | Gengenbach et al. | 435/320.1 |
| 5,510,474 | 4/1996 | Quail et al. | 536/24.1 |
| 5,539,092 | 7/1996 | Haselkorn et al. | 536/23.2 |
| 5,689,045 | 11/1997 | Logemann et al. | 800/205 |
| 5,854,420 | 12/1998 | Ashton et al. | 800/205 |

FOREIGN PATENT DOCUMENTS

| | | | |
|---|---|---|---|
| 0 270 356 A2 | 12/1987 | European Pat. Off. | C12N 15/00 |
| 0469810 | 2/1992 | European Pat. Off. | C07K 13/00 |
| 1 720 594 | 3/1992 | U.S.S.R. | A01H 1/02 |
| 89/07647 | 8/1989 | WIPO | C12N 15/00 |
| 93/11243 | 6/1993 | WIPO | C12N 15/52 |
| WO93/11243 | 6/1993 | WIPO | C12N 15/52 |
| 94/08016 | 4/1994 | WIPO | C12N 15/52 |
| 94/17188 | 8/1994 | WIPO | C12N 15/52 |
| 94/23027 | 10/1994 | WIPO | C12N 15/11 |
| 94/29467 | 12/1994 | WIPO | C12N 15/82 |
| 95/06128 | 3/1995 | WIPO | C12N 15/82 |
| 95/29246 | 11/1995 | WIPO | C12N 15/82 |

OTHER PUBLICATIONS

An, "Binary Ti Vectors for Plant Transformation and Promoter Analysis", *Methods in Enzymology*, 153:292 (1987).
Armstrong et al., "Establishment and Maintenance of Friable, Embryogenic Maize Callus and the Involvement of L–proline", *Planta*, 164:207 (1985).
Arnon, "Copper Enzymes in Isolated Chloroplasts. Polyphenoloxidase in beta–Vulgaris", *Plant Physiol.*, 24:1–15 (1949).
Bachmann, "Linkage Map of *Escherichia coli* K–12, Edition 7", *Microbiological Reviews*, 47:180–230 (1983).
Back et al., "Isolation of the Spinach Nitrate Reductase Gene Promoter Which Confers Nitrate Inducibility on GUS Gene Expression in Transgenic Tobacco", *Plant Molec. Biol.*, 17:9–18 (1991).
Berg et al., "The Prokaryotic Transposable Element Tn5", *Biotechnology*, 1:417–436 (1983).
Burton et al., "Inhibition of Plant Acetyl–Coenzyme a Carboxylase by the Herbicides Sethoxydim and Haloxyfop", *Biochem. Biophys. Res. Comm.*, 148:1039–1044 (Nov. 13, 1987).
Burton et al., "Inhibition of Corn Acetyl–CoA Carboxylase by Cyclohexanedione and Aryloxyphenoxypropionate Herbicides", *Pest. Biochem. Physiol.*, 34:76–85 (1989).
Cline et al., "Precursors to Two Nuclear–encoded Chloroplast Proteins Bind to the Outer Envelope Membrane before Being Imported into Chloroplasts", *J. Biol. Chem.*, 260:3691–3696 (1985).

(List continued on next page.)

*Primary Examiner*—David T. Fox
*Assistant Examiner*—Amy J. Nelson
*Attorney, Agent, or Firm*—Schwegman, Lundberg, Woessner & Kluth P.A.

[57] ABSTRACT

The present invention provides the complete cDNA sequence of maize acetyl CoA carboxylase and methods for conferring herbicide tolerance and/or altering the oil content of plants by introducing and expressing a plant acetyl CoA carboxylase gene in plant cells. The method of imparting herbicide tolerance to a plant includes the steps of introducing an expression cassette encoding a plant acetyl CoA carboxylase or an antisense DNA sequence complementary to the sequence for a plant acetyl CoA carboxylase gene operably linked to a promoter functional in plant cells, into the cells of a plant tissue and expressing the plant acetyl CoA carboxylase gene in an amount effective to render the acetyl CoA carboxylase and/or plant cell substantially tolerant to the herbicides. The method of altering the oil content in a plant includes the steps of introducing an expression cassette into plant cells and expressing the acetyl CoA carboxylase gene in an amount effective to alter the oil content of the cells. The expression cassette can also be introduced into other host cells to increase yield of a plant acetyl CoA carboxylase so that crystallized enzyme can be used to screen and identify other herbicides that bind to and inhibit the enzyme.

11 Claims, 21 Drawing Sheets

OTHER PUBLICATIONS

D'Hafluin et al., "Transgenic Maize Plants by Tissue Electroporation", *The Plant Cell*, 4:1495–1505 (1992).

Egli et al., "Biochemical and Genetic Characterization of Maize Acetyl–CoA Carboxylase", Maize Genetics Conference, Abstract (Mar. 19–22, 1992).

Fromm et al., "Inheritance and Expression of Chimeric Genes in the Progeny of Transgenic Maize Plants", *Bio/Technol.*, 8:833–839 (1990).

Gantt et al., "Molecular Cloning of a Pea H1 Histone cDNA", *Eur. J. Biochem.*, 166:119–125 (1987).

Gordon–Kamm et al., "Transformation of Maize Cells and Regeneration of Fertile Transgenic Plants", *The Plant Cell*, 2:603–618 (1990).

Green, "Prospects for Crop Improvement in the Field of Cell Culture", *Hort. Sci.*, 12, 7–10 (1977).

Hamilton et al., "Antisense Gene that Inhibits Synthesis of the Hormone Ethylene in Transgenic Plants", *Nature*, 346:284–287 (1990).

Hammarback et al., "Antibody Exchange Immunochemistry", *J. Biol. Chem.*, 265:12763 (1990).

Hoj et al., "Partial Separation of Individual Enzyme Activities of an ACP–Dependent Fatty Acid Synthetase from Barley Chloroplasts", *Carlsberg Res. Commun.*, 47:119–141 (1982).

Jefferson, "Assaying Chimeric Genes in Plants: The GUS Gene Fusion System", *Plant Molec. Biol. Reporter*, 5:387–405 (1987).

Keegstra et al., "Chloroplastic Precursors and their Transport Across the Envelope Membranes", *Ann. Rev. Plant. Physiol. Mol. Biol.*, 40:471–501 (1989).

Liedvogel et al., "Fatty–acid Synthesis in Chloroplasts from Mustard (*Sinapis alba* L.) Cotyledons: Formation of Acetyl Coenzyme A by Intraplastid Glycolytic Enzymes and a Pyruvate Dehydrogenase Complex", *Planta*, 169:481–489 (1986).

Mishina et al., "Yeast Mutants Defective in Acetyl–Coenzyme A Carboxylase and Biotin: Apocarboxyase Ligase", *Eur. J. Biochem.*, 111:79–87 (1980).

Mitra et al., "Three Distinct Regulatory Elements Comprise the Upstream Promoter Region of the Nopaline Synthase Gene", *Molec. Gen. Genetic.*, 215:294 (1989).

Nikolau et al., "Acetyl–Coenzyme A Carboxylase in Maize Leaves", *Arch. Biochem. Biophys.*, 211:605–612 (1981).

Ohlrogge et al., "Subcellular Localization of Acyl Carrier Protein in Leaf Protoplasts of *Spinacia oleracea*", *Proc. Natl. Acad. Sci. USA*, 76:1194–1198 (1979).

Parker et al., "Selection and Characterization of Sethoxydim–tolerant Maize Tissue Cultures", *Plant Physiol.*, 92:1220–1225 (1990).

Parker et al., "Dominant Mutations Causing Alterations in Acetyl–Coenzyme A Carboxylase Confer Tolerance to Cyclohexanedione and Aryloxyphenoxypropionate Herbicides in Maize", *Proc. Natl. Acad. Sci USA*, 87:7175–7179 (1990).

Post–Beittenmiller et al., "Regulation of Plant Fatty Acid Biosynthesis", *Plant Physiol.*, 100:923–930 (1992).

Smith et al., "Measurement of Protein Using Bicinchoninic Acid", *Anal. Biochem.*, 150:76–85 (1985).

Turnham et al., "Changes in the Activity of Acetyl–CoA Carboxylase During Rape–Seed Formation", *Biochem. J.*, 212:223–229 (1983).

Walters et al., "Transformation and Inheritance of a Hygromycin Phosphotransferase Gene in Maize Plants", *Plant Mol. Biol.*, 18:189–200 (1992).

Zhu et al., "Xylulose 1,5–Bisphosphate Synthesized by Ribulose 1,5–Bisphosphate Carboxylase/Oxygenase During Catalysis Binds to Decarbamylated Enzyme", *Plant Physiol.*, 97:1348–1353 (1991).

Anderson, et al., "Selection of an Imidazolinone Tolerant Mutant of Corn", Abstract, Sixth Int. Congress Plant Tissue Cell Culture, Minneapolis, MN, p. 437 (Aug., 1986).

Anderson, et al., "Cell Culture Selection of Herbicide Tolerant Corn", Abstract, ASA, Madison, WI, p. 56 (1985).

Botterman, et al., "Engineering Herbicide Resistance in Plants", *Trends in Genetics*, 4, 219–222 (1988).

Bowman, et al., "Selection for Resistance to Paraquat in Maize Embryogenic Cell Cultures", Abstract, Sixth Int. Congress Plant Tissue Cell Culture, Minneapolis, MN, p. 73 (Aug. 4–8, 1986).

Fawcett, et al., "Influence of Environment on Corn (*Zea mays*) Tolerance to Sethoxydim", *Weed Science*, 35, 568–575 (1987).

Green, et al., "Plant Regeneration in Tissue Cultures of Maize", In: *Maize for Biological Research*, Plant Molecular Biology Association, Charlottesville, VA, pp. 367–371 (1982).

Lamhonwah, et al., "Sequence Homology Around the Biotin–Binding Site of Human Propionyl–CoA Carboxylase and Pyruvate Carboxylase", *Archives Biochem. Biophys.*, 254, 631–636 (1987).

Meredith, et al., "Tolerance in cell culture", In: *Herbicide Resistance in Plants*, Lebarin et al., (eds). John Wiley and Sons, New York, pp. 275–291 (1982).

A. R. Ashton, et al., "Molecular cloning of two different cDNAs for maize acetyl CoA carboxylase", *Plant Molecular Biology*, 24, 35–49 (1994).

M. Egli, et al., "Identification and mapping of maize acetyl–CoA carboxylase genes", *Maize Genetics Cooperation Newsletter*, 68, 92–93 (Mar., 1994).

K. M. Elborough, et al., "Isolation of *Brassica napus* encoding the biotin–binding and transcarboxylase domains of acetyl–CoA carboxylase: assignment of the domain structure in a full–length *Arabidopsis thaliana* genomic clone.", *Biochemical J.*, 301, 599–605 (1994).

B. Gengenbach, et al., "Maize acetyl–coenzyme A carboxlyalse genes", *In: Plant Lipid Metabolism*, Kader, J.–C., et al., (eds.), Kluwer Academic Press, Boston, pp. 43–45 (1995).

P. Gornicki, et al., "Wheat acetyl–coenzyme A carboxylase: cDNA and protein structure", *Proc. Natl. Acad. Sci. USA*, 91, 6860–6864 (Jul., 1994).

S. Lutz, et al., "Characterization of two acetyl–CoA carboxylase genes from maize", *Abstract, International Congress of Plant Molecular Biology*, Section 8–5, Lipid Metabolism, Abstract No. 1460 (Jun., 1994).

S. Lutz, et al., "Intron sequence divergence in type A and C maize ACCase Genes", Abstract, 37th Annual Maize Genetics Conference, poster 34, (Mar., 1995).

K. R. Roesler, et al., "Structure and expression of an Arabidopsis acetyl–coenzyme A carboxylase gene", *Plant Physiology*, 105, 611–617 (1994).

W. Schulte, et al., "A gene encoding acetyl–coenzyme A carboxylase from *Brassica napus*", *Plant Physiology*, 106, 793–794 (1994).

B. S. Shorrosh, et al., "Molecular cloning, characterization, and elicitation of acetyl–CoA carboxylase from alfalfa", *Proc. Nat. Acad. Sci. USA*, 91, 4323–4327 (May, 1994).

K. L. Van Dee, "Evidence for Two Independently Segregating Loci Ecoding Acetyl–CoA Carboxylase in *Zea mays*," Master of Science Thesis, University of Minnesota (Oct., 1994).

M. A. Egli, et al., "A Maize Acetyl–Coenzyme A Carboxylase cDNA Sequence", *Plant Physiology*, 108, 1299–1300, (Jul. 1995).

M. A. Egli, et al., "A Maize Acetyl–CoA Carboxylase cDNA Maps to Chromosome 2S", *Supplement to Plant Pysiology*, 105, No. 1, p. 310, (May 1994).

Ashton et al (1994) Plant Molecular Biology vol. 24: pp. 35–49.

Bai et al., *J. Biol. Chem.*, 261, 12395–12399 (1986).

Klein et al., *Nature*, 327, 70 (1987).

Marshall et al., *Hygronomy Abstracts*, 170, Title Summary No. C7–51P, (May 1988).

Al–Feel, W., et al., "Cloning of the yeast FAS3 gene and Primary Structure of Yeast Acetyl–CoA Carboxylase," *Proc. Nat. Acad. Sci. USA*, 89, 4534–4538 (1992).

Bettey, M., et al., "Purification and characterization of Acetyl–CoA Carboxylase from Developing Pea Embryos," *J. Plant Physiol.*, 140, 513–520 (1992).

Charles, D. J., et al., "Characterization of Acetyl–CoA Carboxylase in the Seed of Two Soybean Genotypes," *Phytochem.*, 25, 55–59 (1986).

Charles, D. J., et al., "Purification and characterization of Acetyl–CoA Carboxylase from Developing Soybean Seeds," *Phytochem.*, 25, 1067–1071 (1986).

D'Halluin, K., et al., "Transgenic Maize Plants by Tissue Electroporation," *The Plant Cell*, 4, 1495–1505 (1992).

Egin–Buhler, B., et al., "Improved Purification and Further Characterization of Acetyl–CoA Carboxylase from Cultured Cells of Parsley (*Petroselinum hortense*)," *Eur. J. Biochem.*, 133, 335–339 (1983).

Egli, M. A., et al., "Characterization of Maize Acetyl–Coenzyme A Carboxylase," *Plant Physiol.*, 101, 499–506 (1993).

Egli, M., et al., Cloning and Sequence Analysis of a Maize Acetyl–CoA Carboxylase Gene, *Plant Physiol.*, 102S, 70 (1993).

Egli, M., et al., "Cloning and Expression of Maize Acetyl–CoA Carboxylase," Agronomy Abstracts, 1992 Annual Meeting, p. 189 (1992).

Egli, M., et al., "A 233–kD Subunit of Acetyl–CoA Carboxylase is Encoded by the Maize Acc–1 gene," *Maize Genetics Newsletter*, 66, 94 (1992).

Egli, M., et al., "Purification and Characterization of Maize Acetyl–CoA Carboxylase," *Plant Physiol.*, 96S, 92 (1991).

Egli, M., et al., "Purification of Maize Leaf Acetyl–CoA Carboxylase," *Maize Genetics Newsletter*, 65, 95 (1991).

Finlayson, S. A., et al., "Acetyl–Coenzyme A Carboxylase from the Developing Endosperm of *Ricinus communis,*" *Arch. Biochem. Biophys.*, 225, 576–585 (1983).

Gornicki, P., et al., "Genes for Two Subunits of Acetyl Coenzyme A Carboxylase of Anabaena sp. Strain PCC 7120: Biotin Carboxylase and Biotin Carboxylase Carrier Protein," *J. Bacteriol.*, 175, 5268–5272 (1993).

Gornicki, P., et al., "Wheat Acetyl–CoA Carboxylase," *Plant Mol. Biol.*, 22, 547–552 (1993).

Kannangara, C.G., et al., "Fat Metabolism in High Plants LIV. A Procaryotic Acetyl–CoA Carboxylase in Spinach Chloroplasts," *Arch. Biochem. Biophys.*, 152, 83–91 (1972).

Kondo, H., et al., "Acetyl–CoA Carboxylase from *Escherichia coli*: Gene Organization and Nucleotide Sequence of the Biotin Carboxylase Subunit," *Proc. Natl. Acad. Sci. USA*, 88, 9730–9733 (1991).

Laing, W. A., et al., "Activation of Spinach Chloroplast Acetyl–Coenzyme A Carboxylase by Coenzyme A," *FEBS Lett.*, 144, 341–344 (1982).

Li, S.–J., et al., "The Gene Encoding the Biotin Carboxylase Subunit of *Escherichia coli* Acetyl–CoA Carboxylase," *J. Biol. Chem.*, 267, 855–863 (Jan. 15, 1992).

Li, S.–J., et al., "The Genes Encoding the Two Carboxyltransferase Subunits of *Escherichia coli* Acetyl–CoA Carboxylase," *J. Biol. Chem.*, 267, 16841–16847 (Aug. 25, 1992).

Lopes–Casillas, F., et al., "Structure of the Coding Sequence and Primary Amino Acid Sequence of Acetyl–Coenzyme A Carboxylase" *Proc. Nat. Acad. Sci. USA*, 85, 5784–5788 (1988).

Nikolau, B. J., et al., "Purification and Characterization of Maize Leaf Acetyl–Coenzyme A Carboxylase," *Arch. Biochem. Biophys.*, 288, 85–96 (1984).

Parker, W. B., et al., "Dominant Mutations Causing Alterations in Acetyl–Coenzyme A Carboxylase Confer Tolerance to Cyclohexanedione and Aryloxyphenoxypropionate Herbicides in Maize," *Proc. Nat. Acad. Sci. USA*, 87, 7175–7179 (1990).

Roessler, P. G., et al., "Cloning and Characterization of the Gene that Encodes Acetyl–Coenzyme A Carboxylase in the Alga *Cyclotella cryptica,*" *J. Biol. Chem.*, 268, 19254–19259 (1993).

Sasaki, Y.,et al., "Chlorplast–Encoded Protein as a Subunit of Acetyl–CoA Carboxylase in Pea Plant," *J. Biol. Chem.*, 268, 25118–25123 (1993).

Slabas, A. R., et al., "Rapid Purification of a High Molecular Weight Subunit Polypeptide form of Rape Seed Acetyl–CoA Carboxylase," *Plant Sci.*, 39, 177–182 (1985).

Somers, D.A., "Expression of the Acc1 Gene–Encoded Acetyl–Coenzyme A Carboxylase in Developing Maize (*Zea mays* L.) Kernals," *Plant Physiol.*, 101, 1097–1101 (1993).

Takai, T., et al., "Primary Structure of Chicken Liver Acetyl–CoA Carboxylase Deduced from cDNA Sequence," *J. Biol. Chem.*, 263, 2651–2657 (1988).

von Heijne, G., et al., "Domain Structure of Mitochondrial and Chloroplast Targeting Peptides," *Eur. J. Biochem.*, 180, 535–545 (1989).

Egli, M.A., et al., "Characterization of Maize Acetyl–Coenzyme A Carboxylase", *Plant Physiology*, 101, 499–506, (1993).

Elborough, K.M., et al., "Studies on Wheat Acetyl CoA Carboxylase and the Cloning of a Partial cDNA", *Plant Molecular Biology*, 24, 21–34, (1994).

Roessler, P.G., "Expression of an Algal Acetyl–CoA Carboxylase Gene in E. Coli and Yeast", *Abstracts, 11th International Lipid Meeting*, Paris, France, (Jun. 1994).

Roessler, P.G., et al., "Expression of an Algal Acetyl–CoA Carboxylase Gene in E. coli", In: *Plant Lipid Metabolism*, Kader, J.–C., et al., (eds.), Kluwer Academic Publishers, The Netherlands, pp. 46–48, (Feb. 1995).

Caffrey, J.J., et al., "Genetic Mapping of Two Acetyl–CoA Carboxylase Genes", *Maize Genetics Cooperation Newsletter*, 69, 3–4 (1995).

Dimroth, P., et al., "Crystallization of Biotin Carboxylase, a Component Enzyme of the Acetyl–CoA Carboxylase System from *Escherichia coli*", *Hoope–Seyler's Z. Physiol. Chem.*, 352, 351–354 (Mar. 1971).

Egli, M.A., et al., "Biochemical and Genetic Characterization of Maize Acetyl–CoA Carboxylase", Abstracts, Maize Genetics Conference, Pacific Grove, CA (Mar. 19–22, 1992).

Egli, M.A., et al., "Identification and Mapping of Maize Acetyl–CoA Carboxylase Genes", *Maize Genetics Coorperation Newsletter*, 68, 92–93 (Mar. 15, 1994).

Elborough, K.M., et al., "Isolation of cDNAs from *Brassica napus* Encoding the Biotin–Binding and Transcarboxylase Domains of Acetyl–CoA Carboxylase: Assignment of the Domain Structure in a Full–Length *Arabidopsis thaliana* Genomic Clone", *Biochem. J.*, 301, 599–605 (1994).

Finlayson, S.A., et al., "Acetyl–Coenzyme A Carboxylase from the Developing Endosperm of *Ricinus communis*," *Archives of Biochemistry and Biophysics*, 225, 576–585 (Sep. 1983).

Gengenbach, B., et al., "Maize Acetyl–Coenzyme A Carboxylase Genes", *In: Plant Lipid Metabolism*, Kader, J.–C., et al., (eds.), Kluwer Academic Press, The Netherlands, pp. 43–45 (1995).

Gornicki, P., et al., "Wheat Acetyl–Coenzyme A Carboxylase: cDNA and Protein Structure", *Proc. Natl. Acad. Sci. USA*, 91, 6860–6864 (Jul. 1994).

Lutz, S., et al., "Characterization of Two Acetyl–CoA Carboxylase Genes from Maize", *Abstracts, International Congress of Plant Molecular Biology*, Amsterdam, The Netherlands (Jun. 1994).

Lutz, S., et al., "Characterization of Two Acetyl–CoA Carboxylase Genes from Maize", *Abstracts, International Meeting on Plant Lipids*, Paris, France, 1 p., (Jun. 1994).

Lutz, S., et al., "Genomic Mapping of Acetyl–CoA Carboxylase Clones and Herbicide Resistance in Maize", Proceedings of the 1993 Plant Lipid Symposium, Minneapolis, MN, p. 10, (Jul. 29–31, 1993).

Lutz, S., et al., "Intron Sequence Divergence in Type A and B Maize ACCase Genes", *Abstracts, 37th Annual Maize Genetics Conference*, Pacific Grove, CA, Poster No. 34, p. 38 (Mar. 16–19, 1995).

Marshall, L.C., et al., "Allelic Mutations in Acetyl–Coenzyme A Carboxylase Confer Herbicide Tolerance in Maize", *Theor. Appl. Genet.*, 83, 435–442 (1992).

Metzler, D.E., *In: Biochemistry—The Chemical Reactions of Living Cells*, Academic Press, New York, p. 303 (1977).

Roesler, K.R., et al., "Structure and Expression of an Arabidopsis Acetyl–Coenzyme A Carboxylase Gene", *Plant Physiology*, 105, 611–617 (1994).

Roessler, P., "Expression of an Algal Acetyl–CoA Carboxylase Gene in *E. coli* and Yeast", *Abstracts, 11th International Lipid Meeting*, Paris, France (Jun. 1994).

Shulte, W., et al., "A Gene Encoding Acetyl–Coenzyme A Carboxylase from *Brassica napus*", *Plant Physioloyg*, 106, 793–794 (1994).

Shorrosh, B.S., et al., "Molecular Cloning, Characterization, and Elicitation of Acetyl–CoA Carboxylase from Alfalfa", *Proc. Natl. Acad. Sci. USA*, 91, 4323–4327 (May 1994).

Turnham, E., et al., "Changes in the Activity of Acetyl–CoA Carboxylase During Rape–Seed Formation", *Biochem. J.*, 212, 223–229 (1983).

Vahlensieck, H.F., et al., "Identification of the Yeast ACC1 Gene Product (Acetyl–CoA Carboxylase) as the Target of the Polyketide Fungicide Soraphen A", *Current Genetics*, 25, 95–100 (1994).

Van Dee, K.L., "Evidence for Two Independently Segregating Loci Encoding Acetyl–CoA Carboxylase in *Zea mays*", Master of Science Thesis, University of Minnesota, 75 p. (Jan. 1994).

Van Dee, K.L., et al., "RFLP Mapping of Acc1 in *Zea mays* L.", *Agronomy Abstracts*, p. 198 (1992).

Stam M, et al. "The silence of genes in transgenic plants." Ann. Bot. 79: 3–12, 1997.

Koziel MG, et al. "Optimizing expression of transgenes with an emphasis on post–transcriptional events." Plant Mol. Biol. 32: 393–405, 1996.

Smith CJS, et al. "Antisense RNA inhibition of polygalacturonase gene expression in transgenic tomatoes." Nature 334: 724–726, Aug. 25, 1988.

Darnell J, et al. "Molecular Cell Biology." Scientific American Books, NY, pp. 248–257, 1986.

McCabe et al., *Bio/Technol.*, 6, 923 (1988).

Parker et al., Abstract, NCWCC Proceedings, 41, p. 93 (1986).

Parker et al., Abstract, NCWCC Proceedings, 42, p. 56 (Dec. 9, 1987).

Parker et al., "Selection and characterization of corn cell lines tolerant to sethoxydim," 64, Abstract No. 180, (Feb. 3, 1988).

Parker et al., Abstract, Third U of M Research Poster Session: Basic and Applied Bio–Medical Research in Academia and Industry (May 25, 1988).

Phillips et al., In: *Corn and Corn Improvement*, Sprague et al., (eds.), American Society of Agronomy, Madison, WI, Chapter 5 (1988).

Post–Beittenmiller et al., "Regulation of plant fatty acid biosynthesis," *Plant Physiol.*, 100, 923–930 (1992).

Rhodes et al., *Science*, 240, 204 (1987).

Roessler, *Plant Physiol.*, 92, 73–78 (1990).

Vasil, *Bio/Technol.*, 6, 397–402 (Apr. 1988).

Yamada, In: *Plant cell, tissue and organ culture*, Springer–Verlag, Berlin, pp. 144–159 (1977).

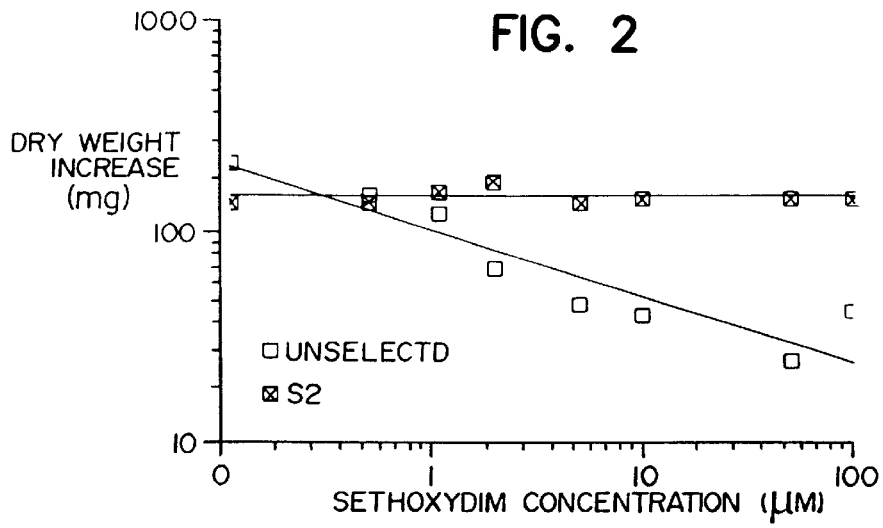
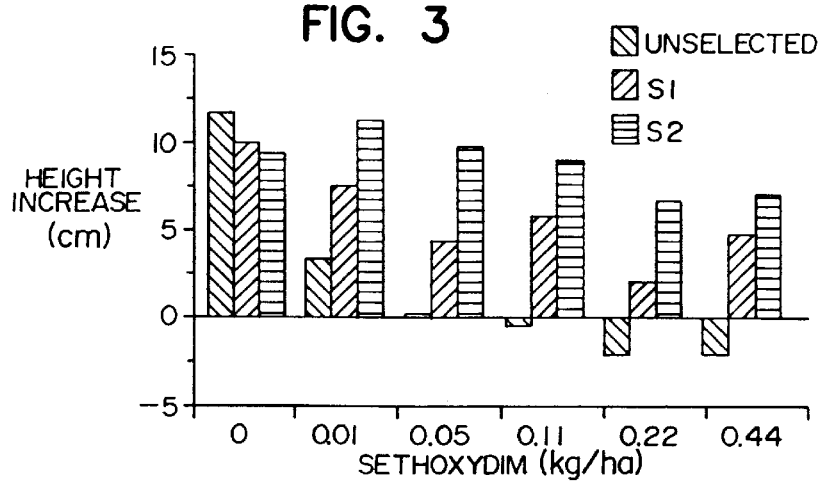
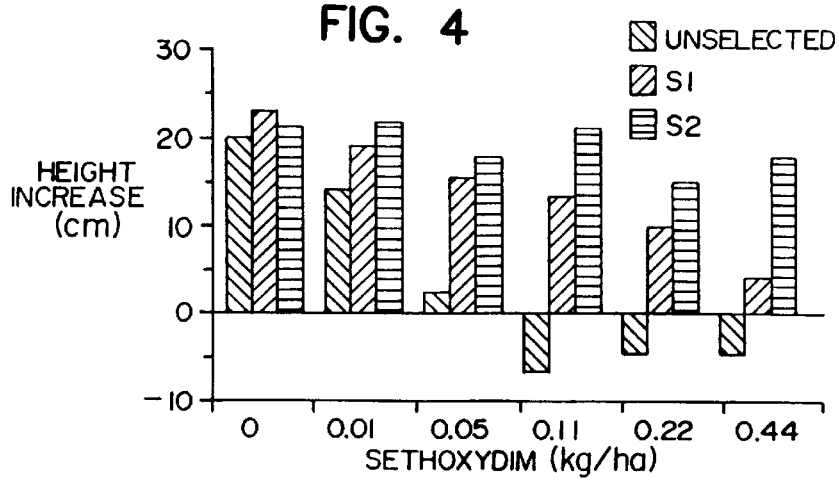

(kb)
origin —

7.8 —

3.9 —

1.9 — leaf
embryo
endosperm
BMS cells

AGA GAT GAA GCT CGC ATG CCA ATG CGC CAC ACA TTC CTC TGG TTG GAT
GAC AAG AGT TGT TAT GAA GAA GAG CAG ATT CTC CGG CAT GTG GAG CCT
CCC CTC TCT ACA CTT CTT GAA TTG GAT AAG TTG AAG GTG AAA GGA TAC
AAT GAA ATG AAG TAT ACT CCT TCG CGT GAC CGC CAA TGG CAT ATC TAC
ACA CTA AGA AAT ACT GAA AAC CCC AAA ATG TTG CAT AGG GTG TTT TTC
CGA ACT ATT GTC AGG CAA CCC AAT GCA GGC AAC AAG TTT AGA TCG CTC
CAG ATC AGC GAC GCN AAG GTA GGA TGT CCC GAA GAA TCT CTT TCA TTT
ACA TCA AAT AGC ATC TTA AGA TCA TTG ATG ACT GCT ATT GAA GAA TTA
GAG CTT CAT GCA ATT AGG ACA GGT CAT TCT CAC ATG TAT TTG TGC ATA
CTG AAA GAG CAA AAG CTT CTT GAC CTC ATT CCA TTT TCA GGG AGT ACA
ATT GTT GAT GTT GGC CAA GAT GAA GCT ACC GCT TGT TCA CTT TTA AAA
TCA ATG GCT TTG AAG ATA CAT GAG CTT GTT GGT GCA AGG ATG CAT CAT
CTG TCT GTA TGC CAG TGG GAG GTG AAA CTC AAG TTG GAC TGT GAT GGC
CCT GCA AGT GGT ACC TGG AGA GTT GTA ACT ACA AAT GTT ACT GGT CAC
ACC TGC ACC ATT GAT ATA TAC CGA GAA GTG GAG GAA ATA GAA TCA CAG
AAG TTA GTG TAC CAT TCA GCC AGT TCG TCA GCT GGA CCA TTG CAT GGT
GTT GCA CTG AAT AAT CCA TAT CAA CCT TTG AGT GTG ATT GAT CTA AAG
CGC TGC TCT GCT AGG AAC AAC AGA ACA ACA TAT TGC TAT GAT TTT CCG
CTG GCC TTT GAA ACT GCA CTG CAG AAG TCA TGG CAG TCC AAT GGC TCT
ACT GTT TCT GAA GGC AAT GAA AAT AGT AAA TCC TAC GTG AAG GCA ACT
GAG CTA GTG TTT GCT GAA AAA CAT GGG TCC TGG GGC ACT CCT ATA ATT
CCG ATG GAA CGC CCT GCT GGG CTC AAC GAC ATT GGT ATG GTC GCT TGG
ATC ATG GAG ATG TCA ACA CCT GAA TTT CCC AAT GGC AGG CAG ATT ATT

FIG. 10

```
GTT GTA GCA AAT GAT ATC ACT TTC AGA GCT GGA TCA TTT GGC CCA AGG
GAA GAT GCA TTT TTT GAA ACT GTC ACT AAC CTG GCT TGC GAA AGG AAA
CTT CCT CTT ATA TAC TTG GCA GCA AAC TCT GGT GCT AGG ATT GGC ATA
GCT GAT GAA GTA AAA TCT TGC TTC CGT GTT GGA TGG TCT GAC GAA GGC
AGT CCT GAA CGA GGG TTT CAG TAC ATC TAT CTG ACT GAA GAA GAC TAT
GCT CGC ATT AGC TCT TCT GTT ATA GCA CAT AAG CTG GAG CTA GAT AGT
GGT GAA ATT AGG TGG ATT ATT GAC TCT GTT GTG GGC AAG GAG GAT GGG
CTT GGT GTC GAG AAC ATA CAT GGA AGT GCT GCT ATT GCC AGT GCT TAT
TCT AGG GCA TAT GAG GAG ACA TTT ACA CTT ACA TTT GTG ACT GGG CGG
ACT GTA GGA ATA GGA GCT TAT CTT GCT CGA CTT GGT ATA CGG TGC ATA
CAG CGT CTT GAC CAG CCT ATT ATT TTA ACA GGG TTT TCT GCC CTG AAC
AAG CTC CTT GGG CGG GAA GTG TAC AGC TCC CAC ATG CAG CTT GGT GGT
CCT AAG ATC ATG GCG ACC AAT GGT GTT GTC CAC CTC ACT GTT CCA GAT
GTC CTT GAA GGT GTT TCC AAT ATA TTG AGG TGG CTC AGC TAT GTT CCT
GCA AAC ATT GGT GGA CCT CTT CCT ATT ACC AAA CCT CTG GAC CCT CCA
GAC AGA CCT GTT GCT TAC ATC CCT GAG AAC ACA TGC GAT CCA CGT GCA
GCT ATC TGT GGT GTA GAT GAC AGC CAA GGG AAA TGG TTG GGT GGT ATG
TTT GAC AAA GAC AGC TTT GTG GAG ACA TTT GAA GGA TGG GCA AAA ACA
GTG GTT ACT GGC AGA GCA AAG CTT GGA GGA ATT
```

FIG. 10 (Cont.)

```
   1  GGTCTTCAAT TGTGCTGTCT GGGCCACGGA ACGACAATGT CACAGCTTGG
  51  ATTAGCCGCA GCTGCCTCAA AGGCCTTGCC ACTACTCCCT AATCGCCAGA
 101  GAAGTTCAGC TGGGACTACA TTCTCATCAT CTTCATTATC GAGGCCCTTA
 151  AACAGAAGGA AAAGCCATAC TCGTTCACTC CGTGATGGCG GAGATGGGGT
 201  ATCAGATGCC AAAAAGCACA GCCAGTCTGT TCGTCAAGGT CTTGCTGGCA
 251  TTATCGACCT CCCAAGTGAG GCACCTTCCG AAGTGGATAT TTCACATGGA
 301  TCTGAGGATC CTAGGGGGCC AACAGATTCT TATCAAATGA ATGGGATTAT
 351  CAATGAAACA CATAATGGAA GACATGCCTC AGTGTCCAAG GTTGTTGAAT
 401  TTTGTGCGGC ACTAGGTGGC AAAACACCAA TTCACAGTAT ATTAGTGCC
 451  AACAATGGAA TGGCAGCAGC AAAATTTATG AGGAGTGTCC GGACATGGGC
 501  TAATGATACT TTTGGATCTG AGAAGGCAAT TCAACTCATA GCTATGGCAA
 551  CTCCGGAAGA CATGAGGATA AATGCAGAAC ACATTAGAAT TGCTGACCAA
 601  TTCGTAGAGG TGCCTGGTGG AACAAACAAT AATAACTACG CCAATGTTCA
 651  ACTCATAGTG GGGATGGCAC AAAAAACTAGG TGTTTCTGCT GTTTGGCCTG
 701  GTTGGGTCA TGCTTCTGAG AATCCTGAAC TGCCAGATCG ATTGACCGCA
 751  AAAGGGATCG TTTTTCTTGG CCCACCCTGG TCATCAATGA ATGCTTTGGG
 801  AGATAAGGTC GGCTCAGCTC TCATTGCTCA AGCAGCCGGG GTCCCAACTC
 851  TTGCTTGGAG TGGATCACAT GTTGAAGTTC CATTAGAGTG CTGCTTAGAC
 901  GCGATACCTG AGGAGATGTA TAGAAAAGCT TGCGTTACTA CCACAGAGGA
 951  AGCAGTTGCA AGTTGTCAAG TGGTTGGTTA TCCTGCCATG ATTAAGGCAT
1001  CCTGGGGAGG TGGTGGTAAA GGAATAAGAA AGGTTCATAA TGATGATGAG
```

FIG. 13

| | | | | |
|---|---|---|---|---|
| 1051 | GTTAGAGCGC | TGTTTAAGCA | AGTACAAGGT | GAAGTCCCTG | GCTCCCCAAT |
| 1101 | ATTTGTCATG | AGGCTTGCAT | CCCAGAGTCG | GCATCTTGAA | GTTCAGTTGC |
| 1151 | TTTGTGATCA | ATATGGTAAT | GTAGCAGCAC | TTCACAGTCG | TGATTGCAGT |
| 1201 | GTGCAACGGC | GACACCAGAA | GATTATTGAA | GAAGGTCCAG | TTACTGTTGC |
| 1251 | TCCTCGTGAG | ACAGTTAAAG | CACTTGAGCA | GGCAGCAAGG | AGGCTTGCTA |
| 1301 | AGGCTGTGGG | TTATGTTGGT | GCTGCTACTG | TTGAGTATCT | TTACAGCATG |
| 1351 | GAAAACTGGAC | ACTACTATTT | TCTGGAACTT | AATCCCCGAC | TACAGGTTGA |
| 1401 | GCATCCAGTG | ACTGAGTGGA | TAGCTGAAGT | GAATCTGCCT | GCAGCTCAAG |
| 1451 | TTGCTGTTGG | AATGGGCATA | CCTCTTTTGC | AGATTCCAGA | AATCAGACGT |
| 1501 | TTCTATGGAA | TGGACTATGG | AGGAGGGTAT | GACATTTGGA | GGAAAACAGC |
| 1551 | AGCTCTTGCT | ACACCATTTA | ATTTTGATGA | AGTAGATTCT | CAATGGCCAA |
| 1601 | AGGGCCATTG | TGTAGCAGTT | AGAATTACTA | GTGAGGACCC | AGATGATGGT |
| 1651 | TTCAAACCTA | CTGGTGGGAA | AGTGAAGGAG | ATAAGTTTTA | AAAGCAAGCC |
| 1701 | TAATGTTTGG | GCCTACTTCT | CAGTAAAGTC | TGGTGGAGGC | ATTCATGAAT |
| 1751 | TTGCTGATTC | TCAGTTTTGA | CATGCTTTTG | CATATGGACT | CTCTAGACCA |
| 1801 | GCAGCTATAA | CAAACATGTC | TCTTGCATTA | AAAGAGATTC | AGATTCGTGG |
| 1851 | AGAAATTCAT | TCAAATGTTG | ATTACACAGT | TGACCTCTTA | AACGCTTCAG |
| 1901 | ACTTCAGAGA | AAACAAGATC | CACACTGGTT | GGCTGGATAC | AAGAATAGCT |
| 1951 | ATGCGTGTTC | AAGCTGAGAG | GCCCCATGG | TATATCTCAG | TGGTTGGAGG |
| 2001 | TGCTTTATAT | AAAACAGTAA | CCACCAATGC | AGCCACTGTT | TCTGAATATG |
| 2051 | TTAGTTATCT | CACCAAGGGC | CATATTCCAC | CAAAGCATAT | ATCCCTTGTC |

FIG. 13 (Cont.)

| | | | | |
|---|---|---|---|---|
| 2101 | AATTCTACAG | TTAATTTGAA | TATAGAAGGG | AGCAAATACA | CAATTGAAAC |
| 2151 | TGTAAGGACT | GGACATGGTA | GCTACAGGTT | GAGAATGAAT | GATTCAACAG |
| 2201 | TTGAAGCGAA | TGTACAATCT | TTATGTGATG | GTGGCCTCTT | AATGCAGTTG |
| 2251 | GATGGAAACA | GCCATGTAAT | TTATGCAGAA | GAAGAAGCTG | GTGGTACACG |
| 2301 | GCTTCAGATT | GATGGAAAGA | CATGTTTATT | GCAGAATGAC | CATGATCCAT |
| 2351 | CGAAGTTATT | AGCTGAGACA | CCCTGCAAAC | TTCTTCGTTT | CTTGGTTGCT |
| 2401 | GATGGTGCTC | ATGTTGATGC | GGATGTACCA | TACGCGGAAG | TTGAGGTTAT |
| 2451 | GAAGATGTGC | ATGCCTCTCT | TGTCACCTGC | TTCTGGTGTC | ATTCATTGTA |
| 2501 | TGATGTCTGA | GGGCCAGGCA | TTGCAGGCTG | GTGATCTTAT | AGCAAGGTTG |
| 2551 | GATCTTGATG | ACCCTTCTGC | TGTGAAAAGA | GCTGAGCCAT | TTGATGAAT |
| 2601 | ATTTCCACAA | ATGGAGCTCC | CTGTTGCTGT | CTCTAGTCAA | GTACACAAAA |
| 2651 | GATATGCTGC | AAGTTTGAAT | GCTGCTCGAA | TGGTCCTTGC | AGGATATGAG |
| 2701 | AAGAGACATC | ATGAAGTCGT | TCAAGATTTG | GTATGCTGCC | TGGACAACCC |
| 2751 | TGAGCTTCCT | TTCCTACAGT | GGGATGAACT | TATGTCTGTT | CTAGCAACGA |
| 2801 | GGCTTCCAAG | AAATCTCAAG | AGTGAGTTAG | AGGATAAATA | CAAGGAATAC |
| 2851 | AAGTTGAATT | TTTACCATGG | AAAAAACGAG | GACTTTCCAT | CCAAGTTGCT |
| 2901 | AAGAGACATC | ATTGAGGAAA | ATCTTTCTTA | TGGTTCAGAG | AAGGAAAAGG |
| 2951 | CTACAAATGA | GAGGCTTGTT | GAGCCTCTTA | TGAACCTACT | GAAGTCATAT |
| 3001 | GAGGGTGGGA | GAGAGAGCCA | TGCACATTTT | GTTGTCAAGT | CTCTTTTCGA |
| 3051 | GGAGTATCTT | ACAGTGGAAG | AACTTTTTAG | TGATGGCATT | CAGTCTGACG |
| 3101 | TGATTGAAAC | ATTGCGGCAT | CAGCACAGTA | AAGACCTGCA | GAAGGTTGTA |

FIG. 13 (Cont.)

| | | | | |
|---|---|---|---|---|
| 3151 | GACATTGTGT | TGTCTCACCA | GGGTGTGAGG | AACAAAGCTA | AGCTTGTAAC |
| 3201 | GGCACTTATG | GAAAAGCTGG | TTTATCCAAA | TCCTGGTGGT | TACAGGGATC |
| 3251 | TGTTAGTTCG | CTTTTCTTCC | CTCAATCATA | AAAGATATTA | TAAGTTGGCC |
| 3301 | CTTAAAGCAA | GTGAACTTCT | TGAACAAACC | AAACTAAGTG | AACTCCGTGC |
| 3351 | AAGCGTTGCA | AGAAGCCTTT | CGGATCTGGG | GATGCATAAG | GGAGAAATGA |
| 3401 | GTATTAAGGA | TAACATGGAA | GATTTAGTCT | CTGCCCCATT | ACCTGTTGAA |
| 3451 | GATGCTCTGA | TTTCTTTGTT | TGATTACAGT | GATCGAACTG | TTCAGCAGAA |
| 3501 | AGTGATTGAG | ACATACATAT | CACGATTGTA | CCAGCCTCAT | CTTGTAAAGG |
| 3551 | ATAGCATCCA | AATGAAATTC | AAGGAATCTG | GTGCTATTAC | TTTTTGGGAA |
| 3601 | TTTTATGAAG | GGCATGTTGA | TACTAGAAAT | GGACATGGGG | CTATTATTGG |
| 3651 | TGGGAAGCGA | TGGGGTGCCA | TGGTCGTTCT | CAAATCACTT | GAATCTGCGT |
| 3701 | CAACAGCCAT | TGTGGCTGCA | TTAAAGGATT | CGGCACAGTT | CAACAGCTCT |
| 3751 | GAGGGCAACA | TGATGCACAT | TGCATTATTG | AGTGCTGAAA | ATGAAAGTAA |
| 3801 | TATAAGTGGA | ATAAGCAGTG | ATGATCAAGC | TCAACATAAG | ATGGAAAAGC |
| 3851 | TTAGCAAGAT | ACTGAAGGAT | ACTAGCCGTTG | CAAGTGATCT | CCAAGCTGCT |
| 3901 | GGTTTGAAGG | TTATAAGTTG | CATTGTTCAA | AGAGATGAAG | CTCGCATGCC |
| 3951 | AATGCGCCAC | ACATTCCTCT | GGTTGGATGA | CAAGAGTTGT | TATGAAGAAG |
| 4001 | AGCAGATTCT | CCGGCATGTG | GAGCCTCCCC | TCTCTACACT | TCTTGAATTG |
| 4051 | GATAAGTTGA | AGGTGAAAGG | ATACAATGAA | ATGAAGTATA | CTCCTTCGCG |
| 4101 | TGACCGCCAA | TGGCATATCT | ACACACTAAG | AAATACTGAA | AACCCAAAA |
| 4151 | TGTTGCATAG | GGTGTTTTTC | CGAACTATTG | TCAGGCAACC | CAATGCAGGC |

FIG. 13 (Cont.)

| | | | | |
|---|---|---|---|---|
| 4201 | AACAAGTTTA | GATCGGCTCA | GATCAGCGAC | GCTGAGGTAG | GATGTCCCGA |
| 4251 | AGAATCTCTT | TCATTTACAT | CAAATAGCAT | CTTAAGATCA | TTGATGACTG |
| 4301 | CTATTGAAGA | ATTAGAGCTT | CATGCAATTA | GGACAGGTCA | TTCTCACATG |
| 4351 | TATTTGTGCA | TACTGAAAGA | GCAAAAGCTT | CTTGACCTCA | TTCCATTTTC |
| 4401 | AGGGAGTACA | ATTGTTGATG | TTGGCCAAGA | TGAAGCTACC | GCTTGTTCAC |
| 4451 | TTTTAAAATC | AATGGCTTTG | AAGATACATG | AGCTTGTTGG | TGCAAGGATG |
| 4501 | CATCATCTGT | CTGTATGCCA | GTGGGAGGTG | AAACTCAAGT | TGGACTGTGA |
| 4551 | TGGCCCTGCA | AGTGGTACCT | GGAGAGTGT | AACTACAAAT | GTTACTGGTC |
| 4601 | ACACCTGCAC | CATTGATATA | TACCGAGAAG | TGGAGGAAAT | AGAATCACAG |
| 4651 | AAGTTAGTGT | ACCATTCAGC | CAGTTCGTCA | GCTGGACCAT | TGCATGGTGT |
| 4701 | TGCACTGAAT | AATCCATATC | AACCTTTGAG | TGTGATTGAT | CTAAAGCGCT |
| 4751 | GCTCTGCTAG | GAACAACAGA | ACAACATATT | GCTATGATTT | TCCGCTGGCC |
| 4801 | TTTGAAACTG | CACTGCAGAA | GTCATGGCAG | TCCAATGGCT | CTACTGTTTC |
| 4851 | TGAAGGCAAT | GAAAATAGTA | AATCCTACGT | GAAGGCAACT | GAGCTAGTGT |
| 4901 | TTGCTGAAAA | ACATGGGTCC | TGGGGCACTC | CTATAATTCC | GATGAACGC |
| 4951 | CCTGCTGGGC | TCAACGACAT | TGGTATGGTC | GCTTGGATCA | TGGAGATGTC |
| 5001 | AACACCTGAA | TTTCCCAATG | GCAGGCAGAT | TATTGTTGTA | GCAAATGATA |
| 5051 | TCACTTTCAG | AGCTGGATCA | TTTGGCCCAA | GGGAAGATGC | ATTTTTTGAA |
| 5101 | ACTGTCACTA | ACCTGCTTG | CGAAAGGAAA | CTTCCTCTTA | TATACTTGGC |
| 5151 | AGCAAACTCT | GGTGCTAGGA | TTGGCATAGC | TGATGAAGTA | AAATCTTGCT |
| 5201 | TCCGTGTTGG | ATGGTCTGAC | GAAGGCAGTC | CTGAACGAGG | GTTTCAGTAC |

FIG. 13 (Cont.)

| | | | | |
|---|---|---|---|---|
| 5251 | ATCTATCTGA | CTGAAGAAGA | CTATGCTCGC | ATTAGCTCTT | CTGTTATAGC |
| 5301 | ACATAAGCTG | GAGCTAGATA | GTGGTGAAAT | TAGGTGGATT | ATTGACTCTG |
| 5351 | TTGTGGGCAA | GGAGGATGGG | CTTGGTGTCG | AGAACATACA | TGGAAGTGCT |
| 5401 | GCTATTGCCA | GTGCTTATTC | TAGGGCATAT | GAGGAGACAT | TTACACTTAC |
| 5451 | ATTTGTGACT | GGGCGGACTG | TAGGAATAGG | AGCTTATCTT | GCTCGACTTG |
| 5501 | GTATACGGTG | CATACAGCGT | CTTGACCAGC | CTATTATTTT | AACAGGGTTT |
| 5551 | TCTGCCCTGA | ACAAGCTCCT | TGGGCGGGAA | GTGTACAGCT | CCCACATGCA |
| 5601 | GCTTGGTGGT | CCTAAGATCA | TGGCGACCAA | TGGTGTTGTC | CACCTCACTG |
| 5651 | TTCCAGATGT | CCTTGAAGGT | GTTTCCAATA | TATTGAGGTG | GCTCAGCTAT |
| 5701 | GTTCCTGCAA | ACATTGGTGG | ACCTCTTCCT | ATTACCAAAC | CTCTGGACCC |
| 5751 | TCCAGACAGA | CCTGTTGCTT | ACATCCCTGA | GAACACATGC | GATCCACGTG |
| 5801 | CAGCTATCTG | TGGTGTAGAT | GACAGCCAAG | GGAAATGGTT | GGGTGGTATG |
| 5851 | TTTGACAAAG | ACAGCTTTGT | GGAGACATTT | GAAGGATGGG | CAAAAACAGT |
| 5901 | GGTTACTGGC | AGAGCAAAGC | TTGGAGGAAT | TCCTGTGGGC | GTCATAGCTG |
| 5951 | TGGAGACACA | GACCATGATG | CAGATCATCC | CTGCTGATCC | AGGTCAGCTT |
| 6001 | GATTCCCATG | AGCGATCTGT | CCCTCGTGCT | GGACAAGTGT | GGTTCCCAGA |
| 6051 | TTCTGCAACC | AAGACCGCTC | AGGCATTATT | AGACTTCAAC | CGTGAAGGAT |
| 6101 | TGCCTCTGTT | CATCCTGGCT | AATTGGAGAG | GCTTCTCTGG | TGGACAAAGA |
| 6151 | GATCTCTTTG | AAGGAATTCT | TCAGGCTGGG | TCAACAATTG | TCGAGAACCT |
| 6201 | TAGGACATAT | AATCAGCCTG | CTTTTGTGTA | CATTCCTATG | GCTGGAGAGC |
| 6251 | TTCGTGGAGG | AGCTTGGGTT | GTGGTCGATA | GCAAAATAAA | TCCAGACCGC |

FIG. 13 (Cont.)

| | | | | |
|---|---|---|---|---|
| 6301 | ATTGAGTGTT | ATGCTGAAAG | GACTGCCAAA | GGTAATGTTC | TCGAACCTCA |
| 6351 | AGGGTTAATT | GAAATCAAGT | TCAGGTCAGA | GGAACTCCAA | GACTGTATGG |
| 6401 | GTAGGCTTGA | CCCAGAGTTG | ATAAATCTGA | AAGCAAAACT | CCAAGATGTA |
| 6451 | AATCATGGAA | ATGGAAGTCT | ACCAGACATA | GAAGGGATTC | GGAAGAGTAT |
| 6501 | AGAAGCACGT | ACGAAACAGT | TGCTGCCTTT | ATATACCCAG | ATTGCAATAC |
| 6551 | GGTTTGCTGA | ATTGCATGAT | ACTTCCCTAA | GAATGGCAGC | TAAAGGTGTG |
| 6601 | ATTAAGAAAG | TTGTAGACTG | GGAAGAATCA | CGCTCGTTCT | TCTATAAAAG |
| 6651 | GCTACGGAGG | AGGATCGCAG | AAGATGTTCT | TGCAAAAGAA | ATAAGGCAGA |
| 6701 | TAGTCGGTGA | TAAATTTACG | CACCAATTAG | CAATGGAGCT | CATCAAGGAA |
| 6751 | TGGTACCTTG | CTTCTCAGGC | CACAACAGGA | AGCACTGGAT | GGGATGACGA |
| 6801 | TGATGCTTTT | GTTGCCTGGA | AGGACAGTCC | TGAAAACTAC | AAGGGCATA |
| 6851 | TCCAAAAGCT | TAGGGCTCAA | AAAGTGTCTC | ATTCGCTCTC | TGATCTTGCT |
| 6901 | GACTCCAGTT | CAGATCTGCA | AGCATTCTCG | CAGGGTCTTT | CTACGCTATT |
| 6951 | AGATAAGATG | GATCCCTCTC | AGAGAGCGAA | GTTTGTTCAG | GAAGTCAAGA |
| 7001 | AGGTCCTTGA | TTGATGATAC | CAACACATCC | AACACAATGT | GTGCATGTCA |
| 7051 | CATCTTTTTG | TTCTAGTACA | TACATAGAAG | GATATTGCTT | GGTCTTGATT |
| 7101 | GATCATGTCT | GATTTAAGTC | GACTATTATT | TCTTGGAATT | TTCTTTTGGA |
| 7151 | CCTGGTGCTA | TGGTTGATGG | ATGTATATTG | GATATGTGCG | TTCTGCCAGG |
| 7201 | TGTAAGCACA | AAGGTTTAGA | CARAMMRARA | RCAAGAGCGA | GTGAACCTGT |
| 7251 | TCTGGTTTTG | CAGTGGTTCA | GTAAGGCAGA | AAGTTGTTAA | ACCGTAGTTC |
| 7301 | TGAGATGTAT | TACCAGTGNC | GCCATGCTGT | ACTTTTAGGG | TGTATAATGC |

FIG. 13 (Cont.)

```
7351  GGATACAAAT  AAACAATTTA  GCGGTTCATT  AAAGTTTGAA  CTCAAATAAC
7401  ATGTTCTTTG  TAAGCATATG  TACCGTACCT  CTACGTGAAA  TAAAGTTGTT
7451  GAATTAGCAT  TCGAAAAAAA
```

FIG. 13 (Cont.)

```
   1  MSQLGLAAAA  SKALPLLPNR  QRSSAGTTFS  SSSLSRPLNR  RKSHTRSLRD
  51  GGDGVSDAKK  HSQSVRQGLA  GIIDLPSEAP  SEVDISHGSE  DPRGPTDSYQ
 101  MNGIINETHN  GRHASVSKVV  EFCAALGGKT  PIHSILVANN  GMAAAKFMRS
 151  VRTWANDTFG  SEKAIQLIAM  ATPEDMRINA  EHIRIADQFV  EVPGGTNNNN
 201  YANVQLIVGM  AQKLGVSAVW  PGWGHASENP  ELPDALTAKG  IVFLGPPASS
 251  MNALGDKVGS  ALIAQAAGVP  TLAWSGSHVE  VPLECCLDAI  PEEMYRKACV
 301  TTTEEAVASC  QVVGYPAMIK  ASWGGGGKGI  RKVHNDDEVR  ALFKQVQGEV
 351  PGSPIFVMRL  ASQSRHLEVQ  LLCDQYGNVA  ALHSRDCSVQ  RRHQKIIEEG
 401  PVTVAPRETV  KALEQAARRL  AKAVGYVGAA  TVEYLYSMET  GDYYFLELNP
 451  RLQVEHPVTE  WIAEVNLPAA  QVAVGMGIPL  WQIPEIRRFY  GMDYGGGYDI
 501  WRKTAALATP  FNFDEVDSQW  PKGHCVAVRI  TSEDPDDGFK  PTGGKVKEIS
 551  FKSKPNVWAY  FSVKSGGGIH  EFADSQFGHA  FAYGLSRPAA  ITNMSLALKE
 601  IQIRGEIHSN  VDYTVDLLNA  SDFRENKIHT  GWLDTRIAMR  VQAERPPWYI
 651  SVVGGALYKT  VTTNAATVSE  YVSYLTKGHI  PPKHISLVNS  TVNLNIEGSK
 701  YTIETVRTGH  GSYRLRMNDS  TVEANVQSLC  DGGLLMQLDG  NSHVIYAEEE
 751  AGGTRLQIDG  KTCLLQNDHD  PSKLLAETPC  KLLRFLVADG  AHVDADVPYA
 801  EVEVMKMCMP  LLSPASGVIH  CMMSEGQALQ  AGDLIARLDL  DDPSAVKRAE
 851  PFDGIFPQME  LPVAVSSQVH  KRYAASLNAA  RMVLAGYEHN  INEVVQDLVC
 901  CLDNPELPFL  QWDELMSVLA  TRLPRNLKSE  LEDKYKEYKL  NFYHGKNEDF
 951  PSKLLRDIIE  ENLSYGSEKE  KATNERLVEP  LMNLLKSYEG  GRESHAHFVV
1001  KSLFEEYLTV  EELFSDGIQS  DVIETLRHQH  SKDLQKVVDI  VLSHQGVRNK
```

FIG. 14

| | | | | |
|---|---|---|---|---|
| 1051 | AKLVTALMEK | LVYPNPGGYR | DLLVRFSSLN | HKRYYKLALK | ASELLEQTKL |
| 1101 | SELRASVARS | LSDLGMHKGE | MSIKDNMEDL | VSAPLPVEDA | LISLFDYSDR |
| 1151 | TVQQKVIETY | ISRLYQPHLV | KDSIQMKFKE | SGAITFWEFY | EGHVDTRNGH |
| 1201 | GAIIGGKRWG | AMVVLKSLES | ASTAIVAALK | DSAQFNSSEG | NMMHIALLSA |
| 1251 | ENESNISGIS | SDDQAQHKME | KLSKILKDTS | VASDLQAAGL | KVISCIVQRD |
| 1301 | EARMPMRHTF | LWLDDKSCYE | EEQILRHVEP | PLSTLLELDK | LKVKGYNEMK |
| 1351 | YTPSRDRQWH | IYTLRNIENP | KMLHRVFFRT | IVRQPNAGNK | FRSAQISDAE |
| 1401 | VGCPEESLSF | TSNSILRSLM | TAIEELELHA | IRTGHSHMYL | CILKEQKLLD |
| 1451 | LIPFSGSTIV | DVGQDEATAC | SLLKSMALKI | HELVGARMHH | LSVCQWEVKL |
| 1501 | KLDCDGPASG | TWRVVTTNVT | GHTCTIDIYR | EVEEIESQKL | VYHSASSSAG |
| 1551 | PLHGVALNNP | YQPLSVIDLK | RCSARNNRTT | YCYDFPLAFE | TALQKSWQSN |
| 1601 | GSTVSEGNEN | SKSYVKATEL | VFAEKHGSWG | TPIIPMERPA | GLNDIGMVAW |
| 1651 | IMEMSTPEFP | NGRQIIVVAN | DITFRAGSFG | PREDAFFETV | TNLACERKLP |
| 1701 | LIYLAANSGA | RIGIADEVKS | CFRVGWSDEG | SPERGFQYIY | LTEEDYARIS |
| 1751 | SSVIAHKLEL | DSGEIRWIID | SVVGKEDGLG | VENIHGSAAI | ASAYSRAYEE |
| 1801 | TFTLTFVTGR | TVGIGAYLAR | LGIRCIQRLD | QPIILTGFSA | LNKLLGREVY |
| 1851 | SSHMQLGGPK | IMATNGVVHL | TVPDVLEGVS | NILRWLSYVP | ANIGGPLPIT |
| 1901 | KPLDPPDRPV | AYIPENTCDP | RAAICGVDDS | QGKWLGGMFD | KDSFVETFEG |
| 1951 | WAKTVVTGRA | KLGGIPVGVI | AVETQTMMQI | IPADPGQLDS | HERSVPRAGQ |
| 2001 | VWFPDSATKT | AQALLDFNRE | GLPLFILANW | RGFSGGQRDL | FEGILQAGST |
| 2051 | IVENLRTYNQ | PAFVYIPMAG | ELRGGAWVVV | DSKINPDRIE | CYAERTAKGN |

FIG. 14 (Cont.)

```
2101  VLEPQGLIEI  KFRSEELQDC  MGRLDPELIN  LKAKLQDVNH  GNGSLPDIEG
2151  IRKSIEARTK  QLLPLYTQIA  IRFAELHDTS  LRMAAKGVIK  KVVDWEESRS
2201  FFYKRLRRRI  AEDVLAKEIR  QIVGDKFTHQ  LAMELIKEWY  LASQATTGST
2251  GWDDDAFVA   WKDSPENYKG  HIQKLRAQKV  SHSLSDLADS  SSDLQAFSQG
2301  LSTLLDKMDP  SQRAKFVQEV  KKVLD
```

FIG. 14 (Cont.)

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 2001 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
AGAGATGAAG CTCGCATGCC AATGCGCCAC ACATTCCTCT GGTTGGATGA CAAGAGTTGT      60

TATGAAGAAG AGCAGATTCT CCGGCATGTG GAGCCTCCCC TCTCTACACT TCTTGAATTG     120

GATAAGTTGA AGGTGAAAGG ATACAATGAA ATGAAGTATA CTCCTTCGCG TGACCGCCAA     180

TGGCATATCT ACACACTAAG AAATACTGAA AACCCCAAAA TGTTGCATAG GGTGTTTTTC     240

CGAACTATTG TCAGGCAACC CAATGCAGGC AACAAGTTTA GATCGGCTCA GATCAGCGAC     300

GCNAAGGTAG GATGTCCCGA AGAATCTCTT TCATTTACAT CAAATAGCAT CTTAAGATCA     360

TTGATGACTG CTATTGAAGA ATTAGAGCTT CATGCAATTA GGACAGGTCA TTCTCACATG     420

TATTTGTGCA TACTGAAAGA GCAAAAGCTT CTTGACCTCA TTCCATTTTC AGGGAGTACA     480

ATTGTTGATG TTGGCCAAGA TGAAGCTACC GCTTGTTCAC TTTTAAAATC AATGGCTTTG     540

AAGATACATG AGCTTGTTGG TGCAAGGATG CATCATCTGT CTGTATGCCA GTGGGAGGTG     600

AAACTCAAGT TGGACTGTGA TGGCCCTGCA AGTGGTACCT GGAGAGTTGT AACTACAAAT     660

GTTACTGGTC ACACCTGCAC CATTGATATA TACCGAGAAG TGGAGGAAAT AGAATCACAG     720

AAGTTAGTGT ACCATTCAGC CAGTTCGTCA GCTGGACCAT TGCATGGTGT TGCACTGAAT     780

AATCCATATC AACCTTTGAG TGTGATTGAT CTAAAGCGCT GCTCTGCTAG GAACAACAGA     840
```

```
ACAACATATT GCTATGATTT TCCGCTGGCC TTTGAAACTG CACTGCAGAA GTCATGGCAG      900

TCCAATGGCT CTACTGTTTC TGAAGGCAAT GAAAATAGTA AATCCTACGT GAAGGCAACT      960

GAGCTAGTGT TTGCTGAAAA ACATGGGTCC TGGGCACTC CTATAATTCC GATGGAACGC      1020

CCTGCTGGGC TCAACGACAT TGGTATGGTC GCTTGGATCA TGGAGATGTC AACACCTGAA     1080

TTTCCCAATG GCAGGCAGAT TATTGTTGTA GCAAATGATA TCACTTTCAG AGCTGGATCA     1140

TTTGGCCCAA GGGAAGATGC ATTTTTTGAA ACTGTCACTA ACCTGGCTTG CGAAAGGAAA     1200

CTTCCTCTTA TATACTTGGC AGCAAACTCT GGTGCTAGGA TTGGCATAGC TGATGAAGTA     1260

AAATCTTGCT TCCGTGTTGG ATGGTCTGAC GAAGGCAGTC CTGAACGAGG GTTTCAGTAC     1320

ATCTATCTGA CTGAAGAAGA CTATGCTCGC ATTAGCTCTT CTGTTATAGC ACATAAGCTG     1380

GAGCTAGATA GTGGTGAAAT TAGGTGGATT ATTGACTCTG TTGTGGGCAA GGAGGATGGG     1440

CTTGGTGTCG AGAACATACA TGGAAGTGCT GCTATTGCCA GTGCTTATTC TAGGGCATAT     1500

GAGGAGACAT TTACACTTAC ATTTGTGACT GGGCGGACTG TAGGAATAGG AGCTTATCTT     1560

GCTCGACTTG GTATACGGTG CATACAGCGT CTTGACCAGC CTATTATTTT AACAGGGTTT     1620

TCTGCCCTGA ACAAGCTCCT TGGGCGGGAA GTGTACAGCT CCCACATGCA GCTTGGTGGT     1680

CCTAAGATCA TGGCGACCAA TGGTGTTGTC CACCTCACTG TTCCAGATGT CCTTGAAGGT     1740

GTTTCCAATA TATTGAGGTG GCTCAGCTAT GTTCCTGCAA ACATTGGTGG ACCTCTTCCT     1800

ATTACCAAAC CTCTGGACCC TCCAGACAGA CCTGTTGCTT ACATCCCTGA GAACACATGC     1860

GATCCACGTG CAGCTATCTG TGGTGTAGAT GACAGCCAAG GGAAATGGTT GGGTGGTATG     1920

TTTGACAAAG ACAGCTTTGT GGAGACATTT GAAGGATGGG CAAAAACAGT GGTTACTGGC     1980

AGAGCAAAGC TTGGAGGAAT T                                               2001

(2) INFORMATION FOR SEQ ID NO: 2:

(i) SEQUENCE CHARACTERISTICS:
        (A) LENGTH: 258 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

GTTCCTGCAA ACATTGGTGG ACCTCTTCCT ATTACCAAAC CTCTGGACCC TCCAGACAGA       60

CCTGTTGCTT ACATCCCTGA GAACACATGC GATCCACGTG CAGCTATCTG TGGTGTAGAT      120

GACAGCCAAG GGAAATGGTT GGGTGGTATG TTTGACAAAG ACAGCTTTGT GGAGACATTT      180

GAAGGATGGG CAAAAACAGT GGTTACTGGC AGAGCAAAGC TTGGAGGAAT TCCTGTGGGC      240

GTCATAGCTG TGGAGACA                                                    258

(2) INFORMATION FOR SEQ ID NO: 3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

Val Met Lys Met
1
```

(2) INFORMATION FOR SEQ ID NO: 4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
GCCAGATTCC ACCAAAGCAT ATATCC                                          26
```

(2) INFORMATION FOR SEQ ID NO: 5:

(i) SEQUENCE CHARACTERISTICS:
        (A) LENGTH: 7470 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
GGTCTTCAAT TGTGCTGTCT GGGCCACGGA ACGACAATGT CACAGCTTGG ATTAGCCGCA      60
GCTGCCTCAA AGGCCTTGCC ACTACTCCCT AATCGCCAGA GAAGTTCAGC TGGGACTACA     120
TTCTCATCAT CTTCATTATC GAGGCCCTTA ACAGAAGGA AAAGCCATAC TCGTTCACTC      180
CGTGATGGCG GAGATGGGGT ATCAGATGCC AAAAAGCACA GCCAGTCTGT TCGTCAAGGT     240
CTTGCTGGCA TTATCGACCT CCCAAGTGAG GCACCTTCCG AAGTGGATAT TTCACATGGA     300
TCTGAGGATC CTAGGGGGCC AACAGATTCT TATCAAATGA ATGGGATTAT CAATGAAACA     360
CATAATGGAA GACATGCCTC AGTGTCCAAG GTTGTTGAAT TTTGTGCGGC ACTAGGTGGC     420
AAAACACCAA TTCACAGTAT ATTAGTGGCC AACAATGGAA TGGCAGCAGC AAAATTTATG     480
AGGAGTGTCC GGACATGGGC TAATGATACT TTTGGATCTG AGAAGGCAAT TCAACTCATA     540
GCTATGGCAA CTCCGGAAGA CATGAGGATA AATGCAGAAC ACATTAGAAT TGCTGACCAA     600
TTCGTAGAGG TGCCTGGTGG AACAAACAAT AATAACTACG CCAATGTTCA ACTCATAGTG     660
GGGATGGCAC AAAAACTAGG TGTTTCTGCT GTTTGGCCTG GTTGGGGTCA TGCTTCTGAG     720
AATCCTGAAC TGCCAGATGC ATTGACCGCA AAAGGGATCG TTTTTCTTGG CCCACCTGCA     780
TCATCAATGA ATGCTTTGGG AGATAAGGTC GGCTCAGCTC TCATTGCTCA AGCAGCCGGG     840
GTCCCAACTC TTGCTTGGAG TGGATCACAT GTTGAAGTTC CATTAGAGTG CTGCTTAGAC     900
GCGATACCTG AGGAGATGTA TAGAAAAGCT TGCGTTACTA CCACAGAGGA AGCAGTTGCA     960
AGTTGTCAAG TGGTTGGTTA TCCTGCCATG ATTAAGGCAT CCTGGGGAGG TGGTGGTAAA    1020
GGAATAAGAA AGGTTCATAA TGATGATGAG GTTAGAGCGC TGTTTAAGCA AGTACAAGGT    1080
GAAGTCCCTG GCTCCCCAAT ATTTGTCATG AGGCTTGCAT CCCAGAGTCG GCATCTTGAA    1140
GTTCAGTTGC TTTGTGATCA ATATGGTAAT GTAGCAGCAC TTCACAGTCG TGATTGCAGT    1200
GTGCAACGGC GACACCAGAA GATTATTGAA GAAGGTCCAG TTACTGTTGC TCCTCGTGAG    1260
ACAGTTAAAG CACTTGAGCA GGCAGCAAGG AGGCTTGCTA AGGCTGTGGG TTATGTTGGT    1320
GCTGCTACTG TTGAGTATCT TTACAGCATG GAAACTGGAG ACTACTATTT TCTGGAACTT    1380
AATCCCCGAC TACAGGTTGA GCATCCAGTC ACTGAGTGGA TAGCTGAAGT GAATCTGCCT    1440
GCAGCTCAAG TTGCTGTTGG AATGGGCATA CCTCTTTGGC AGATTCCAGA AATCAGACGT    1500
TTCTATGGAA TGGACTATGG AGGAGGGTAT GACATTTGGA GGAAAACAGC AGCTCTTGCT    1560
```

```
ACACCATTTA ATTTTGATGA AGTAGATTCT CAATGGCCAA AGGGCCATTG TGTAGCAGTT    1620

AGAATTACTA GTGAGGACCC AGATGATGGT TTCAAACCTA CTGGTGGGAA AGTGAAGGAG    1680

ATAAGTTTTA AAAGCAAGCC TAATGTTTGG GCCTACTTCT CAGTAAAGTC TGGTGGAGGC    1740

ATTCATGAAT TTGCTGATTC TCAGTTTGGA CATGCTTTTG CATATGGACT CTCTAGACCA    1800

GCAGCTATAA CAAACATGTC TCTTGCATTA AAAGAGATTC AGATTCGTGG AGAAATTCAT    1860

TCAAATGTTG ATTACACAGT TGACCTCTTA AACGCTTCAG ACTTCAGAGA AAACAAGATC    1920

CACACTGGTT GGCTGGATAC AAGAATAGCT ATGCGTGTTC AAGCTGAGAG GCCCCCATGG    1980

TATATCTCAG TGGTTGGAGG TGCTTTATAT AAAACAGTAA CCACCAATGC AGCCACTGTT    2040

TCTGAATATG TTAGTTATCT CACCAAGGGC CATATTCCAC AAAGCATAT ATCCCTTGTC      2100

AATTCTACAG TTAATTTGAA TATAGAAGGG AGCAAATACA CAATTGAAAC TGTAAGGACT    2160

GGACATGGTA GCTACAGGTT GAGAATGAAT GATTCAACAG TTGAAGCGAA TGTACAATCT    2220

TTATGTGATG GTGGCCTCTT AATGCAGTTG GATGGAAACA GCCATGTAAT TTATGCAGAA    2280

GAAGAAGCTG GTGGTACACG GCTTCAGATT GATGGAAAGA CATGTTTATT GCAGAATGAC    2340

CATGATCCAT CGAAGTTATT AGCTGAGACA CCCTGCAAAC TTCTTCGTTT CTTGGTTGCT    2400

GATGGTGCTC ATGTTGATGC GGATGTACCA TACGCGGAAG TTGAGGTTAT GAAGATGTGC    2460

ATGCCTCTCT TGTCACCTGC TTCTGGTGTC ATTCATTGTA TGATGTCTGA GGGCCAGGCA    2520

TTGCAGGCTG GTGATCTTAT AGCAAGGTTG GATCTTGATG ACCCTTCTGC TGTGAAAAGA    2580

GCTGAGCCAT TTGATGGAAT ATTTCCACAA ATGGAGCTCC CTGTTGCTGT CTCTAGTCAA    2640

GTACACAAAA GATATGCTGC AAGTTTGAAT GCTGCTCGAA TGGTCCTTGC AGGATATGAG    2700

CACAATATTA TGAAGTCGT TCAAGATTTG GTATGCTGCC TGGACAACCC TGAGCTTCCT     2760

TTCCTACAGT GGGATGAACT TATGTCTGTT CTAGCAACGA GGCTTCCAAG AAATCTCAAG    2820

AGTGAGTTAG AGGATAAATA CAAGGAATAC AAGTTGAATT TTTACCATGG AAAAAACGAG    2880

GACTTTCCAT CCAAGTTGCT AAGAGACATC ATTGAGGAAA ATCTTTCTTA TGGTTCAGAG    2940

AAGGAAAAGG CTACAAATGA GAGGCTTGTT GAGCCTCTTA TGAACCTACT GAAGTCATAT    3000

GAGGGTGGGA GAGAGAGCCA TGCACATTTT GTTGTCAAGT CTCTTTTCGA GGAGTATCTT    3060

ACAGTGGAAG AACTTTTTAG TGATGGCATT CAGTCTGACG TGATTGAAAC ATTGCGGCAT    3120

CAGCACAGTA AAGACCTGCA GAAGGTTGTA GACATTGTGT TGTCTCACCA GGGTGTGAGG    3180

AACAAAGCTA AGCTTGTAAC GGCACTTATG GAAAAGCTGG TTTATCCAAA TCCTGGTGGT    3240

TACAGGGATC TGTTAGTTCG CTTTTCTTCC CTCAATCATA AAAGATATTA TAAGTTGGCC    3300

CTTAAAGCAA GTGAACTTCT TGAACAAACC AAACTAAGTG AACTCCGTGC AAGCGTTGCA    3360

AGAAGCCTTT CGGATCTGGG GATGCATAAG GGAGAAATGA GTATTAAGGA TAACATGGAA    3420

GATTTAGTCT CTGCCCCATT ACCTGTTGAA GATGCTCTGA TTTCTTTGTT TGATTACAGT    3480

GATCGAACTG TTCAGCAGAA AGTGATTGAG ACATACATAT CACGATTGTA CCAGCCTCAT    3540

CTTGTAAAGG ATAGCATCCA AATGAAATTC AAGGAATCTG GTGCTATTAC TTTTTGGGAA    3600

TTTTATGAAG GCATGTTGA TACTAGAAAT GGACATGGGG CTATTATTGG TGGGAAGCGA     3660

TGGGGTGCCA TGGTCGTTCT CAAATCACTT GAATCTGCGT CAACAGCCAT TGTGGCTGCA    3720

TTAAAGGATT CGGCACAGTT CAACAGCTCT GAGGGCAACA TGATGCACAT TGCATTATTG    3780

AGTGCTGAAA ATGAAAGTAA TATAAGTGGA ATAAGCAGTG ATGATCAAGC TCAACATAAG    3840

ATGGAAAAGC TTAGCAAGAT ACTGAAGGAT ACTAGCGTTG CAAGTGATCT CCAAGCTGCT    3900
```

-continued

```
GGTTTGAAGG TTATAAGTTG CATTGTTCAA AGAGATGAAG CTCGCATGCC AATGCGCCAC     3960

ACATTCCTCT GGTTGGATGA CAAGAGTTGT TATGAAGAAG AGCAGATTCT CCGGCATGTG     4020

GAGCCTCCCC TCTCTACACT TCTTGAATTG GATAAGTTGA AGGTGAAAGG ATACAATGAA     4080

ATGAAGTATA CTCCTTCGCG TGACCGCCAA TGGCATATCT ACACACTAAG AAATACTGAA     4140

AACCCCAAAA TGTTGCATAG GGTGTTTTTC CGAACTATTG TCAGGCAACC CAATGCAGGC     4200

AACAAGTTTA GATCGGCTCA GATCAGCGAC GCTGAGGTAG GATGTCCCGA AGAATCTCTT     4260

TCATTTACAT CAAATAGCAT CTTAAGATCA TTGATGACTG CTATTGAAGA ATTAGAGCTT     4320

CATGCAATTA GGACAGGTGA TTCTCACATG TATTTGTGCA TACTGAAAGA GCAAAAGCTT     4380

CTTGACCTCA TTCCATTTTC AGGGAGTACA ATTGTTGATG TTGGCCAAGA TGAAGCTACC     4440

GCTTGTTCAC TTTTAAAATC AATGGCTTTG AAGATACATG AGCTTGTTGG TGCAAGGATG     4500

CATCATCTGT CTGTATGCCA GTGGGAGGTG AAACTCAAGT TGGACTGTGA TGGCCCTGCA     4560

AGTGGTACCT GGAGAGTTGT AACTACAAAT GTTACTGGTC ACACCTGCAC CATTGATATA     4620

TACCGAGAAG TGGAGGAAAT AGAATCACAG AAGTTAGTGT ACCATTCAGC CAGTTCGTCA     4680

GCTGGACCAT TGCATGGTGT TGCACTGAAT AATCCATATC AACCTTTGAG TGTGATTGAT     4740

CTAAAGCGCT GCTCTGCTAG GAACAACAGA ACAACATATT GCTATGATTT TCCGCTGGCC     4800

TTTGAAACTG CACTGCAGAA GTCATGGCAG TCCAATGGCT CTACTGTTTC TGAAGGCAAT     4860

GAAAATAGTA AATCCTACGT GAAGGCAACT GAGCTAGTGT TTGCTGAAAA ACATGGGTCC     4920

TGGGGCACTC CTATAATTCC GATGGAACGC CCTGCTGGGC TCAACGACAT TGGTATGGTC     4980

GCTTGGATCA TGGAGATGTC AACACCTGAA TTTCCCAATG GCAGGCAGAT TATTGTTGTA     5040

GCAAATGATA TCACTTTCAG AGCTGGATCA TTTGGCCCAA GGGAAGATGC ATTTTTTGAA     5100

ACTGTCACTA ACCTGGCTTG CGAAAGGAAA CTTCCTCTTA TATACTTGGC AGCAAACTCT     5160

GGTGCTAGGA TTGGCATAGC TGATGAAGTA AAATCTTGCT TCCGTGTTGG ATGGTCTGAC     5220

GAAGGCAGTC CTGAACGAGG GTTTCAGTAC ATCTATCTGA CTGAAGAAGA CTATGCTCGC     5280

ATTAGCTCTT CTGTTATAGC ACATAAGCTG GAGCTAGATA GTGGTGAAAT TAGGTGGATT     5340

ATTGACTCTG TTGTGGGCAA GGAGGATGGG CTTGGTGTCG AGAACATACA TGGAAGTGCT     5400

GCTATTGCCA GTGCTTATTC TAGGGCATAT GAGGAGACAT TTACACTTAC ATTTGTGACT     5460

GGGCGGACTG TAGGAATAGG AGCTTATCTT GCTCGACTTG GTATACGGTG CATACAGCGT     5520

CTTGACCAGC CTATTATTTT AACAGGGTTT TCTGCCCTGA ACAAGCTCCT TGGGCGGGAA     5580

GTGTACAGCT CCCACATGCA GCTTGGTGGT CCTAAGATCA TGGCGACCAA TGGTGTTGTC     5640

CACCTCACTG TTCCAGATGT CCTTGAAGGT GTTTCCAATA TATTGAGGTG GCTCAGCTAT     5700

GTTCCTGCAA ACATTGGTGG ACCTCTTCCT ATTACCAAAC CTCTGGACCC TCCAGACAGA     5760

CCTGTTGCTT ACATCCCTGA GAACACATGC GATCCACGTG CAGCTATCTG TGGTGTAGAT     5820

GACAGCCAAG GGAAATGGTT GGGTGGTATG TTTGACAAAG ACAGCTTTGT GGAGACATTT     5880

GAAGGATGGG CAAAAACAGT GGTTACTGGC AGAGCAAAGC TTGGAGGAAT TCCTGTGGGC     5940

GTCATAGCTG TGGAGACACA GACCATGATG CAGATCATCC CTGCTGATCC AGGTCAGCTT     6000

GATTCCCATG AGCGATCTGT CCCTCGTGCT GGACAAGTGT GGTTCCCAGA TTCTGCAACC     6060

AAGACCGCTC AGGCATTATT AGACTTCAAC CGTGAAGGAT TGCCTCTGTT CATCCTGGCT     6120

AATTGGAGAG GCTTCTCTGG TGGACAAAGA GATCTCTTTG AAGGAATTCT TCAGGCTGGG     6180

TCAACAATTG TCGAGAACCT TAGGACATAT AATCAGCCTG CTTTTGTGTA CATTCCTATG     6240

GCTGGAGAGC TTCGTGGAGG AGCTTGGGTT GTGGTCGATA GCAAAATAAA TCCAGACCGC     6300
```

```
ATTGAGTGTT ATGCTGAAAG GACTGCCAAA GGTAATGTTC TCGAACCTCA AGGGTTAATT      6360

GAAATCAAGT TCAGGTCAGA GGAACTCCAA GACTGTATGG GTAGGCTTGA CCCAGAGTTG      6420

ATAAATCTGA AAGCAAAACT CCAAGATGTA AATCATGGAA ATGGAAGTCT ACCAGACATA      6480

GAAGGGATTC GGAAGAGTAT AGAAGCACGT ACGAAACAGT TGCTGCCTTT ATATACCCAG      6540

ATTGCAATAC GGTTTGCTGA ATTGCATGAT ACTTCCCTAA GAATGGCAGC TAAAGGTGTG      6600

ATTAAGAAAG TTGTAGACTG GAAGAATCA CGCTCGTTCT TCTATAAAAG GCTACGGAGG       6660

AGGATCGCAG AAGATGTTCT TGCAAAAGAA ATAAGGCAGA TAGTCGGTGA TAAATTTACG      6720

CACCAATTAG CAATGGAGCT CATCAAGGAA TGGTACCTTG CTTCTCAGGC CACAACAGGA      6780

AGCACTGGAT GGGATGACGA TGATGCTTTT GTTGCCTGGA AGGACAGTCC TGAAAACTAC      6840

AAGGGGCATA TCCAAAAGCT TAGGGCTCAA AAAGTGTCTC ATTCGCTCTC TGATCTTGCT      6900

GACTCCAGTT CAGATCTGCA AGCATTCTCG CAGGGTCTTT CTACGCTATT AGATAAGATG      6960

GATCCCTCTC AGAGAGCGAA GTTTGTTCAG GAAGTCAAGA AGGTCCTTGA TTGATGATAC      7020

CAACACATCC AACACAATGT GTGCATGTCA CATCTTTTTG TTCTAGTACA TACATAGAAG      7080

GATATTGCTT GGTCTTGATT GATCATGTCT GATTTAAGTC GACTATTATT TCTTGGAATT      7140

TTCTTTTGGA CCTGGTGCTA TGGTTGATGG ATGTATATTG GATATGTGCG TTCTGCCAGG      7200

TGTAAGCACA AAGGTTTAGA CARAMMRARA RCAAGAGCGA GTGAACCTGT TCTGGTTTTG      7260

CAGTGGTTCA GTAAGGCAGA AAGTTGTTAA ACCGTAGTTC TGAGATGTAT TACCAGTGNC      7320

GCCATGCTGT ACTTTTAGGG TGTATAATGC GGATACAAAT AAACAATTTA GCGGTTCATT      7380

AAAGTTTGAA CTCAAATAAC ATGTTCTTTG TAAGCATATG TACCGTACCT CTACGTGAAA      7440

TAAAGTTGTT GAATTAGCAT TCGAAAAAAA                                      7470

(2) INFORMATION FOR SEQ ID NO: 6:

(i) SEQUENCE CHARACTERISTICS:
        (A) LENGTH: 2325 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Met Ser Gln Leu Gly Leu Ala Ala Ala Ser Lys Ala Leu Pro Leu
1               5                   10                  15

Leu Pro Asn Arg Gln Arg Ser Ser Ala Gly Thr Thr Phe Ser Ser
            20                  25                  30

Ser Leu Ser Arg Pro Leu Asn Arg Arg Lys Ser His Thr Arg Ser Leu
        35                  40                  45

Arg Asp Gly Gly Asp Gly Val Ser Asp Ala Lys Lys His Ser Gln Ser
    50                  55                  60

Val Arg Gln Gly Leu Ala Gly Ile Ile Asp Leu Pro Ser Glu Ala Pro
65                  70                  75                  80

Ser Glu Val Asp Ile Ser His Gly Ser Glu Asp Pro Arg Gly Pro Thr
                85                  90                  95

Asp Ser Tyr Gln Met Asn Gly Ile Ile Asn Glu Thr His Asn Gly Arg
            100                 105                 110

His Ala Ser Val Ser Lys Val Val Glu Phe Cys Ala Ala Leu Gly Gly
        115                 120                 125

Lys Thr Pro Ile His Ser Ile Leu Val Ala Asn Asn Gly Met Ala Ala
```

```
            130                 135                 140
Ala Lys Phe Met Arg Ser Val Arg Thr Trp Ala Asn Asp Thr Phe Gly
145                 150                 155                 160

Ser Glu Lys Ala Ile Gln Leu Ile Ala Met Ala Thr Pro Glu Asp Met
                165                 170                 175

Arg Ile Asn Ala Glu His Ile Arg Ile Ala Asp Gln Phe Val Glu Val
                180                 185                 190

Pro Gly Gly Thr Asn Asn Asn Tyr Ala Asn Val Gln Leu Ile Val
                195                 200                 205

Gly Met Ala Gln Lys Leu Gly Val Ser Ala Val Trp Pro Gly Trp Gly
            210                 215                 220

His Ala Ser Glu Asn Pro Glu Leu Pro Asp Ala Leu Thr Ala Lys Gly
225                 230                 235                 240

Ile Val Phe Leu Gly Pro Pro Ala Ser Ser Met Asn Ala Leu Gly Asp
                245                 250                 255

Lys Val Gly Ser Ala Leu Ile Ala Gln Ala Ala Gly Val Pro Thr Leu
                260                 265                 270

Ala Trp Ser Gly Ser His Val Glu Val Pro Leu Glu Cys Cys Leu Asp
            275                 280                 285

Ala Ile Pro Glu Glu Met Tyr Arg Lys Ala Cys Val Thr Thr Thr Glu
            290                 295                 300

Glu Ala Val Ala Ser Cys Gln Val Val Gly Tyr Pro Ala Met Ile Lys
305                 310                 315                 320

Ala Ser Trp Gly Gly Gly Gly Lys Gly Ile Arg Lys Val His Asn Asp
                325                 330                 335

Asp Glu Val Arg Ala Leu Phe Lys Gln Val Gln Gly Glu Val Pro Gly
                340                 345                 350

Ser Pro Ile Phe Val Met Arg Leu Ala Ser Gln Ser Arg His Leu Glu
                355                 360                 365

Val Gln Leu Leu Cys Asp Gln Tyr Gly Asn Val Ala Ala Leu His Ser
            370                 375                 380

Arg Asp Cys Ser Val Gln Arg Arg His Gln Lys Ile Ile Glu Glu Gly
385                 390                 395                 400

Pro Val Thr Val Ala Pro Arg Glu Thr Val Lys Ala Leu Glu Gln Ala
                405                 410                 415

Ala Arg Arg Leu Ala Lys Ala Val Gly Tyr Val Gly Ala Ala Thr Val
                420                 425                 430

Glu Tyr Leu Tyr Ser Met Glu Thr Gly Asp Tyr Tyr Phe Leu Glu Leu
            435                 440                 445

Asn Pro Arg Leu Gln Val Glu His Pro Val Thr Glu Trp Ile Ala Glu
            450                 455                 460

Val Asn Leu Pro Ala Ala Gln Val Ala Val Gly Met Gly Ile Pro Leu
465                 470                 475                 480

Trp Gln Ile Pro Glu Ile Arg Arg Phe Tyr Gly Met Asp Tyr Gly Gly
                485                 490                 495

Gly Tyr Asp Ile Trp Arg Lys Thr Ala Ala Leu Ala Thr Pro Phe Asn
                500                 505                 510

Phe Asp Glu Val Asp Ser Gln Trp Pro Lys Gly His Cys Val Ala Val
                515                 520                 525

Arg Ile Thr Ser Glu Asp Pro Asp Asp Gly Phe Lys Pro Thr Gly Gly
            530                 535                 540

Lys Val Lys Glu Ile Ser Phe Lys Ser Lys Pro Asn Val Trp Ala Tyr
545                 550                 555                 560
```

-continued

```
Phe Ser Val Lys Ser Gly Gly Gly Ile His Glu Phe Ala Asp Ser Gln
            565                 570                 575
Phe Gly His Ala Phe Ala Tyr Gly Leu Ser Arg Pro Ala Ala Ile Thr
            580                 585                 590
Asn Met Ser Leu Ala Leu Lys Glu Ile Gln Ile Arg Gly Glu Ile His
            595                 600                 605
Ser Asn Val Asp Tyr Thr Val Asp Leu Leu Asn Ala Ser Asp Phe Arg
            610                 615                 620
Glu Asn Lys Ile His Thr Gly Trp Leu Asp Thr Arg Ile Ala Met Arg
625                 630                 635                 640
Val Gln Ala Glu Arg Pro Pro Trp Tyr Ile Ser Val Val Gly Gly Ala
            645                 650                 655
Leu Tyr Lys Thr Val Thr Thr Asn Ala Ala Thr Val Ser Glu Tyr Val
            660                 665                 670
Ser Tyr Leu Thr Lys Gly His Ile Pro Pro Lys His Ile Ser Leu Val
            675                 680                 685
Asn Ser Thr Val Asn Leu Asn Ile Glu Gly Ser Lys Tyr Thr Ile Glu
            690                 695                 700
Thr Val Arg Thr Gly His Gly Ser Tyr Arg Leu Arg Met Asn Asp Ser
705                 710                 715                 720
Thr Val Glu Ala Asn Val Gln Ser Leu Cys Asp Gly Gly Leu Leu Met
            725                 730                 735
Gln Leu Asp Gly Asn Ser His Val Ile Tyr Ala Glu Glu Ala Gly
            740                 745                 750
Gly Thr Arg Leu Gln Ile Asp Gly Lys Thr Cys Leu Leu Gln Asn Asp
            755                 760                 765
His Asp Pro Ser Lys Leu Leu Ala Glu Thr Pro Cys Lys Leu Leu Arg
            770                 775                 780
Phe Leu Val Ala Asp Gly Ala His Val Asp Ala Asp Val Pro Tyr Ala
785                 790                 795                 800
Glu Val Glu Val Met Lys Met Cys Met Pro Leu Leu Ser Pro Ala Ser
            805                 810                 815
Gly Val Ile His Cys Met Met Ser Glu Gly Gln Ala Leu Gln Ala Gly
            820                 825                 830
Asp Leu Ile Ala Arg Leu Asp Leu Asp Asp Pro Ser Ala Val Lys Arg
            835                 840                 845
Ala Glu Pro Phe Asp Gly Ile Phe Pro Gln Met Glu Leu Pro Val Ala
850                 855                 860
Val Ser Ser Gln Val His Lys Arg Tyr Ala Ala Ser Leu Asn Ala Ala
865                 870                 875                 880
Arg Met Val Leu Ala Gly Tyr Glu His Asn Ile Asn Glu Val Val Gln
            885                 890                 895
Asp Leu Val Cys Cys Leu Asp Asn Pro Glu Leu Pro Phe Leu Gln Trp
            900                 905                 910
Asp Glu Leu Met Ser Val Leu Ala Thr Arg Leu Pro Arg Asn Leu Lys
            915                 920                 925
Ser Glu Leu Glu Asp Lys Tyr Lys Glu Tyr Lys Leu Asn Phe Tyr His
            930                 935                 940
Gly Lys Asn Glu Asp Phe Pro Ser Lys Leu Leu Arg Asp Ile Ile Glu
945                 950                 955                 960
Glu Asn Leu Ser Tyr Gly Ser Lys Glu Lys Ala Thr Asn Glu Arg
            965                 970                 975
```

-continued

```
Leu Val Glu Pro Leu Met Asn Leu Leu Lys Ser Tyr Glu Gly Gly Arg
            980                 985                 990

Glu Ser His Ala His Phe Val Val Lys Ser Leu Phe Glu Glu Tyr Leu
            995                 1000                1005

Thr Val Glu Glu Leu Phe Ser Asp Gly Ile Gln Ser Asp Val Ile Glu
            1010                1015                1020

Thr Leu Arg His Gln His Ser Lys Asp Leu Gln Lys Val Val Asp Ile
1025                1030                1035                1040

Val Leu Ser His Gln Gly Val Arg Asn Lys Ala Lys Leu Val Thr Ala
            1045                1050                1055

Leu Met Glu Lys Leu Val Tyr Pro Asn Pro Gly Gly Tyr Arg Asp Leu
            1060                1065                1070

Leu Val Arg Phe Ser Ser Leu Asn His Lys Arg Tyr Tyr Lys Leu Ala
            1075                1080                1085

Leu Lys Ala Ser Glu Leu Leu Glu Gln Thr Lys Leu Ser Glu Leu Arg
            1090                1095                1100

Ala Ser Val Ala Arg Ser Leu Ser Asp Leu Gly Met His Lys Gly Glu
1105                1110                1115                1120

Met Ser Ile Lys Asp Asn Met Glu Asp Leu Val Ser Ala Pro Leu Pro
            1125                1130                1135

Val Glu Asp Ala Leu Ile Ser Leu Phe Asp Tyr Ser Asp Arg Thr Val
            1140                1145                1150

Gln Gln Lys Val Ile Glu Thr Tyr Ile Ser Arg Leu Tyr Gln Pro His
            1155                1160                1165

Leu Val Lys Asp Ser Ile Gln Met Lys Phe Lys Glu Ser Gly Ala Ile
            1170                1175                1180

Thr Phe Trp Glu Phe Tyr Glu Gly His Val Asp Thr Arg Asn Gly His
1185                1190                1195                1200

Gly Ala Ile Ile Gly Gly Lys Arg Trp Gly Ala Met Val Val Leu Lys
            1205                1210                1215

Ser Leu Glu Ser Ala Ser Thr Ala Ile Val Ala Ala Leu Lys Asp Ser
            1220                1225                1230

Ala Gln Phe Asn Ser Ser Glu Gly Asn Met Met His Ile Ala Leu Leu
            1235                1240                1245

Ser Ala Glu Asn Glu Ser Asn Ile Ser Gly Ile Ser Ser Asp Asp Gln
            1250                1255                1260

Ala Gln His Lys Met Glu Lys Leu Ser Lys Ile Leu Lys Asp Thr Ser
1265                1270                1275                1280

Val Ala Ser Asp Leu Gln Ala Ala Gly Leu Lys Val Ile Ser Cys Ile
            1285                1290                1295

Val Gln Arg Asp Glu Ala Arg Met Pro Met Arg His Thr Phe Leu Trp
            1300                1305                1310

Leu Asp Asp Lys Ser Cys Tyr Glu Glu Glu Gln Ile Leu Arg His Val
            1315                1320                1325

Glu Pro Pro Leu Ser Thr Leu Leu Glu Leu Asp Lys Leu Lys Val Lys
            1330                1335                1340

Gly Tyr Asn Glu Met Lys Tyr Thr Pro Ser Arg Asp Arg Gln Trp His
1345                1350                1355                1360

Ile Tyr Thr Leu Arg Asn Thr Glu Asn Pro Lys Met Leu His Arg Val
            1365                1370                1375

Phe Phe Arg Thr Ile Val Arg Gln Pro Asn Ala Gly Asn Lys Phe Arg
            1380                1385                1390

Ser Ala Gln Ile Ser Asp Ala Glu Val Gly Cys Pro Glu Glu Ser Leu
```

-continued

```
            1395                1400                1405
Ser Phe Thr Ser Asn Ser Ile Leu Arg Ser Leu Met Thr Ala Ile Glu
    1410                1415                1420

Glu Leu Glu Leu His Ala Ile Arg Thr Gly His Ser His Met Tyr Leu
1425                1430                1435                1440

Cys Ile Leu Lys Glu Gln Lys Leu Leu Asp Leu Ile Pro Phe Ser Gly
                1445                1450                1455

Ser Thr Ile Val Asp Val Gly Gln Asp Glu Ala Thr Ala Cys Ser Leu
            1460                1465                1470

Leu Lys Ser Met Ala Leu Lys Ile His Glu Leu Val Gly Ala Arg Met
        1475                1480                1485

His His Leu Ser Val Cys Gln Trp Glu Val Lys Leu Lys Leu Asp Cys
    1490                1495                1500

Asp Gly Pro Ala Ser Gly Thr Trp Arg Val Val Thr Thr Asn Val Thr
1505                1510                1515                1520

Gly His Thr Cys Thr Ile Asp Ile Tyr Arg Glu Val Glu Glu Ile Glu
                1525                1530                1535

Ser Gln Lys Leu Val Tyr His Ser Ala Ser Ser Ala Gly Pro Leu
            1540                1545                1550

His Gly Val Ala Leu Asn Asn Pro Tyr Gln Pro Leu Ser Val Ile Asp
        1555                1560                1565

Leu Lys Arg Cys Ser Ala Arg Asn Asn Arg Thr Thr Tyr Cys Tyr Asp
    1570                1575                1580

Phe Pro Leu Ala Phe Glu Thr Ala Leu Gln Lys Ser Trp Gln Ser Asn
1585                1590                1595                1600

Gly Ser Thr Val Ser Glu Gly Asn Glu Asn Ser Lys Ser Tyr Val Lys
                1605                1610                1615

Ala Thr Glu Leu Val Phe Ala Glu Lys His Gly Ser Trp Gly Thr Pro
            1620                1625                1630

Ile Ile Pro Met Glu Arg Pro Ala Gly Leu Asn Asp Ile Gly Met Val
        1635                1640                1645

Ala Trp Ile Met Glu Met Ser Thr Pro Glu Phe Pro Asn Gly Arg Gln
    1650                1655                1660

Ile Ile Val Val Ala Asn Asp Ile Thr Phe Arg Ala Gly Ser Phe Gly
1665                1670                1675                1680

Pro Arg Glu Asp Ala Phe Phe Glu Thr Val Thr Asn Leu Ala Cys Glu
                1685                1690                1695

Arg Lys Leu Pro Leu Ile Tyr Leu Ala Ala Asn Ser Gly Ala Arg Ile
            1700                1705                1710

Gly Ile Ala Asp Glu Val Lys Ser Cys Phe Arg Val Gly Trp Ser Asp
        1715                1720                1725

Glu Gly Ser Pro Glu Arg Gly Phe Gln Tyr Ile Tyr Leu Thr Glu Glu
    1730                1735                1740

Asp Tyr Ala Arg Ile Ser Ser Val Ile Ala His Lys Leu Glu Leu
1745                1750                1755                1760

Asp Ser Gly Glu Ile Arg Trp Ile Ile Asp Ser Val Val Gly Lys Glu
                1765                1770                1775

Asp Gly Leu Gly Val Glu Asn Ile His Gly Ser Ala Ala Ile Ala Ser
            1780                1785                1790

Ala Tyr Ser Arg Ala Tyr Glu Glu Thr Phe Thr Leu Thr Phe Val Thr
        1795                1800                1805

Gly Arg Thr Val Gly Ile Gly Ala Tyr Leu Ala Arg Leu Gly Ile Arg
    1810                1815                1820
```

```
Cys Ile Gln Arg Leu Asp Gln Pro Ile Ile Leu Thr Gly Phe Ser Ala
1825                1830                1835                1840

Leu Asn Lys Leu Leu Gly Arg Glu Val Tyr Ser Ser His Met Gln Leu
           1845                1850                1855

Gly Gly Pro Lys Ile Met Ala Thr Asn Gly Val Val His Leu Thr Val
           1860                1865                1870

Pro Asp Val Leu Glu Gly Val Ser Asn Ile Leu Arg Trp Leu Ser Tyr
           1875                1880                1885

Val Pro Ala Asn Ile Gly Gly Pro Leu Pro Ile Thr Lys Pro Leu Asp
       1890                1895                1900

Pro Pro Asp Arg Pro Val Ala Tyr Ile Pro Glu Asn Thr Cys Asp Pro
1905                1910                1915                1920

Arg Ala Ala Ile Cys Gly Val Asp Asp Ser Gln Gly Lys Trp Leu Gly
               1925                1930                1935

Gly Met Phe Asp Lys Asp Ser Phe Val Glu Thr Phe Glu Gly Trp Ala
           1940                1945                1950

Lys Thr Val Val Thr Gly Arg Ala Lys Leu Gly Gly Ile Pro Val Gly
           1955                1960                1965

Val Ile Ala Val Glu Thr Gln Thr Met Met Gln Ile Ile Pro Ala Asp
       1970                1975                1980

Pro Gly Gln Leu Asp Ser His Glu Arg Ser Val Pro Arg Ala Gly Gln
1985                1990                1995                2000

Val Trp Phe Pro Asp Ser Ala Thr Lys Thr Ala Gln Ala Leu Leu Asp
               2005                2010                2015

Phe Asn Arg Glu Gly Leu Pro Leu Phe Ile Leu Ala Asn Trp Arg Gly
           2020                2025                2030

Phe Ser Gly Gly Gln Arg Asp Leu Phe Glu Gly Ile Leu Gln Ala Gly
           2035                2040                2045

Ser Thr Ile Val Glu Asn Leu Arg Thr Tyr Asn Gln Pro Ala Phe Val
       2050                2055                2060

Tyr Ile Pro Met Ala Gly Glu Leu Arg Gly Gly Ala Trp Val Val Val
2065                2070                2075                2080

Asp Ser Lys Ile Asn Pro Asp Arg Ile Glu Cys Tyr Ala Glu Arg Thr
           2085                2090                2095

Ala Lys Gly Asn Val Leu Glu Pro Gln Gly Leu Ile Glu Ile Lys Phe
           2100                2105                2110

Arg Ser Glu Glu Leu Gln Asp Cys Met Gly Arg Leu Asp Pro Glu Leu
           2115                2120                2125

Ile Asn Leu Lys Ala Lys Leu Gln Asp Val Asn His Gly Asn Gly Ser
           2130                2135                2140

Leu Pro Asp Ile Glu Gly Ile Arg Lys Ser Ile Glu Ala Arg Thr Lys
2145                2150                2155                2160

Gln Leu Leu Pro Leu Tyr Thr Gln Ile Ala Ile Arg Phe Ala Glu Leu
           2165                2170                2175

His Asp Thr Ser Leu Arg Met Ala Ala Lys Gly Val Ile Lys Lys Val
           2180                2185                2190

Val Asp Trp Glu Glu Ser Arg Ser Phe Phe Tyr Lys Arg Leu Arg Arg
           2195                2200                2205

Arg Ile Ala Glu Asp Val Leu Ala Lys Glu Ile Arg Gln Ile Val Gly
       2210                2215                2220

Asp Lys Phe Thr His Gln Leu Ala Met Glu Leu Ile Lys Glu Trp Tyr
2225                2230                2235                2240
```

```
Leu Ala Ser Gln Ala Thr Thr Gly Ser Thr Gly Trp Asp Asp Asp
                2245            2250                2255

Ala Phe Val Ala Trp Lys Asp Ser Pro Glu Asn Tyr Lys Gly His Ile
            2260            2265                2270

Gln Lys Leu Arg Ala Gln Lys Val Ser His Ser Leu Ser Asp Leu Ala
        2275            2280            2285

Asp Ser Ser Asp Leu Gln Ala Phe Ser Gln Gly Leu Ser Thr Leu
    2290            2295            2300

Leu Asp Lys Met Asp Pro Ser Gln Arg Ala Lys Phe Val Gln Glu Val
2305            2310            2315                2320

Lys Lys Val Leu Asp
            2325
```

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GGTCTTCAAT TGTGCTGTCT GG                                      22

(2) INFORMATION FOR SEQ ID NO: 8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

CCTTGACGAA CAGACTGGCT GTGC                                   24

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CACAGCCAGT CTGTTCGTCA AGG                                    23

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CCTCTACGTA ATTGGTCAGC                                        20

-continued (2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

CATAGCTATG GCAACTCCGG                                         20

METHODS AND AN ACETYL COA CARBOXYLASE GENE FOR CONFERRING HERBICIDE TOLERANCE AND AN ALTERATION IN OIL CONTENT OF PLANTS

CROSS-REFERENCE TO RELATED APPLICATIONS

This application is a continuation-in-part of patent application Ser. No. 08/014,326, filed Feb. 5, 1993, now U.S. Pat. No. 5,498,544.

STATEMENT OF GOVERNMENT RIGHTS

The present invention was made with the support of the United States Government via grants from the United States Department of Agriculture (Grant 92-37301-7852). The government has certain rights in the invention.

BACKGROUND OF THE INVENTION

Acetyl CoA carboxylase (ACCase) is an enzyme involved in many important metabolic pathways in plant, animal and bacterial cells. The enzyme is especially important in fatty acid synthesis in plants and is sensitive to inhibition by some types of herbicides. Structurally, ACCases are biotinylated and are quite large enzymes consisting of one or more subunits. For example, most ACCases of animals, higher plants, and yeast are dimers of 420 to 700 kD native MW and contain subunits of 200 to 280 kD. Diatom and algal ACCases are 700 to 740 kD tetramers of 160 to 180 kD subunits. Bacterial ACCase consists of three dissociable proteins; biotin carboxylase (51 kD), biotin carboxyl carrier protein (22.5 kD), and biotin transcarboxylase (130 kD).

Acetyl CoA Carboxylase (ACCase) catalyzes the formation of malonyl-CoA from acetyl-CoA and bicarbonate in animal, plant, and bacterial cells. Malonyl-CoA is an essential substrate for (i) de novo fatty acid (FA) synthesis, (ii) fatty acid elongation, (iii) synthesis of secondary metabolites such as flavonoids and anthocyanins, and (iv) malonylation of some amino acids and secondary metabolites. Synthesis of malonyl-CoA is the first committed step of flavonoid and fatty acid synthesis and current evidence suggests that ACCase catalyzes the rate-limiting step of fatty acid synthesis. Formation of malonyl-CoA by ACCase occurs via two partial reactions and requires a biotin prosthetic group:

(i) E-biotin+ATP+$HCO_3$→E-biotin-$CO_2$+ADP+Pi (ii) E-biotin-$CO_2$+Acetyl-CoA→E-biotin+malonyl-CoA
    (NET)Acetyl-CoA+ATP+$HCO_3$→malonyl-CoA+ADP+Pi In *E. coli*, these reactions are catalyzed by three distinct components; biotin carboxylase, biotin transcarboxylase, and biotin carboxyl carrier protein, which can be separated and yet retain partial activity. Plant and animal ACCases contain all three activities on a single polypeptide.

In plants, most ACCase activity is located in plastids of green and non-green plant tissues including leaves and oil seeds. Leaf ACCase activity is primarily located in mesophyll cells, but lesser amounts have been found in C-4 bundle sheath cells and in epidermal cells. The subcellular location of ACCase activity in epidermal cells is unknown, but since synthesis of very long-chain fatty acids (VLCFA) for formation of waxes, cutin, and suberin occurs on the endoplasmic reticulum (ER), malonyl-CoA might also be derived from a cytosolic ACCase. In contrast, rat ACCase is primarily cytosolic or associated with the outer mitochondrial membrane.

De novo fatty acid synthesis in chloroplasts involves successive 2-carbon additions to acetate, using malonate as the 2-C donor. All intermediates are attached to acyl carrier protein (ACP). Synthesis in plastids resembles that in *E. coli* in that the fatty acid synthesis complex can be dissociated into separate enzymes: β-ketoacyl-ACP synthase (KAS), β-ketoacyl-ACP reductase, β-hydroxyl-ACP dehydratase, and enoyl-ACP reductase, acetyl-CoA:ACP transacylase, and malonyl-CoA:ACP transacylase. A highly active KASIII isozyme catalyzes the condensation of acetyl-CoA and malonyl-ACP. Successive additions of malonyl-CoA to acyl-ACPs catalyzed by KAS I form C16 acyl-ACP, some of which is converted to C18 acyl-ACP by KAS II and then to C18:1-ACP. Fatty acid metabolism then diverges; de-esterification allows movement to the cytoplasm (eukaryotic path) where fatty acids may be further unsaturated and/or elongated by additions of malonyl-CoA in the ER. Alternatively, fatty acids are linked to glycerol-3-phosphate (prokaryotic path), further unsaturated, and used for synthesis of chloroplast lipids. A portion of cytoplasmic lipids returns to the chloroplast. The relative contributions of these two paths are species-specific but appear to be relatively flexible in mutants blocked in either path. In oil-storing organs such as cotyledons and monocot embryos, the triacylglycerides are stored in cytoplasmic oil bodies surrounded by a single unit membrane.

Condensation of malonyl-CoA with phenylpropionyl-CoAs or acetyl-CoA leads to synthesis of flavonoids, anthocyanins, or to polyacetates. Condensation is increased by light, elicitors, or pathogens and may be the rate-limiting step in synthesis of some phytoalexins. In addition to the secondary metabolites derived by de novo synthesis, malonyl conjugates of flavonoid glycosides, formed by malonyl-CoA:flavonoid glycoside malonyltransferase, D-amino acids and 1-amino-carboxyl-cyclopropane (ethylene precursor) are found in plants. Malonylated compounds accumulate in vacuoles, probably after synthesis in the cytoplasm.

An important property of ACCase is the central role it plays in fatty acid synthesis and accumulation in plants and seeds. Available evidence supports the idea that ACCase activity is the rate-limiting step for de novo fatty acid synthesis in plants. High rates of ACCase activity in vitro parallel or slightly precede high rates of lipid deposition or [$^{14}$C]acetate incorporation into lipids in developing leaves and oil seeds. Significant changes in plant ACCase activity occur during chloroplast development and increase in ACCase activity correlates with lipid deposition in developing oil seeds. Turnham et al., *Biochem. J.*, 212:223 (1883); and Post-Beittenmiller et al., *Plant Physiol.*, 100:923 (1992).

Among other properties, ACCase in most monocots is also inhibited by several herbicides. [$^{14}$C]acetate incorporation into maize lipids is strongly inhibited by fluazifop and sethoxydim due to inhibition of plastid ACCase. In barley, however, fluazifop had little effect on [$^{14}$C]acetate incorporation into very long-chain fatty acids. Since synthesis of very long-chain fatty acids occurs in the cytosol on the ER, and de novo fatty acid synthesis occurs in the plastids, cytosolic malonyl-CoA might be supplied by a herbicide insensitive ACCase isozyme.

There are three general mechanisms by which plants may be resistant to, or tolerant of, herbicides. These mechanisms include insensitivity at the site of action of the herbicide (usually an enzyme), rapid metabolism (conjugation or degradation) of the herbicide, or poor uptake and translocation of the herbicide. Altering the herbicide site of action from a sensitive to an insensitive form is the preferred method of conferring tolerance on a sensitive plant species. This is because tolerance of this nature is likely to be a dominant trait encoded by a single gene, and is likely to encompass whole families of compounds that share a single site of action, not just individual chemicals. Therefore, detailed information concerning the biochemical site and mechanism of herbicide action is of great importance and can be applied in two ways. First, the information can be used to develop cell selection strategies for the efficient identification and isolation of appropriate herbicide-tolerant variants. Second, it can be used to characterize the variant cell lines and regenerated plants that result from the selections.

Tissue culture methods have been used to select for resistance (or tolerance) using a variety of herbicides and plant species (see review by Meredith and Carlson, 1982, in *Herbicide Resistance in Plants*, eds. Lebaron and Gressel, pp. 275–291, John Wiley and Sons, N.Y.). For example, P. C. Anderson et al., in U.S. Pat. No. 4,761,373, disclose the use of tissue culture methods to produce maize plants resistant to herbicidal imidazolidones and sulfonamides. The resistance is due to the presence of altered acetohydroxy acid synthase which is resistant to deactivation by these herbicides.

Certain 1,3-cyclohexanediones exhibit general and selective herbicidal activity against plants. One such cyclohexanedione is sethoxydim {2-[1-(ethoxyimino)-butyl]-5-[2-(ethylthio)propyl]-3-hydroxy-2-cyclohexen-1-one }. Sethoxydim is commercially available from BASF (Parsippany, N.J.) under the designation POAST™.

Other herbicidal cyclohexanediones include clethodim, (E,E)-(±)-2-[1-[[(3-chloro-2-propenyl)oxy]imino]propyl]-5-[2-(ethylthio)propyl]-3-hydroxy-2-cyclohexen-1-one; available as SELECT™ from Chevron Chemical (Valent) (Fresno, Calif.); cloproxydim, (E,E)-2-[1-[[(3-chloro-2-propenyl)oxy]imino]butyl]-5-[2-(ethylthio)propyl]-3-hydroxy-2-cyclohexen-1-one; available as SELECTONE™ from Chevron Chemical (Valent) (Fresno, Calif.); and tralkoxydim, 2-[1-(ethoxyimino)propyl]-3-hydroxy-5-mesitylcyclohex-2-enone, available as GRASP™ from Dow Chemical USA (Midland, Mich.).

For purposes of reference in the present specification, the herbicides described in the two preceding paragraphs and other structurally related herbicidal compounds, are collectively referred to as the cyclohexanedione family of herbicides.

Certain aryloxyphenoxypropanoic acids exhibit general and selective herbicidal activity against plants. In these compounds, the aryloxy group may be phenoxy, pyridinyloxy or quinoxalinyl. One such herbicidal aryloxyphenoxypropanoic acid is haloxyfop, {2-[4-[[3-chloro-5-(trifluoromethyl)-2-pyridinylloxy]phenoxy]-propanoic acid}, which is available as VERDICT™ from Dow Chemical USA (Midland, Mich.). Another is diclofop, {(±)-2-[4-(2,4-dichlorophenoxy)-phenoxy]propanoic acid}, available as HOELON™ from Hoechst-Roussel Agri-Vet Company (Somerville, N.J.).

Other members of this family of herbicides include fenoxyaprop, (±)-2-[4-[(6-chloro-2-benzoxazolyl)oxy] phenoxy]propanoic acid; available as WHIP™ from Hoechst-Roussel Agri-Vet Company (Somerville, N.J.); fluazifop, (±)-2-[4-[[5-(trifluoromethyl)-2-pyridinyl]oxy] phenoxy]propanoic acid; available as FUSILADE™ from ICI Americas (Wilmington, Del.); fluazifop-P, (R)-2-[4-[[5-(trifluoromethyl)-2-pyridinyl]oxy]phenoxy]propanoic acid; available as FUSILADE 2000™ from ICI Americas (Wilmington, Del.); and quizalofop, (±)-2-[4[(6-chloro-2-quinoxalinyl)-oxy]phenoxy]propanoic acid; available as ASSURE™ from E. I. DuPont de Nemours (Wilmington, Del.).

For purposes of reference in the present specification, the herbicides referred to in the two preceding paragraphs and other structurally related herbicidal compounds, are collectively referred to as herbicidal aryloxyphenoxypropanoic acids.

Thus, there is a need for methods to develop plants that are resistant or tolerant to herbicides. There is also a need to increase the oil and/or fatty acid content of the plants and seeds, as well as for methods to increase their resistance to herbicides. There is a need to identify and clone genes important in conferring herbicide tolerance and in increasing the oil content of plants.

SUMMARY OF THE INVENTION

The present invention provides an isolated and purified DNA molecule comprising a DNA segment encoding a maize acetyl CoA carboxylase gene and methods for conferring herbicide tolerance and/or altering the oil content of plants by introducing and expressing a plant acetyl CoA carboxylase gene in the plant cells. The DNA molecule encoding a plant acetyl CoA carboxylase can encode an unaltered plant acetyl CoA carboxylase or an altered plant acetyl CoA carboxylase substantially tolerant to inhibition by cyclohexanedione or aryloxyphenoxypropanoic acid herbicides as well as encoding an antisense DNA sequence that is substantially complementary to a plant acetyl CoA carboxylase gene or to a portion thereof. A DNA molecule of the invention can also further comprise an amino terminal plant chloroplast transit peptide sequence operably linked to the maize acetyl CoA carboxylase gene.

The method of imparting cyclohexanedione or aryloxyphenoxypropanoic acid herbicide tolerance to a plant includes the steps of introducing a DNA molecule comprising a gene coding for a plant acetyl CoA carboxylase or an altered or a functional mutant thereof operably linked to a promoter functional in a plant cell into cells of a susceptible plant, and regenerating the transformed plant cells to provide a differentiated plant. The promoter can be an inducible or tissue specific promoter or provide for overexpression of at least about a 2-fold amount of a native plant acetyl CoA carboxylase. The functional linkage of a promoter to the DNA molecule results in an expression cassette. Expression of the DNA molecule is in an amount effective to render the acetyl CoA carboxylase and/or the plant tissue substantially tolerant to the herbicides relative to the native acetyl CoA carboxylase present in said plant. Herbicide tolerance can be achieved in the plants by at least two methods, including increasing the level of gene expression of a native or unaltered acetyl CoA carboxylase, or by introducing an altered gene coding for an acetyl CoA carboxylase that is less sensitive to herbicide inhibition. The level of gene expression can be increased by either combining a plant acetyl CoA carboxylase gene with a promoter that provides for a high level of gene expression, such as a 35S cauliflower mosaic virus promoter (CaMV), or by introducing multiple copies of the gene into the cell so that the multiple copies of the gene are integrated into the genome of transformed plant cells. The preferred plant cells into which to introduce the expression cassette of the invention, to achieve herbicide tolerance, are monocot plant cells. Once transformed cells exhibiting herbicide tolerance are obtained, transgenic plants and seeds can then be regenerated therefrom, and evaluated for stability of the inheritance of the herbicide tolerance trait.

The invention also provides a method for altering, preferably raising, the oil content in a plant. The method includes the steps of introducing a DNA molecule comprising a gene coding for a plant acetyl CoA carboxylase or an altered or a functional mutant thereof operably linked to a promoter functional in a plant cell into the cells of plant tissue and expressing the gene in an amount effective to alter the oil content of the plant cell. An alteration in oil content can include a change in total oil content over that normally present in that type of plant cell or a change in the type of oil present in the cell. An alteration in oil content in the plant cell, according to the method of the invention, can be achieved by at least two methods including:

(1) an increase or decrease in expression of an altered plant acetyl CoA carboxylase gene; or (2) by introducing an altered or functional mutant plant acetyl CoA carboxylase gene.

The level of gene expression of an unaltered plant acetyl CoA carboxylase gene can be increased by either combining an unaltered plant acetyl CoA carboxylase with a promoter that provides for a high level of gene expression, or by introducing multiple copies of an expression cassette into cells so that multiple copies of the gene are integrated into the genome. When an altered or a functional mutant plant acetyl CoA carboxylase gene codes for an enzyme that exhibits an increase in specific activity, it can lead to an increase in total oil content of the plant cell. When an altered or a functional mutant acetyl CoA carboxylase gene codes for an enzyme having a decrease in specific activity, it may lead to a decrease in the total oil content of the plant cell. Preferably, the expression cassette is introduced into dicot plants such as soybeans, canola, and sunflower. In an especially preferred version, transformed cells exhibiting about a 1.2- to 5-fold increase in total oil content and/or expression or specific activity of acetyl CoA carboxylase are selected for and used to generate transgenic plants and seeds exhibiting a substantial increase in oil content. A substantial increase in oil content depends on the oil content normally present in the plant or seed and can range from about a 1.2 to a 20-fold increase.

The invention also provides for a method of producing plant acetyl CoA carboxylase in a host cell. The method includes the steps of introducing an expression cassette comprising a gene encoding a plant acetyl CoA carboxylase or an altered or a functional plant acetyl CoA carboxylase into a host cell and expressing the gene in an amount sufficient to permit crystallization of the plant acetyl CoA carboxylase. An expression cassette can include a promoter that is functional in either a eukaryotic or a prokaryotic cell. Preferably, the expression cassette is introduced into a prokaryotic cell, such as *E. coli*, that is routinely used for production of recombinantly produced proteins. Recombinantly produced and crystallized plant acetyl CoA carboxylase can then be used to identify other herbicides and that bind to and inhibit acetyl CoA carboxylase in plants. In addition, the availability of large amounts of purified enzyme can permit the screening of the efficacy of such herbicides in terms of their ability to bind to, or otherwise inhibit, the activity of the enzyme.

The present invention also provides an isolated and purified DNA molecule of at least seven nucleotide bases which hybridizes under high stringency conditions to a DNA molecule comprising a DNA segment encoding a plant acetyl CoA carboxylase and provides a hybridization probe comprising an isolated and purified DNA molecule of at least seven nucleotide bases, which is detectably labeled or which binds to a detectable label, which DNA molecule hybridizes under high stringency conditions to the non-coding strand of a DNA molecule comprising a DNA segment encoding a plant acetyl CoA carboxylase. High stringency conditions are defined as: hybridization at 65° C. for at least 16 hours in 5×SSC, 1× Denhardt's solution, 50 mM Tris-HCl, pH 8, 0.2% SDS, 10 mM EDTA, 0.1 mg/ml salmon sperm DNA, followed by washing twice for 5 minutes in 2× SSC, 0.5% SDS at 25° C., once for 10 minutes in 0.2× SSC, 0.1% SDS at 25° C. and twice for 30 minutes in 0.2× SSC, 0.1% SDS at 65° C.

The present invention also provides a method of introducing an exogenous plant acetyl CoA carboxylase gene into a host cell comprising transforming host cells in vitro with an expression cassette comprising a DNA molecule encoding a plant acetyl CoA carboxylase gene operably linked to a promoter functional in the host cell, expanding the transformed host cells in vitro, and identifying a transformed host cell which expresses the DNA molecule.

The term "consists essentially of" as used with respect to the present DNA molecules is defined to mean that a major portion of the nucleotide sequence encodes an ACCase, and that nucleotide sequences are not present which encode proteins other than ACCase or functional equivalents thereof.

BRIEF DESCRIPTION OF THE FIGURES

FIG. 2 is a graph depicting the effect of sethoxydim on the growth of mutant maize callus.

FIG. 3 is a graph depicting the shoot length growth of maize seedlings seven days after treatment with sethoxydim.

FIG. 4 is a graph depicting the shoot length growth of maize seedlings fourteen days after treatment with sethoxydim.

FIG. 9: Northern blot of total RNA from leaf, immature embryo and endosperm tissue (16 days after pollination), and Black Mexican Sweet corn (BMS) cells. Lanes contain 10 μg total RNA and were probed with the 2 kb EcoRI fragment of lambda clone #15-14.

FIG. 10: DNA sequence (SEQ ID NO. 1) of a 2 kb EcoRI fragment of lambda clone #15-14 including a portion of a maize ACCase gene located at bases 2883 to 83 from the 3' stop codon.

FIG. 13: DNA sequence (SEQ ID NO:5) of a 7470 base pair cDNA of a maize ACCase gene. (Genbank Accession No. U19183).

FIG. 14: Predicted amino acid sequence of the complete ACCase gene of maize (SEQ ID NO:6).

DETAILED DESCRIPTION OF THE INVENTION

Figure 1:
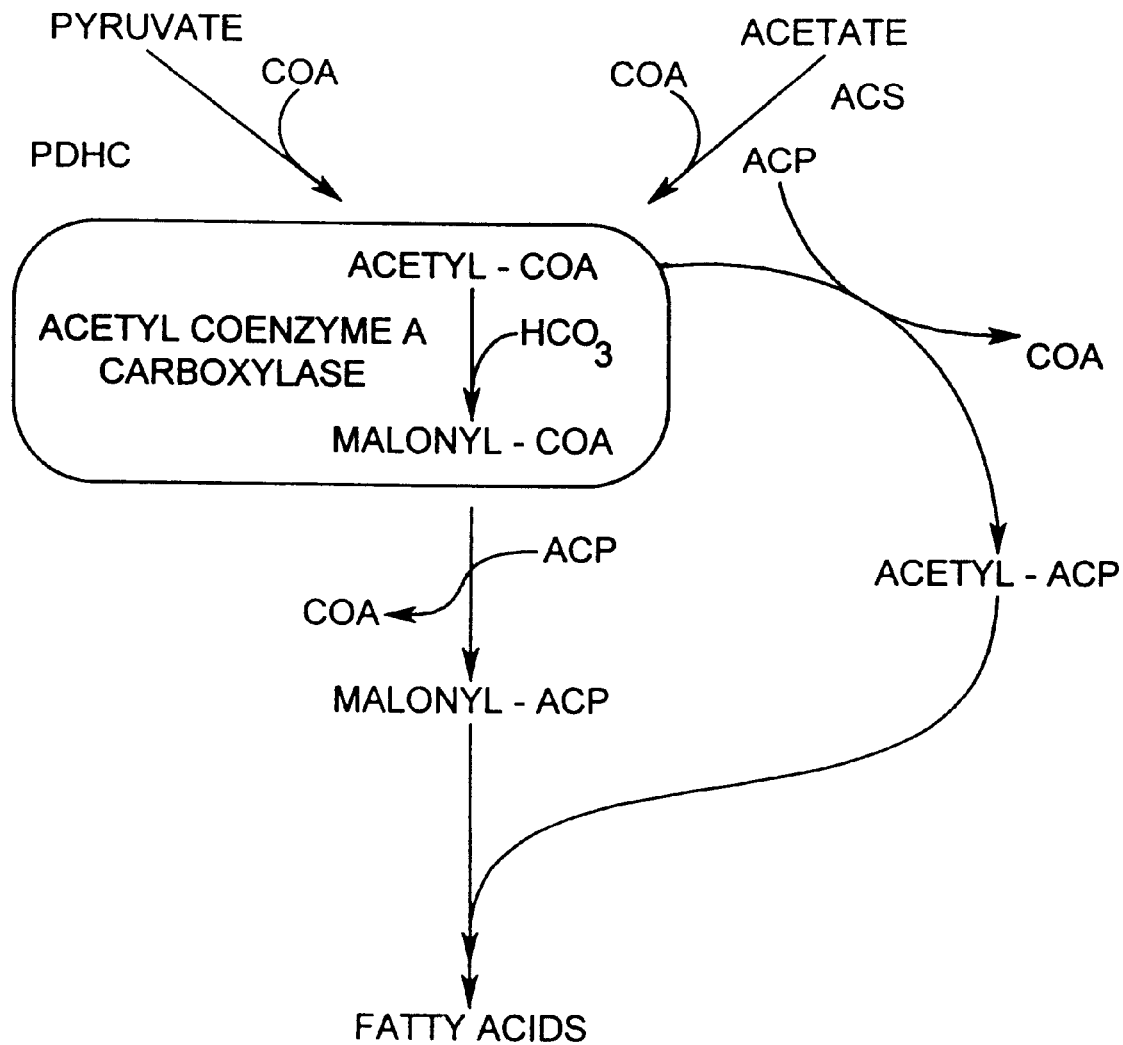
FIG. 1 is a schematic depiction of the fatty acid biosynthesis pathway in plants.

The present invention provides a DNA molecule encoding a plant acetyl CoA carboxylase gene and methods for conferring herbicide tolerance and/or altering the oil content of plants by introducing and expressing a plant acetyl CoA carboxylase gene in the plant cells. In plants, acetyl CoA carboxylase plays a central role in regulating fatty acid synthesis and in the sensitivity of monocots to cyclohexanedione or aryloxyphenoxypropanoic acid herbicides.

In accord with the present invention, a plant acetyl CoA carboxylase gene is identified, isolated and combined with a promoter functional in a plant cell to provide a recombinant expression cassette. A plant acetyl CoA carboxylase gene can be introduced and expressed in a plant cell. Depending on the type of plant cell, the level of gene expression, and the activity of the enzyme encoded by the gene, introduction of a plant acetyl CoA carboxylase gene into the plant cell can confer herbicide tolerance and/or alteration of the oil of the plant cell.

In monocots, an exogenously introduced plant acetyl CoA carboxylase gene can be expressed at a level effective to render the cells of the plant tissue substantially tolerant to cyclohexanedione or aryloxyphenoxypropanoic acid herbicide levels which normally inhibit a native or endogenous acetyl CoA carboxylase. A native acetyl CoA carboxylase is an enzyme that is normally encoded and expressed in the plant cell prior to transformation. An exogenously introduced plant acetyl CoA carboxylase gene is a gene which has been isolated and amplified from either the same or different type of cell. Exogenous introduction and expression of a plant acetyl CoA carboxylase gene in both monocots and dicots can result in alteration of the oil content and quality of plant tissue and seeds. Exogenous introduction and expression in a host cell, such as a bacteria, can provide for sufficient amounts of plant acetyl CoA carboxylase to allow for crystallization and isolation of the enzyme. Crystallized plant acetyl CoA carboxylase is useful to identify other herbicides that bind to and can inhibit plant acetyl CoA carboxylases. The enzyme could also be used to screen potential herbicidal compounds for efficacy.

A. Formation of an Expression Cassette

An expression cassette of the invention can comprise a DNA molecule encoding a plant acetyl CoA carboxylase gene or an altered or functional mutant thereof operably linked to a promoter functional in a plant cell. The gene can code for a plant acetyl CoA carboxylase that is substantially tolerant to herbicides, preferably cyclohexanedione and/or aryloxyphenoxypropanoic acid herbicides. An expression cassette of the invention can also include an antisense DNA sequence that is substantially complementary to an acetyl CoA carboxylase gene or a portion thereof operably linked to a promoter functional in a plant cell.

1. Isolation and Identification of a Gene Coding for a Plant Acetyl CoA Carboxylase A gene encoding a plant acetyl CoA carboxylase can be identified and isolated by standard methods, as described by Sambrook et al., *Guide to Molecular Cloning: A Laboratory Manual*, Cold Spring Harbor, N.Y. (1989). The gene can be obtained either from monocot or dicot plant cells. When the gene encoding a plant acetyl CoA carboxylase is obtained from a dicot plant, the enzyme encoded by the gene exhibits tolerance to cyclohexanedione or aryloxyphenoxypropanoic acid herbicides. The gene can also be obtained from herbicide-tolerant maize cell lines, prepared as described in U.S. Pat. No. 5,162,602, which is hereby incorporated by reference.

A gene encoding a plant acetyl CoA carboxylase can be identified by screening of a DNA or cDNA library generated from plant cells. Screening for DNA fragments that encode all or a portion of the gene encoding a plant acetyl CoA carboxylase can be accomplished by complementation of an auxotrophic mutant of acetyl CoA carboxylase in *E. coli* (fabE) (Bachman, Microbiological Reviews, 47:180 (1983)) or yeast (accl) (Michionada, *Eur. J. Biochem.*, 111:79 (1980)) or by screening of plaques for binding to antibodies that specifically recognize a plant acetyl CoA carboxylase. DNA fragments that can restore ACCase activity in *E. coli* or yeast and/or plaques carrying DNA fragments that are immunoreactive with antibodies to a plant ACCase can be subcloned into a vector and sequenced and/or used as probes to identify other cDNA or genomic sequences encoding all or a portion of a plant acetyl CoA carboxylase gene.

Specific examples of cDNA sequences encoding a portion of a plant acetyl CoA carboxylase gene include DNA fragments that include a DNA sequence that substantially corresponds to the coding sequence for the transcarboxylase active site of a plant acetyl CoA carboxylase, DNA fragments that include a DNA sequence that substantially corresponds to a coding sequence for the biotin binding site of a plant acetyl CoA carboxylase, a DNA fragment encoding the 5' transcriptional start sequence of a plant acetyl CoA carboxylase gene, and a DNA fragment encoding the 3' transcriptional stop sequence for the acetyl CoA carboxylase gene. Substantially corresponding DNA sequences share about 90% to about 100% DNA sequence homology. Especially preferred cDNA probes can be obtained from lambda clone #18-5 which include DNA sequences corresponding to the transcarboxylase active site domain and the biotin binding site domain. Lambda clone #18-5 includes EcoRI subclones of 3.9 kb, 1.2 kb, or 0.23 kb. Lambda subclone #18-51 is an 3.9 kb EcoRI subclone. The lambda subclone #18-51 has been deposited with the American Type Culture Collection, Rockville, Md., and given Accession No. 69236.

In a preferred version, a plant acetyl CoA carboxylase gene is identified and isolated from an herbicide tolerant maize cell line prepared as described in Example II. A cDNA library can be prepared by oligo dT priming. Plaques containing DNA fragments can be screened with antibodies specific for maize acetyl CoA carboxylase. DNA fragments encoding a portion of an acetyl CoA carboxylase gene can be subcloned and sequenced and used as probes to identify a genomic acetyl CoA carboxylase gene. DNA fragments encoding a portion of a maize acetyl CoA carboxylase can be verified by determining sequence homology with other known acetyl CoA carboxylases, such as chicken or yeast acetyl CoA carboxylase, or by hybridization to acetyl CoA carboxylase specific messenger RNA. Once DNA fragments encoding portions of the 5', middle and 3' ends as well as the transcarboxylase active site or biotin binding site of a plant acetyl CoA carboxylase are obtained, they can be used to identify and clone a complete genomic copy of a maize acetyl CoA carboxylase gene.

To isolate a complete copy of a maize acetyl CoA carboxylase gene, a maize genomic library can then be probed with cDNA probes prepared as described above. Portions of the genomic copy or copies of a plant acetyl CoA carboxylase gene can be sequenced and the 5' end of the gene are identified by standard methods including either DNA sequence homology to other acetyl CoA carboxylase genes or by RNAase protection analysis, as described by Sambrook et al., *Molecular Cloning: A Laboratory Manual*, Cold Spring Harbor Press, Cold Spring Harbor, N.Y. (1989). Once portions of the 5' end of the gene are identified, complete copies of a plant acetyl CoA carboxylase gene can be obtained by standard methods, including by cloning or by polymerase chain reaction (PCR) synthesis using oligonucleotide primers complementary to the DNA sequence at the 5' end of the gene. The presence of an isolated full-length copy of a plant acetyl CoA carboxylase gene can be verified by hybridization, partial sequence analysis, or by expression of a plant acetyl CoA carboxylase enzyme. The maize acetyl CoA carboxylase gene cloned and expressed from a maize herbicide tolerant cell line can be assessed for tolerance to cyclohexanedione or aryloxyphenoxypropanoic acid herbicides by standard methods, as described in Example I.

An expression cassette of the invention can also contain an antisense DNA sequence. A antisense DNA sequence is a sequence that is substantially complementary to all or a portion of a coding sequence of a plant acetyl CoA carboxylase gene. A substantially complementary sequence has about 90% to about 100% DNA sequence homology with that of the coding sequence of all or a portion of a plant acetyl CoA carboxylase. The antisense DNA sequence when expressed can act to inhibit the synthesis and expression of a native plant acetyl CoA carboxylase. Antisense sequences are preferably about 200 to 1000 nucleotides long in order to provide sufficient inhibition of synthesis and/or expression of a native acetyl CoA carboxylase. The inhibition of acetyl CoA carboxylase synthesis and gene expression by antisense DNA sequences can be confirmed in a transformed plant cell by standard methods for measuring the presence and/or activity of the enzyme such as described in Examples I and V.

An expression cassette of the invention can also include a functional mutant of a plant acetyl CoA carboxylase gene. Mutants of a plant acetyl CoA carboxylase gene are substantially homologous to a plant acetyl CoA carboxylase gene and are functional if the acetyl CoA carboxylase expressed retains significant enzyme activity. A mutant substantially homologous to a plant acetyl CoA carboxylase can share about 90% to 99.99% DNA sequence with that gene. For example, a mutant acetyl CoA carboxylase gene can code for a herbicide tolerant acetyl CoA carboxylase, or for an acetyl CoA carboxylase with altered substrate specificity so that the total amount of oil content in the plants or seeds is increased, or for an enzyme with an altered substrate specificity so that synthesis of secondary metabolites such as flavonoids or anthocyanins is decreased. A preferred mutant is a gene coding for an acetyl CoA carboxylase that is substantially tolerant to cyclohexanedione or aryloxyphenoxypropanoic acid herbicide.

Altered or functional mutants of a gene coding for a plant acetyl CoA carboxylase can be obtained by several methods. The alteration or mutation of the ACCase gene can be accomplished by a variety of means including, but not limited to, the following methods.

1. spontaneous variation and direct mutant selection in cultures;
2. direct or indirect mutagenesis procedures on tissue culture of all cell types, seeds or plants; and
3. mutation of the cloned acetyl CoA carboxylase gene by methods such as site specific mutagenesis (Sambrook et al. cited supra), transposon mediated mutagenesis (Berg et al., *Biotechnology*, 1:417 (1983)) and deletion mutagenesis (Mitra et al., *Molec. Gen. Genetic.*, 215:294 (1989)).

Mutants can be identified by a change in a functional activity of the enzyme encoded by the gene or by detecting a change in the DNA sequence using restriction enzyme mapping or partial sequence analysis.

In a preferred version, a functional mutant gene encoding for a plant acetyl CoA carboxylase tolerant to cyclohexanedione and/or aryloxyphenoxypropanoic acid herbicides is isolated from a maize herbicide tolerant cell line. The maize herbicide tolerant cell line was obtained as described in U.S. Pat. No. 5,162,602, issued Nov. 10, 1992, the disclosure of which is incorporated by reference herein, and in Examples I–III. Briefly, partially differentiated cell cultures are grown and subcultured with continuous exposures to low herbicide levels. Herbicide concentrations are then gradually increased over several subculture intervals. Maize cells or tissues growing in the presence of normally toxic herbicide levels are repeatedly subcultured in the presence of the herbicide and characterized. Stability of the herbicide tolerance trait of the cultured cells may be evaluated by growing the selected cell lines in the absence of herbicides for various periods of time and then analyzing growth after exposing the tissue to herbicide.

Maize cell lines which are tolerant by virtue of having an altered acetyl CoA carboxylase enzyme can be selected by identifying cell lines having enzyme activity in the presence of normally toxic levels of sethoxydim or haloxyfop. The tolerant maize cells can be further evaluated for whether acetyl CoA carboxylase is altered to a less sensitive form or increased in its level of expression.

Maize cell lines with a acetyl CoA carboxylase less sensitive to herbicide inhibition can be used to isolate a functional mutant gene of a plant acetyl CoA carboxylase. A DNA library from a maize cell line tolerant to herbicides can be generated and DNA fragments encoding all or a portion of an acetyl CoA carboxylase gene can be identified by hybridization to a cDNA probe encoding a portion of the maize ACCase gene. A complete copy of the altered gene can be obtained either by cloning and ligation or by PCR synthesis using appropriate primers. The isolation of the altered gene coding for acetyl CoA carboxylase can be confirmed in transformed plant cells by determining whether the acetyl CoA carboxylase being expressed retains enzyme activity when exposed to normally toxic levels of herbicides.

2. Promoters

Once a plant acetyl CoA carboxylase gene or functional mutant thereof or an antisense DNA sequence is obtained and amplified, it is combined with a promoter functional in a plant cell to form an expression cassette.

Most genes have regions of DNA sequence that are known as promoters and which regulate gene expression. Promoter regions are typically found in the flanking DNA sequence upstream from the coding sequence in both pro-caryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous genes, that is a gene different from the native or homologous gene. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous genes is advantageous because it provides for a sufficient level of gene expression to allow for easy detection and selection of transformed cells and provides for a high level of gene expression when desired.

The promoter in an expression cassette of the invention can provide for overexpression of acetyl CoA of a plant acetyl CoA carboxylase gene or functional mutant thereof. Overexpression of the gene is that amount of gene expression that results in an increase in tolerance of the plant cells to an herbicide or that results in an increase in the total oil content of the cells. Overexpression of an acetyl CoA carboxylase gene is preferably about a 2- to 20-fold increase in expression of an acetyl CoA carboxylase over the expression level of the native acetyl CoA carboxylase. The promoter can also be inducible so that gene expression can be turned on or off by an exogenously added agent. For example, a bacterial promoter such as the $P_{tac}$ promoter can be induced to varying levels of gene expression depending on the level of isothiopropylgalactoside added to the transformed bacterial cells. It may also be preferable to combine the gene with a promoter that provides tissue specific expression or developmentally regulated gene expression in plants.

Specific promoters functional in plant cells include the 35S cauliflower mosaic virus promoter, nopaline synthase (NOS) promoter and the like. Currently, a preferred promoter for expression in monocots is the 35S cauliflower mosaic virus promoter.

An acetyl CoA carboxylase gene can be combined with the promoter by standard methods as described in Sambrook cited supra. Briefly, a plasmid containing a promoter such as the 35S cauliflower mosaic virus promoter can be constructed as described in Jefferson, *Plant Molecular Biology Reporter*, 5,387 (1987) or obtained from Clontech Lab in Palo Alto, Calif. (e.g. pBI21 or pBI221). Typically these plasmids are constructed to provide for multiple cloning sites having specificity for different restriction enzymes downstream from the promoter. A gene for plant acetyl CoA carboxylase can be subcloned downstream from the promoter using restriction enzymes to ensure that the gene is inserted in proper orientation with respect to the promoter so that the gene can be expressed. In a preferred version, a maize acetyl CoA carboxylase is operably linked to a 35 S CaMV promoter in a plasmid such as pBI121 or pBI221. Once a plant acetyl CoA carboxylase gene is operably linked to a promoter and the plasmid, the expression cassette so formed can be subcloned into other plasmids or vectors.

3. Optional Sequences in the Expression Cassette

The expression cassette can also optionally contain other DNA sequences. The expression cassette can further be comprised of a chloroplast transit peptide sequence operably linked between a promoter and a plant acetyl CoA carboxylase gene. If the expression cassette is to be introduced into a plant cell, the expression cassette can also contain plant transcriptional termination and polyadenylation signals and translational signals linked to the 3' terminus of a plant acetyl CoA carboxylase gene. The expression cassette can also optionally be further comprised of a plasmid.

Because one site of action for biosynthetic pathways involving plant acetyl CoA carboxylase is the chloroplast, an expression cassette of the invention can be combined with an exogenous DNA sequence coding for a chloroplast transit peptide, if necessary. An exogenous chloroplast transit peptide is one which is not encoded within the plant acetyl CoA carboxylase gene. A chloroplast transit peptide is typically 40 to 70 amino acids in length and functions post-translationally to direct the protein to the chloroplast. The transit peptide is cleaved either during or just after import into the chloroplast to yield the mature protein. The complete copy of a gene encoding a plant acetyl CoA carboxylase may contain a chloroplast transit peptide sequence. In that case, it may not be necessary to combine an exogenously obtained chloroplast transit peptide sequence into the expression cassette.

Exogenous chloroplast transit peptide encoding sequences can be obtained from a variety of plant nuclear genes, so long as the products of the genes are expressed as preproteins comprising an amino terminal transit peptide and transported into chloroplast. Examples of plant gene products known to include such transit peptide sequences are the small subunit of ribulose biphosphate carboxylase, ferredoxin, chlorophyll a/b binding protein, chloroplast ribosomal proteins encoded by nuclear genes, certain heatshock proteins, amino acid biosynthetic enzymes such as acetohydroxy acid synthase, 3-enolpyruvylphosphoshikimate synthase, dihydrodipicolinate synthase, and the like. Alternatively, the DNA fragment coding for the transit peptide may be chemically synthesized either wholly or in part from the known sequences of transit peptides such as those listed above.

Regardless of the source of the DNA fragment coding for the transit peptide, it should include a translation initiation codon and an amino acid sequence that is recognized by and will function properly in chloroplasts of the host plant. Attention should also be given to the amino acid sequence at the junction between the transit peptide and the plant acetyl CoA carboxylase enzyme where it is cleaved to yield the mature enzyme. Certain conserved amino acid sequences have been identified and may serve as a guideline. Precise fusion of the transit peptide coding sequence with the acetyl CoA carboxylase coding sequence may require manipulation of one or both DNA sequences to introduce, for example, a convenient restriction site. This may be accomplished by methods including site directed mutagenesis, insertion of chemically synthesized oligonucleotide linkers and the like.

Once obtained, the chloroplast transit peptide sequence can be appropriately linked to the promoter and a plant acetyl CoA carboxylase gene in an expression cassette using standard methods. Briefly, a plasmid containing a promoter functional in plant cells and having multiple cloning sites downstream can be constructed as described in Jefferson cited supra. The chloroplast transit peptide sequence can be inserted downstream from the promoter using restriction enzymes. A plant acetyl CoA carboxylase gene can then be inserted immediately downstream from and in frame with the 3' terminus of the chloroplast transit peptide sequence so that the chloroplast transit peptide is linked to the amino terminus of the plant acetyl CoA carboxylase. Once formed, the expression cassette can be subcloned into other plasmids or vectors.

When the expression cassette is to be introduced into a plant cell, the expression cassette can also optionally include 3' nontransiated plant regulatory DNA sequences. The 3' nontranslated regulatory DNA sequence preferably includes from about 300 to 1,000 nucleotide base pairs and contains plant transcriptional and translational termination sequence. Specific examples of 3' nontranslated regulatory DNA sequences functional in plant cells include about 500 base pairs of the 3' flanking DNA sequence of the pea ribulose biphosphate carboxylase small subunit E9 gene, the 3' flanking DNA sequence of the octopine synthase gene, and the 3' flanking DNA sequence of the nopaline synthase gene. These 3' nontranslated regulatory sequences can be obtained as described in An, *Methods in Enzymology*, 153:292 (1987) or are already present in plasmids available from commercial sources such as Clontech, Palo Alto, Calif. The 3' nontranslated regulatory sequences can be operably linked to the 3' terminus of a plant acetyl CoA carboxylase gene by standard methods.

An expression cassette of the invention can also be further comprised of a plasmid. Plasmid vectors included additional DNA sequences that provide for easy selection, amplification and transformation of the expression cassette in procaryotic and eukaryotic cells. The additional DNA sequences include origins of replication to provide for autonomous replication of the vector, selectable marker genes, preferably encoding antibiotic resistance, unique multiple cloning sites providing for multiple sites to insert DNA sequences or genes encoded in the expression cassette, and sequences that enhance transformation of prokaryotic and eukaryotic cells. The preferred vectors of the invention are plasmid vectors. The especially preferred vector is the pBI121 or pBI221 vector formed as described by Jefferson cited supra.

Another vector that is useful for expression in both plant and procaryotic cells is the binary Ti vector PGA582. This binary Ti vector has been previously characterized by An, cited supra., and is available from Dr. An. This binary Ti vector can be replicated in procaryotic bacteria such as *E. coli* and Agrobacterium. The Agrobacterium plasmid vectors can be used to transfer the expression cassette to plant cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform plant cells.

B. Method for Screening for Expression and/or Overexpression of a Plant Acetyl CoA Carboxylase Gene A method for screening for expression or overexpression of a plant acetyl CoA carboxylase gene is also provided by the invention. Once formed, an expression cassette comprising an acetyl CoA carboxylase gene can be subcloned into a known expression vector. The screening method in the invention includes the steps of introducing an expression vector into a host cell and detecting and/or quantitating expression of a plant acetyl CoA carboxylase gene. This method of screening is useful to identify expression cassettes providing for an overexpression of a plant acetyl CoA carboxylase gene, antisense molecules that effectively inhibit acetyl CoA carboxylase synthesis, and expression of an acetyl CoA carboxylase in the chloroplast of a transformed plant cell.

Suitable known expression vectors include plasmids that autonomously replicate in prokaryotic and eukaryotic cells. Specific examples include plasmids such as the pBI121 or pBI221 plasmid constructed as described by Jefferson cited supra, a binary Ti vector such as PG582 as described by An cited supra, PUC119, or PBR322. The preferred expression system is a pBI121 or pBI221 plasmid.

An expression cassette of the invention can be subcloned into an expression vector by standard methods. The expression vector can then be introduced into prokaryotic or eukaryotic cells by standard methods including protoplast transformation, Agrobacterium mediated transformation, electroporation, microprojectiles and liposomes. The expression vector can be introduced into plant cells such as tobacco, Brassica, Black Mexican sweet corn, and Arabidopsis cells. The vector can also be introduced into procaryotic cells such as *E. coli* or Agrobacterium. Transformed cells can be selected typically using a selection marker encoded on the expression vector.

Transient expression of a plant acetyl CoA carboxylase gene can be detected and quantitated in the transformed cells. Gene expression can be quantitated by a quantitative Western blot using antibodies specific for the cloned acetyl CoA carboxylase or by detecting an increase in specific activity of the enzyme. The tissue and subcellular location of the cloned acetyl CoA carboxylase can be determined by immunochemical staining methods using antibodies specific for the cloned acetyl CoA carboxylase. Sensitivity of the cloned acetyl CoA carboxylase to herbicides can also be assessed. Expression cassettes providing for overexpression of a plant acetyl CoA carboxylase or acetyl CoA carboxylase tolerant to herbicides can then be used to transform monocot and/or dicot plant tissue cells and to regenerate transformed plants and seeds.

C. Method of Imparting Cyclohexanedione or Aryloxyphenoxypropanoic Acid Herbicide Tolerance to a Plant The invention provides a method of conferring cyclohexanedione or aryloxyphenoxypropanoic acid herbicide tolerance to a plant. The method includes the steps of introducing an expression cassette comprising a gene coding for a plant acetyl CoA carboxylase or a functional mutant thereof operably linked to a promoter into the cells of plant tissue and expressing the gene in an amount effective to render the cells of the plant tissue substantially tolerant to herbicides. An effective amount of gene expression to render the cells of the plant tissue substantially tolerant to the herbicide depends on whether the gene codes for an unaltered acetyl CoA carboxylase gene or a mutant or altered form of the gene that is less sensitive to the herbicides. Expression of an unaltered plant acetyl CoA carboxylase gene in an effective amount is that amount that provides for a 2- to 50-fold increase in herbicide tolerance and preferably increases the amount of acetyl CoA carboxylase from at least about 2- to 20-fold over that amount of the native enzyme. An altered form of the enzyme can be expressed at levels comparable to that of the native enzyme or less if the altered form of the enzyme has higher specific activity. Acetyl CoA carboxylase substantially tolerant to herbicides is an enzyme that is tolerant of levels of herbicide which normally inhibit a native acetyl CoA carboxylase and preferably can function in concentrations of herbicide of about 2- to 20-fold greater than are toxic to the native enzyme.

Herbicide tolerance can be achieved by at least two methods including: 1) by increasing the level of gene expression of a native or unaltered acetyl CoA carboxylase gene; or 2) by introducing an altered gene coding for an acetyl CoA carboxylase that is less sensitive to herbicide inhibition. The level of gene expression can be increased by either combining a plant acetyl CoA carboxylase gene with a promoter that provides for a high level of gene expression such as the 35S CaMV promoter or by introducing the gene into the cells so that multiple copies of the gene are integrated into the genome of the transformed plant cell. Formation of an expression cassette comprised of a plant acetyl CoA carboxylase gene operably linked to a promoter that can be expressed in an effective amount to confer herbicide tolerance has been described previously.

Most monocots, but not dicots, are sensitive to cyclohexanedione and/or aryloxyphenoxypropanoic acid herbicides. The preferred plant cells for introducing an expression cassette of the invention to achieve herbicide tolerance for the plant cells then are monocot plants. Monocot plants include corn, wheat, barley, sorghum, rice, and others. An expression cassette of the invention can be introduced by methods of transformation, especially effective for monocots including biolistic transformation of Type II embryogenic suspension cells as described by W. J. Gordon-Kamm et al., *Plant Cell*, 2, 603–618 (1990), M. E. Fromm et al., *Bio/Technology*, 8, 833–839 (1990) and D. A. Walters et al., *Plant Molecular Biology*, 18, 189–200 (1992) or by electroporation of type I embryogenic calluses described by D'Hafluin et al., *The Plant Cell*, 4, 1495 (1992). Transformed cells can be selected for the presence of a selectable marker gene. Transient expression of a plant acetyl CoA carboxylase gene can be detected in the transgenic embryogenic calli using antibodies specific for the cloned plant acetyl CoA carboxylase. Transformed embryogenic calli can be used to generate transgenic plants that exhibit stable inheritance of either the altered acetyl CoA carboxylase gene or overexpression of the acetyl CoA carboxylase gene. Maize cell lines exhibiting satisfactory levels of tolerance to herbicide are put through a plant regeneration protocol to obtain mature maize plants and seeds expressing the tolerance traits such as described in D'Hafluin, cited supra., or An, cited supra. The plant regeneration protocol allows the development of somatic embryos and the subsequent growth of roots and shoots. To determine that the herbicide-tolerance trait is expressed in differentiated organs of the plant, and not solely in undifferentiated cell culture, regenerated plants are exposed to herbicide levels which will normally inhibit shoot and root formation and growth.

Mature maize plants are then obtained from maize cell lines that are known to express the trait. If possible, the regenerated plants are self-pollinated. Otherwise, pollen obtained from the regenerated plants is crossed to seed-grown plants of agronomically important inbred lines. Conversely, pollen from plants of these inbred lines is used to pollinate regenerated plants. The genetics of the trait are then characterized by evaluating the segregation of the trait in the first and later generation progeny. Stable inheritance of overexpression of a plant acetyl CoA carboxylase or a functional mutant of a plant acetyl CoA carboxylase conferring herbicide tolerance to the plant is achieved if the plants maintain herbicide tolerance for at least about three to six generations.

Seed from transformed monocot plants regenerated from transformed tissue cultures is grown in the field and self-pollinated to generate true breeding plants. Progenies from these plants become true breeding lines which are evaluated for herbicide tolerance in the field under a range of environmental conditions. Herbicide tolerance must be sufficient to protect the monocot plants at the maximum labeled delivery rate under field conditions which cause herbicides to be most active. Appropriate herbicide concentrations and methods of application are those which are known and have been developed for the cyclohexanedione and/or aryloxyphenoxypropanoic acid herbicides in question.

In a preferred version, an expression cassette comprised of a maize acetyl CoA carboxylase gene isolated from a maize cell line tolerant to sethoxydim and haloxyfop and linked to the 35S CaMV promoter is introduced into an herbicide sensitive monocot tissue using biolistic transformation. Transformed calli are selected and used to generate transgenic plants. Transformed calli and transgenic plants can be evaluated for tolerance to sethoxydim and haloxyfop and for stable inheritance of the tolerance trait.

D. Method for Altering the Oil Content in a Plant

The invention also provides a method of altering the oil content in a plant. The method include the steps of introducing an expression cassette comprising a gene coding for plant acetyl CoA carboxylase or functional mutant thereof operably linked to a promoter functional in a plant cell into the cells of plant tissue and expressing the gene in an amount effective to alter the oil content of the plant cell. An alteration in the oil content of a plant cell can include a change in the total oil content over that normally present in that type of plant cell, or a change in the type of oil from that normally present in the plant cell. Expression of the gene in an amount effective to alter the oil content of the gene depends on whether the gene codes for an unaltered acetyl CoA carboxylase or a mutant or altered form of the gene. Expression of an unaltered plant acetyl CoA carboxylase gene in an effective amount is that amount that may provide a change in the oil content of the cell from about 1.2- to 20-fold over that normally present in that plant cell, and preferably increases the amount of acetyl CoA carboxylase about 2- to 20-fold over that amount of the enzyme normally present in that plant cell. An altered form of the enzyme can be expressed at levels comparable to that of the native enzyme or less if the altered form of the enzyme has higher specific activity.

An alteration in oil content of the plant cells according to the method of the invention can be achieved in at least two ways including:

(1) an increase or decrease in expression of an unaltered plant acetyl CoA carboxylase gene; or (2) by introducing an altered or functional mutant plant acetyl CoA carboxylase gene coding for an enzyme that exhibits a change in specific activity.

The level of gene expression of an unaltered plant acetyl CoA carboxylase gene can be increased by either combining an unaltered plant acetyl CoA carboxylase gene with a promoter that provides for a high level of gene expression, such as the 35S cauliflower mosaic virus or by introducing the expression cassette and/or selecting for plant cells having multiple copies of a plant acetyl CoA carboxylase gene integrated into the genome. A decrease in expression of an unaltered acetyl CoA carboxylase can be achieved by transformation with an ACCase antisense gene containing an expression cassette. When an altered or functional mutant plant acetyl CoA carboxylase gene codes for an enzyme that has an increase in specific activity, it may lead to an increase in total oil content of a plant cell even if the level of gene expression is comparable to that of the native enzyme. When an altered or functional mutant acetyl CoA carboxylase gene codes for an enzyme having a decrease in specific activity, it may lead to a decrease in the total oil content of the plant cell compared to that normally present.

An expression cassette as described above can be introduced into either monocots or dicots. Preferably, the expression cassette is introduced into dicot plants such as soybean, canola, and sunflower. An expression cassette can be introduced by standard methods including protoplast transformation, Agrobacterium-mediated transformation, microprojectiles, electroporation, and the like. Transformed cells or tissues can be selected for the presence of a selectable marker gene.

Transient expression of a plant acetyl CoA carboxylase gene can be detected in transformed cells or tissues by immunoreactivity with antibodies specific for the cloned acetyl CoA carboxylase. Overexpression of a plant acetyl CoA carboxylase can be detected by quantitative Western blots. A change in specific activity of the enzyme can be detected by measuring enzyme activity in the transformed cells. A change in total oil content can also be examined by standard methods, as described in Clark & Snyder, *JACS*, 66:1316 (1989).

Transgenic plants and seeds can be generated from transformed cells and tissues showing a change in oil content or in the amount or specific activity of a plant acetyl CoA carboxylase using standard methods. It is especially preferred that the oil content of the leaves, seeds, or fruits is increased.

In a preferred version, a maize acetyl CoA carboxylase gene is combined with a 35S cauliflower mosaic virus promoter in a vector such as pBI121 or pBI221 and introduced into soybean cells using the microprojectile method. Transformed soybean cells showing an increase in expression of acetyl CoA carboxylase of at least about 2-fold or at least a 1.2-fold increase in oil content are selected. Transformed soybean cells exhibiting overexpression of acetyl CoA carboxylase or showing an increase in total oil content are used to generate transgenic plants and seeds.

E. Method of Producing Plant Acetyl CoA Carboxylase

The invention also provides a method of producing plant acetyl CoA carboxylase in a host cell. The method includes the steps of introducing an expression cassette comprised of a gene encoding a plant acetyl CoA carboxylase or functional mutant thereof into a host cell and expressing the gene in an amount sufficient to allow for crystallization of the plant acetyl CoA carboxylase. An amount sufficient to allow for crystallization of a plant acetyl CoA carboxylase is about 20- to 100-fold increase over the amount of plant acetyl CoA carboxylase that can normally be purified from plant cells, preferably about 2 to 10 mg protein. Crystallized plant acetyl CoA carboxylase can be used to identify other herbicides that can bind to and inhibit acetyl CoA carboxylase function. In addition, the availability of large amounts of purified enzyme provides for screening of the efficacy of such herbicides.

An expression cassette can include a promoter that is functional in either a eukaryotic or prokaryotic cell. The expression cassette can be introduced into a prokaryotic cell such as *E. coli*, or a eukaryotic cell such as a plant or yeast. The preferred cell is a prokaryotic cell used routinely in producing recombinant proteins such as *E. coli*. The expression cassette can be introduced and transformed cells selected by standard methods.

The plant acetyl CoA carboxylase gene can be expressed in an prokaryotic cell until sufficient amount of the enzyme is produced so that it can be crystallized. Plant acetyl CoA carboxylase can be isolated from bacterial cells using standard methods, including those described in Example V. The purified acetyl CoA carboxylase can then be crystallized and characterized by standard methods.

EXAMPLE I

Identification of Herbicide Mechanism and Site of Action

The objective of this Example was to identify the mechanism whereby sethoxydim and/or haloxyfop inhibit fatty acid synthesis in maize. The results, reported in J. D. Burton et al., *Biochem. Biophys. Res. Comm.*, 148, 1039 (Nov. 13, 1987), show that both sethoxydim and haloxyfop inhibit acetyl-coenzyme A carboxylase (ACCase) (EC 6.4.1.2) in maize chloroplasts.

A. Chemicals

Buffers and cofactors were purchased from Sigma Chemical Company (St. Louis, Mo.); $[2-^{14}C]$acetate was purchased from Research Products International; $12-^{14}C]$pyruvate and $[14CNaHCO_3$ were purchased from New England Nuclear; and $[2-^{14}C]$malonyl coenzyme A was purchased from Amersham. Sethoxydim was a gift from BASF (Parsippany, N.J.), and haloxyfop was provided by Dow Chemical USA (Midland, Mich.).

B. Plant Growth Conditions

Corn (*Z. mays L.*, 'B37xOh43') seeds were germinated in darkness for 96 hours in vermiculite in an incubation chamber maintained at 30° C., 80% RH. Seedlings were then transferred to a growth chamber with a 16 hour light (25° C.) and an 8 hour dark (20° C.) cycle, 90% relative humidity (RH). After greening 48 hours, seedlings were returned to the dark incubation chamber for 12 hours to deplete chloroplast starch reserves. Seedlings were harvested 6 days after planting. Pea (*P. sativum L.*, 'PI 9901-C') seedlings were grown in vermiculite in a growth chamber with a 16 hour light (21° C.) and 8 hour dark (16° C.) cycle, 80% RH. Peas were harvested 10 to 13 days after planting. Black Mexican Sweet (BMS) corn suspension cultures were maintained in a supplemented Murashige-Skoog (MS) medium (C. E. Green, *Hort. Sci.*, 12, 7–10 (1977)), and subcultured weekly by 20-fold dilution of the suspension culture into fresh medium.

C. Chloroplast Isolation

Chloroplasts from corn and pea seedlings were isolated at 4° C. (K. Cline et al., *J. Biol. Chem.*, 260, 3691–3696 (1985)). Seedlings (50 g of shoots) were homogenized in 200 ml buffer A (50 mM HEPES-NaOH pH 7.5, 330 mM sorbitol, 0.1% w/v BSA, 1 mM $MgCl_2$, 1 mM $MnCl_2$, 2 mM EDTA, 5 mM isoascorbate, 1.3 mM glutathione) in an omnimixer (five, 3-second bursts at full speed). The homogenate was filtered through six layers of cheesecloth and two layers of miracloth, and then centrifuged at 3000 g for 3 minutes with hand-braking. The pellet was gently resuspended in buffer A and layered onto a preformed linear Percoll gradient (50 mM HEPES-NaOH pH 7.5, 330 mM sorbitol, 1.9 mM isoascorbate, 1.08 mM glutathione, 0.1% w/v BSA, 50% Percoll) which was centrifuged at 3000 g for 20 minutes in a Sorvall HB-4 rotor. The lower band in the gradient, containing intact chloroplasts, was washed twice by gently resuspending it in 20 ml of buffer B (50 mM HEPES-NaOH, pH 7.5, and 330 mM sorbitol) followed by repelleting (3000 g, 5 minutes). The final pellet, consisting of intact chloroplasts, was resuspended in 2 to 3 ml of buffer B and stored on ice in the dark until use.

D. Fatty Acid Synthesis

[$^{14}$C]acetate and [$^{14}$C]pyruvate were used as precursors to measure fatty acid biosynthesis in isolated chloroplasts (B. Liedvogel et a]., *Planta*, 169, 481–489 (1986)). [$^{14}$C]acetate incorporation was assayed in a 0.5 ml-volume containing: 50 mM HEPES-NaOH (pH 7.5), 330 mM sorbitol, 5 mM $KH_2PO_4$, 10 mM $NaHCO_3$, 1 mM $MgCl_2$, 1 mM ATP, 0.1 mM CoA, 0.15 mM [$^{14}$C]acetate (3.33 mCi/mmol), and chloroplasts (20 to 50 μg chlorophyll). [$^{14}$C]pyruvate incorporation into fatty acids was assayed in the same medium except that it included 2 mM TPP, 1 mM $NAD^+$, 0.15 mM [$^{14}$C]-pyruvate (1.33 mCi/mmol), but no acetate. Assay suspensions were illuminated with 1400 μE/m$^2$·second PAR at 25° C. Assays were initiated by the addition of the labelled substrate and stopped by the addition of 0.5 ml of 40% KOH. To determine the incorporation of radiolabel into a non-polar (fatty acid) fraction, each treatment was saponified at 90° C. for 30 minutes in capped vials (P. B. Hoj et al., *Carlsberg Res. Commun.*, 47, 119–141 (1982)). The vials were acidified with 0.5 ml 40% 112$SO_4$, and carrier fatty acids (20 μg each of C 14:0, C 16:0, and C 18:0) were added. The assay mixture was extracted twice with 4 ml hexane. The extracts were combined, dried under $N_2$, and redissolved in 0.3 ml hexane. Aliquots (50 μl) were counted for radioactivity by liquid scintillation spectrometry.

Incorporation of [$^{14}$C]malonyl-Coenzyme A into fatty acids (P. B. Hoj et al., supra; and J. B. Ohlrogge et al., *Proc. Natl. Acad. Sci. USA*, 76, 1194–1198 (1979)) was assayed using cell-free preparations from BMS tissue culture. Cells harvested during logarithmic growth phase were frozen in liquid nitrogen, ground with a mortar and pestle, and thawed in a medium containing: 0.1 M HEPES-KOH, pH 7.5; 0.3 M glycerol, and 5 mM DTT (buffer:tissue, 2:1, v/w). The homogenate was centrifuged at 12,000 g for 20 minutes. The supernatant was filtered through miracloth and centrifuged (125,000 g) for 60 minutes and then filtered through miracloth and assayed. Assays were conducted at 25° C. in a 0.4 ml volume containing: 1.0 mM ATP, 0.32 mM NADPH, 0.38 mM NADH, 25 μM CoA, 10 μM acetyl-CoA, 25 μg acyl-carrier protein, and 12 μM malonyl-CoA (11.54 μCi/mol). Reactions were initiated by addition of [$^{14}$C]malonyl CoA and stopped by addition of 0.4 ml 40% KOH. Label incorporation into fatty acids was determined as above. Chlorophyll (D. I. Arnon, *Plant Physiol.*, 24, 1–15 (1949)) and protein (P. K. Smith et al., *Anal. Biochem.*, 150, 76–85 (1985)) were determined as described therein.

E. Acetyl-Coenzyme A Carboxylase (ACCase) Activity

Maize chloroplasts, isolated as described above, were suspended in buffer C (0.1 M Tricine-KOH, pH 8.0; 0.3 M glycerol, and 1 mM DTT) and homogenized in a glass tissue homogenizer. The disrupted chloroplast fraction was centrifuged at 16,000 g for 15 minutes. The supernatant was desalted on a Sephadex G-25 column (1.5×5 cm equilibrated with 0.1 M Tricine-KOH, pH 8.0; and 0.3 M glycerol) and assayed directly. ACCase activity (B. J. Nikolau et al., *Arch. Biochem. Biophys.*, 211, 605–612 (1981)) was assayed at 30° C. in a 0.2 ml volume which contained 1 mM ATP, 3 mM acetyl coenzyme A, 2.5 mM $MgCl_2$, 50 mM KCl, 0.5 mM DTT, and 15 mM [$^{14}$C]$NaHCO_3$ (0.17 mCi/mmol). Reactions were initiated by addition of acetyl coenzyme A and stopped by addition of 25 μl of 12 N HCl. Product formation was determined by the radioactivity found in an acid stable fraction by liquid scintillation spectrometry. Enzyme activity was linear for 15 minutes.

F. Results

To probe for the site of herbicidal activity of sethoxydim and haloxyfop, labelled acetate, pyruvate, and malonyl-CoA were used individually as precursors for fatty acid synthesis.

Isolated chloroplasts from corn seedlings incorporated [$^{14}$C] acetate and [$^{14}$C]pyruvate into a non-polar fraction (fatty acids). Acetate incorporation was linear for 30 min after a 5 min lag period, and dependent upon the addition of free acetyl coenzyme A. Addition of either 10 μM sethoxydim or 1 μM haloxyfop inhibited [$^{14}$C]acetate incorporation into fatty acids by 90% and 89%, respectively, as shown in Table I, below. Sethoxydim (10 μM) and haloxyfop (1 μM) also inhibited the incorporation of [$^{14}$C]pyruvate into fatty acids by 98% and 99%, respectively.

TABLE I

Inhibition of [$^{14}$C]acetate and [$^{14}$C]pyruvate Incorporation into Fatty Acids in Corn Seedling Chloroplasts by Sethoxydim (10 μM) and Haloxyfop (1 μM), 10 minute assay time

|  | Acetate | Pyruvate |
| --- | --- | --- |
|  | Activity (nmol/mg chl · min) | |
| Control | 4.4 ± 0.4[1] | 10.8 ± 2.3 |
|  | % Inhibition | |
| Sethoxydim | 90 ± 2.5 | 98 ± 1.1 |
| Haloxyfop | 89 ± 3.1 | 99 ± 0.3 |

[1]Results are expressed as mean of two experiments ± standard error.

The effect of 10 μM sethoxydim and 1 μM haloxyfop on [$^{14}$C]malonyl-CoA incorporation into fatty acids was determined using cell-free extracts from corn suspension cultures. Neither sethoxydim (10 μM) nor haloxyfop (1 μM) inhibited fatty acid synthetase activity. Thus, both herbicides inhibited fatty acid synthesis in intact chloroplasts from corn seedlings with either acetate or pyruvate as a precursor, but did not inhibit incorporation of malonyl-CoA into fatty acids. This suggests that ACCase which catalyzes the formation of malonyl-CoA is the site of action of these herbicides.

EXAMPLE II

Selection and Characterization of Herbicide-tolerant Cell Lines

A selection protocol to identify and isolate herbicide-tolerant maize cells was developed to minimize the adverse effects of high herbicide concentrations on somatic embryo development and plant regeneration capacity. The procedure involved exposing tissue to gradually increasing concentrations of herbicide beginning with a sethoxydim concentration representing ¹⁄₂₀th of lethal dose and doubling the herbicide concentration at approximately two-week intervals until the lethal dose (10 μM sethoxydim) was reached. In this way, the herbicide was allowed to take effect slowly with continuous selection pressure, thus permitting herbicide-tolerant cells to accumulate over time while not affecting the potential for plant regeneration.

A. Selection of a Sethoxydim-Tolerant Cell Line

Many selections were carried out utilizing the selection protocol described in the preceding paragraph. The selection of one such sethoxydim-tolerant cell line that was identified and characterized is described below in detail.

Approximately 100 grams of vigorously growing, regenerable, friable, embryogenic maize callus tissue established from an $F_1$ immature embryo resulting from the cross A188×B73 were transferred to agar-solidified maintenance medium (Armstrong and Green, Planta, 164, 207 (1985)) in petri plates containing 0.5 μM sethoxydim (BASF)

(Parsippany, N.J.). This callus line was designated 2167-9/2160-154. Forty plates were prepared and five clumps of callus tissue weighing about 0.5 grams each were placed on each plate. The 0.5 $\mu$M sethoxydim concentration was chosen from growth inhibition studies to provide less than 10–20% growth inhibition during the first two weeks of herbicide exposure. After 14 days, 0.25–0.5 gram pieces of tissue showing vigorous growth rate and retention of embryogenic morphology (i.e., presence of somatic embryos) were subcultured on fresh medium containing 1.0 $\mu$M sethoxydim. Eighty plates containing five pieces of tissue per plate were prepared. For each subsequent transfer, all callus tissue showing growth and somatic embryo forming ability was placed on fresh media containing a two-fold increased sethoxydim concentration. Therefore, callus was transferred at two-week intervals to petri plates containing 0.5, 1.0, 2.0, 5.0 and 10.0 $\mu$M sethoxydim. During the course of the selection process, the total number of lines decreased as the herbicide-mediated growth inhibition became more intense. Cell lines exhibiting growth on 10 $\mu$M sethoxydim were designated as herbicide-tolerant and given an identification number. Two sethoxydim-tolerant lines were recovered that exhibited uninhibited growth at 10 $\mu$M sethoxydim. These lines were designated 2167-9/2160-154 S-1 and 2167-9/2160-154 S-2.

B. Characterization of Herbicide-Tolerant Maize Cell Line 2167-9/2160-154 S-2

Tolerant cell line 2167-9/2160-154 S-2 ("S-2") was characterized to evaluate: (1) the magnitude of sethoxydim tolerance; (2) cross-tolerance of haloxyfop; and (3) the biochemical basis for the tolerance. Callus tissue from S-2 that had been maintained on 10 $\mu$M sethoxydim was transferred to media containing up to 100 $\mu$M sethoxydim. One-half gram of S-2 tissue was plated on a 7 cm filter paper as a lawn overlaying 50 ml agar-solidified culture medium containing 0, 0.5, 1.0, 2.0, 5.0, 10.0, 50.0 and 100 $\mu$M sethoxydim, and cultured for two weeks. Control cell line 2167-9/2160-154 was plated similarly on medium containing the same levels of sethoxydim. The results of this study are summarized in FIG. 2. The control cell line growth after two weeks was inhibited 50% at 1 $\mu$M sethoxydim. Growth of S-2 was not inhibited at 100 $\mu$M sethoxydim, indicating that S-2 was at least 100-fold more tolerant than the control callus line.

Growth of S-2 was inhibited with 0.65 KM haloxyfop, whereas the control cell line was inhibited 50% with 0.02 $\mu$M, indicating approximately a 30-fold increase in tolerance.

C. Acetyl-Coenzyme A Carboxylase (ACCase) Activity of Maize Cell Line S-2

Assays were conducted to determine if ACCase extracted from cell line S-2 was altered with respect to herbicide activity. ACCase activity of control tissue was 50% inhibited either by 1.5 $\mu$M sethoxydim, or by 0.25 $\mu$M haloxyfop. ACCase activity of S-2 tissue was inhibited 50% either by 70 $\mu$M sethoxydim, or by 1.8 $\mu$M haloxyfop, indicating at least 40-fold and 7-fold decreases in herbicide sensitivity on concentration basis, respectively.

EXAMPLE III

Plant Regeneration and Production of Herbicide-Tolerant Seed

A. Plant Regeneration Protocol

Sixteen ca. 150 mg clumps of S-2 callus were transferred per 25×100 mm petri plate containing agar-solidified N6 basal salts and 6% sucrose and incubated 7–14 days in low light (20 $\mu$E m$^{-2}$ s$^{-1}$). Several plates containing callus on plant regeneration medium were prepared. Callus was transferred to agar-solidified Murashige-Skoog (MS) medium without hormones and incubated in high intensity light (200 $\mu$E m-2 s$^{-1}$) for shoot elongation. Developing plants (1–3 cm long) were isolated from the callus surface and transferred to magenta boxes containing agar-solidified MS salts, 2% sucrose with no hormones for two weeks of further growth. When plants reached the 2–3 leaf stage, they were transplanted to peat pots containing potting soil, and were incubated in the growth room until growing stably. Surviving plants were transferred to soil in 4" diameter plastic pots and grown in the greenhouse.

B. Expression of Herbicide Tolerance in Plants Regenerated from S-2 Callus Tissue Groups of eight control (2167-9/2160-154 unselected) and eight S-2 plants were sprayed with either 0.0, 0.01, 0.05, 0.11, 0.22 or 0.44 kg/ha sethoxydim to determine whole plant sethoxydim-tolerance of greenhouse-grown plants. Control plants were killed by 0.05 kg/ha or more sethoxydim. Plants regenerated from the S-2 cell line survived the 0.44 kg/ha sethoxydim treatment, indicating that S-2 plants exhibit at least 20-fold more tolerance of sethoxydim than control. FIG. 3 shows the growth response of the regenerated plants seven days after treatment with 0.44 kg/ha sethoxydim. As shown in FIG. 4, shoot height of regenerated S-2 plants was only slightly reduced 14 days after treatment with 0.44 kg/ha sethoxydim.

C. Seed Production from S-2 Plants

Plants surviving sethoxydim treatments of up to 0.44 kg/ha were transplanted to the genetics plot on the University of Minnesota campus, St. Paul, Minn. Additional S-2 plants were transplanted to the field that had not been sprayed. Sixty-five 2167-9/2160-154 control plants and ninety-five S-2 plants were grown to maturity in the field. Plants were either self-pollinated or cross-pollinated to inbred maize lines A188, A619, A641, A661, A665, B37, B73, R806, and W153R. Control seed were produced by selfing 2167-9/2160-154 regenerated plants, or by crossing them with the inbreds listed above.

D. Expression of Herbicide Tolerance in Progeny of Regenerated Plants

Seeds obtained by the crossing procedure described above were viable and germinated normally. Seeds from thirty S-2 selfed plants and fifteen 2167-9/2160-154 control plants were planted in 25×50 cm trays of soil (28 seeds from each plant in one tray) and grown in the greenhouse. Seedlings at the 3–4 leaf stage were treated with 0.1, 0.44, and 1.1 kg/ha sethoxydim and evaluated for visual herbicide damage and shoot height. Based on visual rating of herbicide damage two weeks after treatment, selfed progeny of S-2 plants segregated approximately 1:2:1 for healthy, uninjured plants: to plants showing partial injury: to dead plants, respectively, at 0.44 and 1.1 kg/ha sethoxydim treatments. All control progeny of 2167-9/2160-154 control plants were killed by 0.1 kg/ha and greater levels of sethoxydim. These results demonstrate dominant expression of sethoxydim tolerance indicating that sethoxydim tolerance in S-2 plants is a heritable trait. Similar tests were conducted on progeny of S-2 plants crossed to the other inbreds. In all cases, these test cross progeny treated with 0.44 kg/ha sethoxydim segregated 1:1 for growing shoots versus dead shoots whether S-2 plants were used as male or female parents. These results confirm that sethoxydim tolerance is controlled by a single dominant nuclear gene. In all cases, control plants crossed to the other inbreds were killed and therefore sethoxydim-sensitive.

E. Method for Obtaining Uniform Herbicide-Tolerant Seed

Progeny of S-2 plants surviving sethoxydim treatments of 0.44 and 1.1 kg/ha and showing no herbicide injury were transferred to the greenhouse and grown to maturity. These plants may be selfed and their progeny evaluated for sethoxydim and haloxyfop tolerance to identify pure breeding herbicide-tolerant maize lines.

Progeny of S-2 plants crossed to inbred lines and exhibiting sethoxydim tolerance may be recurrently backcrossed to the same inbreds. Progeny of each cross may be screened for sethoxydim-tolerance, and tolerant plants grown to maturity and again crossed to the recurrent parent. After six or seven cycles of backcrossing, sethoxydim-tolerant plants may be selfed and progeny screened for tolerance to produce homozygous sethoxydim tolerant maize inbreds.

EXAMPLE IV

Selection of Additional Herbicide-Tolerant Maize Cell Lines

One primarily sethoxydim-tolerant maize cell line, 2167-9/2160-154 S-1, and two haloxyfop-tolerant maize cell lines, 2167-9/2160-154 H-1 and 2167-9/2160-154 H-2, were selected and characterized as follows:

A. Selection of Maize Cell Line 2167-9/2160-154 S-1

Maize cell line 2167-9/2160-154 S-1 was selected from maize cell culture using the protocol described in detail above for the selection of Line 2167-9/2160-154 S-2. Approximately 70 plants were regenerated from Line 2167-9/2160-154 S-1, and either self-pollinated or cross-pollinated to the inbred maize lines A188, A619, A641, A661, A665, B37, B73, R806, and W153R.

B. Selection of Maize Cell Line 2167-9/2160-154 H-1

Line 2167-9/2160-154 H-1 was selected from maize cell culture using a similar protocol described in detail above except maize callus tissue was selected using the herbicide haloxyfop. Maize callus tissue was initially plated on 0.01 $\mu$M haloxyfop. At two-week intervals, surviving tissue was sub-cultured onto 0.05, 0.10 and 0.20 $\mu$M haloxyfop. Approximately 50 plants were regenerated from Line 2167-9/2160-154 11-1, and were self-pollinated.

C. Selection of Maize Cell Line 2167-9/2160-154 H-2

Line 2167-9/2160-154 H-2 was selected from maize cell culture using a similar protocol described in detail for line 2167-9/2160-154 H-1. No plants have been successfully regenerated from this line.

D. Characterization of Lines 2167-9/2160-154 S-1. H-1 and H-2

The tolerant callus cultures were characterized to determine the magnitude of sethoxydim and haloxyfop tolerance. Callus tissue from these lines was evaluated in experiments as described above in the characterization of line 2167-9/2160-154 S-2. Table II summarizes the results of these studies. Line 2167-9/2160-154 S-1 and Line 2167-9/2160-154 H-2 showed a four-fold increase in haloxyfop tolerance, while Line 2167-9/2160-154 H-1 exhibited approximately a 60-fold increase in haloxyfop tolerance. Neither haloxyfop selected line showed a significant degree of sethoxydim tolerance, while the sethoxydim selected line S-1 exhibited approximately a 100-fold increase in sethoxydim tolerance.

TABLE II

Herbicide Tolerance of Cell Lines S-1, H-1 and H-2

| Cell Line | Herbicide | |
|---|---|---|
| | Haloxyfop | Sethoxydim |
| 2167-9/2160-154 S-1 | 4[1] | 100 |
| 2167-9/2160-154 H-1 | 61 | 0 |
| 2167-9/2160-154 H-2 | 4 | 0 |

[1]The numbers represent the fold increase in herbicide concentration that results in a 50% reduction in growth of the selected cell lines compared to the unselected control cell line 2167-9/2160-154.

E. Herbicide Inhibition of Acetyl Coenzyme A Carboxylase of Maize Cell Lines S-1. H-1 and H-2

Acetyl Coenzyme A Carboxylase (ACCase) was extracted from cell lines S-1, H-1 and H-2 and assayed as described in detail for maize cell line S-2, above. Table III below summarizes the results of these studies. The ACCase from line S-1 was more tolerant of both sethoxydim and haloxyfop, while the ACCase from line H-1 was more tolerant of haloxyfop, but not of sethoxydim. The ACCase from line H-2 showed no difference from the unselected parent line 2167-9/2160-154 in sensitivity to either herbicide.

However, cell line H-2 exhibited approximately a five-fold higher level of ACCase activity as compared to the unselected parent line 2167-9/2160-154. Thus, selection for sethoxydim or haloxyfop tolerance resulted in a less sensitive ACCase in cell line S-1 and H-1, as well as a higher level of ACCase activity in cell line H-2.

TABLE III

Herbicide Inhibition of ACCase of Maize Cell Lines S-1, H-1 and H-2

| Cell Line | Herbicide | |
|---|---|---|
| | Haloxyfop | Sethoxydim |
| 2167-9/2160-154 S-1 | 3 | 4 |
| 2167-9/2160-154 H-1 | 7 | 0 |
| 2167-9/2160-154 H-2 | 0 | 0 |

[1]The numbers represent the fold increase in herbicide concentration that inhibits ACCase activity of the selected cell lines by 50% compared to the unselected parent cell line 2167-9/2160-154.

Deposit of Seeds

Seeds from representative S-2 plants (Ex. III (B)) and 11-1 plants (Ex. IV(B)) have been deposited with the American Type Culture Collection, 12301 Parklawn Drive, Rockville, Md. 20852 USA on Oct. 25, 1988 and assigned accession numbers ATCC 40507, and ATCC 40508, respectively.

EXAMPLE V

Formation of cDNA Clones Encoding ACCase

A. ACCase Purification

The acetyl CoA carboxylase enzyme was isolated and purified from plant tissues and characterized. The purified enzyme was used to generate antibody reagents useful in identifying cDNA clones encoding the gene or portions of the gene for ACCase.

ACCase was extracted from frozen shoots of 7-d-old maize (*Zea Mays L.* inbred A619 or B73) seedlings grown in a growth chamber (24° C., 90% RH, 16-h daylength at 210 $\mu$E m$^{-2}$ s$^{-1}$). The outermost leaf and blade were removed and the remainder of the shoot was frozen in liquid $N_2$. Embryos and endosperm tissue from developing kernels were harvested from field-grown ears at 36 to 40 days after pollination (DAP). Black Mexican Sweet corn (BMS) maize suspension cells were obtained from cultures as previously described (W. B. Parker et al., *Plant Physiol.*, 92, 1220–1225 (1990)). Tissues were stored in liquid $N_2$ until used.

Extraction and purification steps were performed at 0 to 4° C. Crude extracts of leaf, bundle sheath strands, embryo, endosperm, and BMS cells were prepared from frozen tissue as described by W. B. Parker et al., *Proc. Nat–l Acad. Sci. USA*, 87, 7175–7179 (1990), except that extraction buffer contained 0.1 M Tricine-KOH, pH 8.3, 0.3 M glycerol, 5 mM DTT, 2 mM $Na_2EDTA$, and 0.5 mM phenyl methonyl sulfonyl fluoride (PMSF). Triton X-100 (0.01% v/v) was added to bundle sheath strand extracts and to some whole leaf extracts. For some experiments, additional protease inhibitors (leupeptin, 2 µg ml; pepstatin A, 100 µg mL⁻; benzamidine, 1 mM; $\epsilon$-amino-n-caproic acid, 5 mM; and soybean trypsin inhibitor, 10 µg $mL^{-1}$) were included. Filtered homogenates were centrifuged 20 minutes at 30,000 g. A portion of the crude supernatant fraction was immediately boiled 5 minutes in 1 volume of SDS sample buffer (W. B. Parker et al., *Plant Physiol.*, 92, 1220–1225 (1990)) for SDS-PAGE analysis; the remainder was desalted on a 10-mL Sephadex G-25 column into extraction buffer minus PMSF.

ACCase was purified from the crude extract supernatant in four steps. This fraction was brought to 30% saturation with solid $(NH_4)_2SO_4$, stirred 15 minutes, and centrifuged 20 minute at 20,000 g. The supernatant was then brought to 40% saturation with $(NH_4)_2SO_4$ solution, stirred 30 minutes, and centrifuged. The pellet was dissolved in 5 mL extraction buffer, microfuged 5 minutes, and the resulting supernatant was applied to a Sephacryl S-300 gel filtration column (Pharmacia; 2.5×46 cm) equilibrated with S-300 buffer (0.1 M Tricine-KOH, pH 8.3, 0.5 M glycerol, 0.5 mM DTT, 2 mM Na50 mM KCl). In later experiments a Sephacryl S-400 column was used. Fractions (2.5 mL) were eluted at 0.75 mL $min^{-1}$. ACCase activity eluted shortly after the void $A_{280}$ peak ($V_0$=75 mL). Active fractions were pooled, brought to 4.25 mM $MgCl_2$ (from a 0.5 M solution), and applied at 0.2 mL $min^{-1}$ to a Blue Sepharose CL-6B (Pharmacia; 1.5×15 cm) equilibrated with Blue sepharose buffer (S-300 buffer containing 4.25 mM $MgCl_2$ and 10 mM $NaHCO_3$). The column was washed overnight with 150 ml buffer (0.45 mL min⁻). ACCase activity was then eluted with 50 mL buffer plus 10 mM ATP (0.45 mL $min^{-1}$). Active fractions were pooled and applied to an FPLC Mono-Q HR 5/5 anion-exchange column (Pharmacia) equilibrated with S-300 buffer minus KCl. The column was washed with 30 mL S-300 buffer minus KCl and then with a 48-mL, 0 to 500 mM KCl gradient in S-300 buffer (0.25 mL $min^{-1}$). Fractions (1 mL) from the two peaks of ACCase activity were pooled separately. All purification fractions were desalted into S-300 buffer and assayed for ACCase activity and protein.

ACCase was also analyzed from mesophyll chloroplasts and bundle sheath strands. Mesophyll chloroplasts from homogenates of 7- to 8-day-old seedlings that were kept in the dark 24 hours prior to harvesting were isolated on a linear Percoll gradient according to J. D. Burton et al., *Pesticide Biochemistry and Physiology*, 34, 76–85 (1989), except that buffers contained 0.6 M sorbitol and centrifugation g-forces were reduced by 25%. Intact chloroplasts were taken from the discrete lower green band present after Percoll gradient centrifugation (G. Morioux et al., *Plant Physiol.*, 67, 470–473 (1981)). Pelleted chloroplasts were lysed by resuspending them in ACCase extraction buffer plus PMSF and 0.01% (v/v) Triton X-100. Bundle sheath strands were obtained from the original leaf homogenate material retained on a 70-µm filter after re-homogenizing the retentate five times in a total of 2 L buffer. Triton X-treated, desalted leaf, mesophyll chloroplast, and bundle sheath strand extracts were assayed for activities of Rubisco (G. Zhu et al., *Plant Physiol.*, 97, 1348–1353 (1991)), NADP-dependent malate dehydrogenase (M. D. Hatch et al., *Biochem. Biophys. Res. Commun.*, 34, 589–593 (1969)), phosphoenolpyruvate carboxylase (R. C. Leegood et al., "Isolation of Membranes and Organelles from Plant Cells," Academic Press, New York, 185–210( 1983)), catalase (Worthington Biochemicals, 1972), and fumarase (R. L. Hill et al., *Methods Enzymol.*, 13, 91–99 (1969)), and for total chlorophyll (D. E. Arnon, *Plant Physiol.*, 24, 1–5 (1949)). Mesophyll chloroplast preparations were judged to be relatively free of contamination by bundle sheath chloroplasts because they contained 3-fold greater NADP-dependent malate dehydrogenase and one-tenth as much Rubisco activity ($mg^{-1}$ chlorophyll) than bundle sheath strand extracts. Mesophyll chloroplast preparations also contained $\leq 2.6\%$ as much catalase, fumarase, and phosphoenolpyruvate carboxylase activities ($mg^{-1}$ chlorophyll) as did whole-leaf extracts, indicating they were relatively free of peroxisomal, mitochondrial, or cytoplasmic components.

ACCase activity as measured by acetyl-CoA-dependent $H^{14}CO_3$-(ICN, 2.07 GBq $mmol^{-1}$) incorporation into acid-stable product previously shown to be malonyl-CoA (J. D. Burton et al., *Pesticide Biochemistry and Physiology*, 34, 76–85 (1989)). Assays of desalted purification fractions or crude, desalted tissue extracts contained up to 50 and 25% (v/v) enzyme, respectively. In some experiments methylcrotonyl-CoA or propionyl-CoA were substituted for acetyl-CoA (E. S. Wurtele et al., *Archives of Biochemistry and Biophysics*, 278, 179–186 (1990)). Avidin (10 U $mL^{-1}$) was included in some assays. Herbicide inhibition assays contained 1% (v/v) ethanol plus or minus 1 µM haloxyfop (2-[4-[[3-chloro-5-(trifluoromethyl)-2-pyridinyl]oxy] phenoxy]propanoic acid, Dow Chemical Co. analytical grade racemic mixture) or 10 µM sethoxydim (2-[1 [(ethoxylmino)butyl]-5-[2-(ethylthio)-propyl]-3-hydroxy-2-cyclohexene-1-one, Li salt, BASF Corp. technical grade). Data are means plus standard error of three assays.

Protein concentrations were determined in duplicate with the Bio-Rad Coomassie blue dye-binding assay as described by the manufacturer, using BSA as the standard.

Centrifuged crude extracts and proteins in purification fractions and immunoprecipitation supernatants were separated by SDS-PAGE in 6 or 7.5% gels as previously described (W. B. Parker et al., *Plant Physiol.*, 92, 1220–1225 (1990)). Purification fractions were precipitated in 10% (v/v) TCA, washed with 80% (v/v) acetone, and air-dried 10 minutes prior to electrophoresis. Proteins in gels were stained with silver (J. Heukeshoven et al., *Electrophoresis*, 6, 103–112 (1985)). High molecular weight protein standards for SDS-PAGE (Pharmacia) were used to estimate polypeptide masses.

The four-step purification procedure shown in Table IV typically yielded 30 to 190 µg of highly purified ACCase from 50 grams (fresh weight) of maize inbred A619 or B73 seedling leaves. ACCase activity in the crude supernatant fraction precipitated between 30 and 40% saturation with $(NH_4)_2SO_4$, which appeared to increase total ACCase activity approximately 38%. Crude extract components might have depressed the reaction rate shown in Table IV because the assay mixture contained 50% enzyme (v/v). In tests of fractions from another purification, enzyme velocity was proportional to enzyme concentration in assay mixtures containing up to 25% (v/v) crude extract, but 50% (v/v) mixtures were not tested. ACCase activity eluted from the Sephacryl S-300 gel filtration column slightly after the green void peak. Approximately 56% of the S-300 fraction ACCase activity was recovered from the Blue Sepharose column, primarily in the initial ATP-containing fractions (12.5 mL). Both 10 mM NaHCO$_3$ and 4.25 mM MgCl$_2$ (1- and 0.85-fold standard assay concentrations, respectively) were included in the Blue Sepharose buffer because they improved the total and specific ACCase activity remaining after batch absorption to Blue Sepharose beads, elution with ATP, and desalting into extraction buffer minus PMSF. Neither NaHCO$_3$ nor MgCl$_2$ improved enzyme stability of crude extracts. Mono-Q anion-exchange chromatography resulted in separation of two ACCase activity peaks which eluted at approximately 210 mM (designated ACCase II) and 250 mM KCl (designated ACCase I), as previously observed for a hybrid maize variety (J. L. Howard et al., *FEBS Lett.*, 261, 261–264 (1990)). ACCase I comprised about 85% of the total activity recovered from the column (29% of the original crude extract activity) and had high specific activity (Table IV). The specific activity of ACCase II was less than 30% that of ACCase I. Both activities were inhibited >90% by avidin, as previously reported (J. L. Howard et al., *FEBS Lett.*, 261, 261–264 (1990)). The mass of native ACCase I was estimated to be approximately 490 kD by gel filtration on Superose 6.

TABLE IV

Purification of ACCase I From
Maize Inbred A619 Seedling Leaves[a]
All fractions were desalted into S-300 buffer and
assayed for protein and acetyl CoA dependent incorporation of
[$^{14}$C]HCO$_3^-$ into acid-stable products.

| Step | Protein mg | Activity units[b] | Specific Activity units/mg | Fold Purification | Activity Yield % |
|---|---|---|---|---|---|
| Crude extract | 215 | 2.45 | 0.0114 | 1 | 100 |
| 30–40% (NH$_4$)$_2$SO$_4$ | 45.1 | 3.37 | 0.0748 | 6.56 | 138 |
| S-300 | 10.7 | 3.35 | 0.313 | 27.5 | 137 |
| Blue Sepharose | 1.50 | 1.86 | 1.24 | 109 | 76 |
| Mono-Q (ACCase I) | 0.130 | 0.720 | 5.54 | 486 | 29 |

[a]Data are from one purification experiment starting with 50 g fresh weight of tissue and are representative of data obtained for eight purifications.
[b]Unit = 1 μmol acid-stable product min$^{-1}$.

B. Formation and Specificity of Antibodies to ACCase

Antibodies are sensitive reagents that allow for the identification of gene products from cDNA and other cloned genes. Antibodies to purified ACCase were prepared and used to screen for cDNA clones encoding all or a portion of a gene for ACCase.

Antiserum to maize ACCase was obtained by immunizing a female New Zealand White rabbit (Egli et al., *Plant Physiol.*, 101, 499 (1993)). An intramuscular injection of 100 μg of Mono-Q-purified, SDS-denatured ACCase I in Freund's complete adjuvant was followed by subcutaneous injections of 20 to 100 μg of gel-purified ACCase I polypeptide in acrylamide plus incomplete adjuvant every 4 to 6 weeks, for a total of six injections. Serum was stored at −20° C. in 0.02% (w/v) NaN$_3$.

For Western blots, proteins in SDS gels were electrophoretically transferred to Immobilon (W. B. Parker et al., *Plant Physiol.*, 92, 1220–1225 (1990)) for 1 hour at 20 V in a Bio-Rad Transphor semi-dry blotter and then stained with Ponceau S (E. Harlow et al., "Antibodies—A Laboratory Manual, Cold Spring Harbor Laboratory, Cold Spring Harbor, N.Y. (1988)). Destained blots were blocked with Tris-buffered saline plus 0.5% (v/v) Tween-20 (Bio-Rad), and 10% (w/v) bovine serum (for antiserum blots only). ACCase and biotinylated proteins were detected with immune serum (1/10,000) plus goat anti-rabbi IgG-alkaline phosphatase conjugate or with avidin-alkaline phosphatase (W. B. Parker et al., *Plant Physiol.*, 92, 1220–1225 (1990)). Blots were repeated at least three times.

For immunoprecipitations, equal ACCase activities (0.58 nmol min$^{-1}$) in crude extracts were desalted into S-300 buffer containing 0.1 M KCl and incubated 1 hour at 25° C. with 16 μL buffer or with 16 μL serum consisting of 0 to 100% ACCase antiserum in preimmune serum. Immune complexes were incubated 1 hour at 25° C. with a 2-fold (IgG binding) excess of Protein A-agarose and then microfuged 5 minutes to obtain immunoprecipitation supernatant fractions. ACCase activity of supernatants was expressed as a percent of the 100% preimmune serum control. Data are means plus SE of three replicate assays for each of two sets of extracts.

Figure 5:
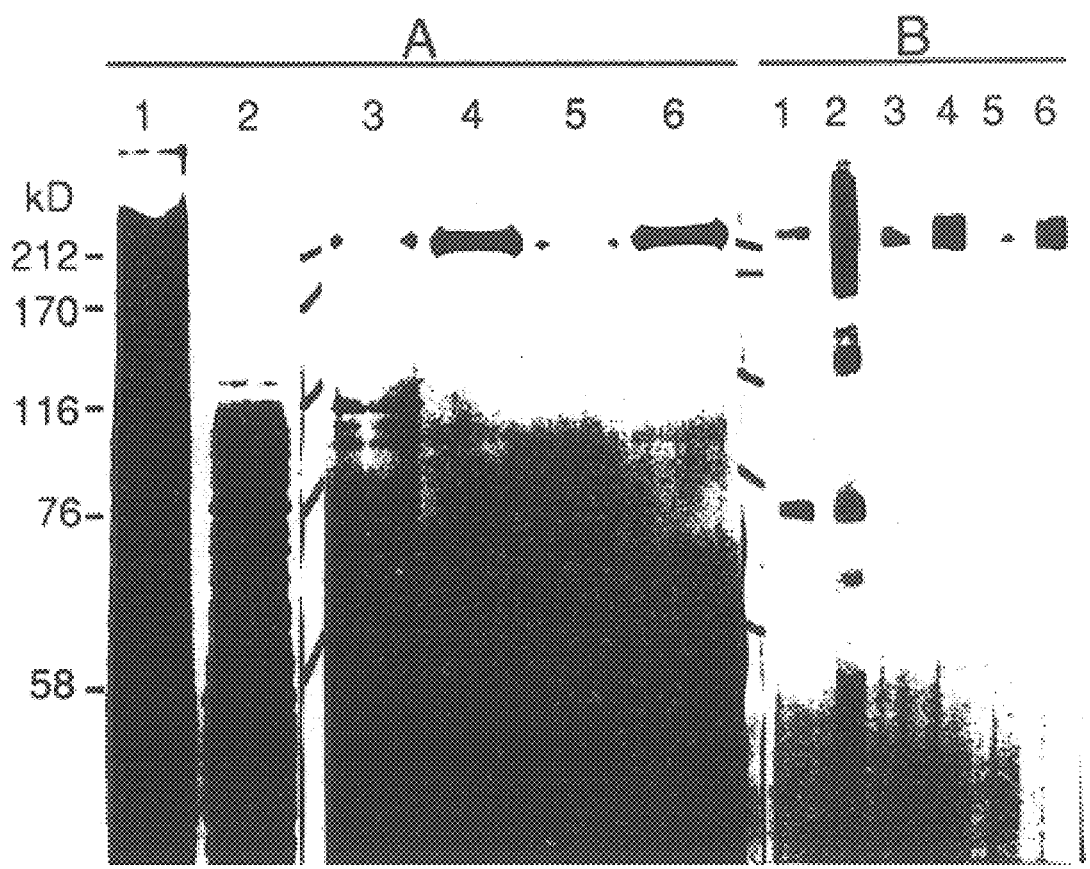
FIGS. 5A–5B: Total soluble and biotinylated polypeptides in ACCase purification fractions from seedling leaves of maize inbred A619. Proteins were separated by SDS-PAGE in 7.5% gels and then silver-stained (Panel A). An identical gel was Western-blotted and a longitudinal section of each lane was probed with avidin (Panel B). Lanes were 1: crude (10 μg); 2: $(NH_4)_2SO_4$ (10 μg); 3: S-300 (5 μg); 4: Blue Sepharose (2 μg); 5: Mono-Q ACCase II (5 μg); and 6: Mono-Q ACCase I (5 μg). Diagonal lines between lanes indicate position of molecular weight markers shown on the left.

Western blots and silver-stained gels of purification fractions separated by 7.5% SDS-PAGE showed that neither ACCase I nor ACCase II Mono-Q fractions contained biotinylated polypeptides smaller than 212 kD. A polypeptide >212 kD was the primary protein component of the ACCase I Mono-Q fragment (FIG. 5). The ACCase II fraction contained a biotinylated polypeptide >212 kD and a large amount of a 55 kD non-biotinylated polypeptide. Fractions from earlier purification steps contained additional biotinylated proteins of approximately 74, 75, and 125 kD (FIG. 5).

To better compare the biotinylated polypeptides >212 kD in ACCase fractions I and II, we used 6% SDS-PAGE, which showed that the mass of ACCase II was approximately 8 kD less than that of ACCase I. Molecular masses were estimated to be 219 kD (ACCase II) and 227 kD (ACCase I), based on comparisons with polypeptide standards and the observation (N. R. Palosaari, Plant Physiol., 99(S), 359 (1992)) that, on Phastgels (Pharmacia), ACCase I polypeptide was slightly smaller than dodecameric horse spleen ferritin (238 kD; M. Heusterspreute et al., *FEBS Lett.*, 129, 322–327 (1981)). All purification fractions through the Blue Sepharose step contained both ACCase I and II polypeptides. Rapid extraction of leaves in buffer containing five additional protease inhibitors, or a 4 hour incubation of extracts at 25° C., had little or no effect on the relative amounts of the two polypeptides, suggesting that ACCase II is not a breakdown product of ACCase I.

Antiserum to ACCase I strongly recognized the ACCase I polypeptide in crude extracts and showed little or no recognition of ACCase II polypeptides. No bands were recognized by preimmune serum. Assuming that avidin binds similarly to ACCase I and II polypeptides, it appears that the amount of ACCase II on the Western blot was slightly less than the amount of ACCase I. However, the relative staining with antibody compared to avidin indicated that the antibody had significantly less affinity for ACCase II than ACCase I.

To determine whether the same ACCase polypeptides were expressed in different maize cell types, proteins in mesophyll chloroplasts and crude extracts of leaves, endosperm tissue, embryos, and BMS cells were separated by SDS-PAGE. All preparations contained a predominant biotinylated polypeptide of approximately 227 kD (ACCase I) that was strongly recognized by ACCase antiserum or avidin. Similar 227 kD band densities were observed when gel lanes were probed with either avidin or ACCase antiserum. The 219 kD ACCase II polypeptide was readily detected in leaves only by avidin binding, but was in low abundance or not detected in extracts from other tissues. Only the 227 kD ACCase I polypeptide was detected in purified mesophyll chloroplasts, however, suggesting that the 219 kD ACCase II polypeptide is localized elsewhere in mesophyll cells or in other cell types of young leaves. ACCase activity and a >212 kD biotinylated polypeptide(s) were also found in bundle sheath strand extracts, but low yields prevented us from determining the type of ACCase present. Two other major biotinylated polypeptides of 75 and 74 kD were found in all tissues. Other non-biotinylated proteins of 66 kD (faint) and 55 kD were also recognized by ACCase antiserum. The 55 kD polypeptide was only found in leaves; it was also present in both ACCase I and II Mono Q fractions (FIG. 5) and was identified as the Rubisco large subunit based on its comigration with protein immunoprecipitated by spinach Rubisco antiserum.

Figure 6:
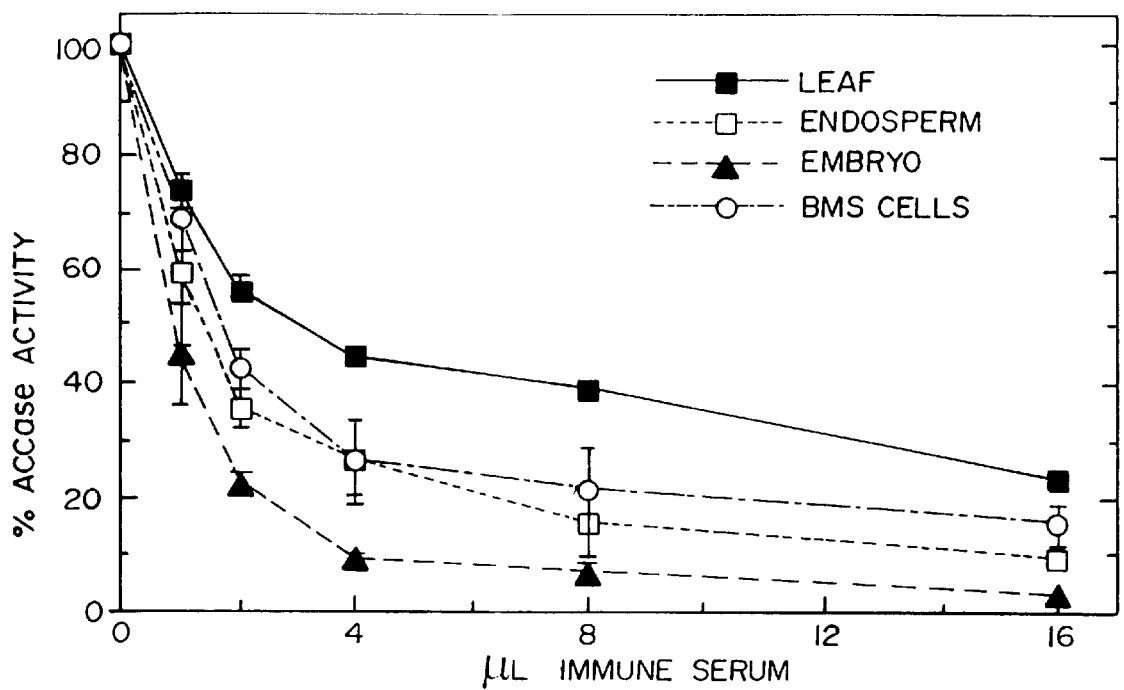
FIG. 6: Immunoprecipitation of ACCase activity from B773 leaf, embryo, endosperm, and BMS suspension cultured cells. Equal activities (0.58 nmol $min^{-1}$) were incubated with 16 IL serum (immune plus preimmune), immune complexes were precipitated with Protein A-agarose, and ACCase activity remaining in the resulting supernatant fraction was measured relative to the preimmune serum control.

ACCase antiserum immunoprecipitated at least 75% of ACCase activity from crude, desalted extracts of leaves, endosperm tissue, embryos, and BMS cells (FIG. 6), indicating that most of the ACCase activity in these tissues is immunologically related to the ACCase I polypeptide of leaves. less activity was precipitated from leaves (75%) than from other tissues, particularly embryos (98%). Compared to immunoprecipitation, inhibition of ACCase activity by antiserum in solution was less than 20% as effective in reducing ACCase activity.

The substrate specificity of ACCase from different purification fractions was examined to compare $[^{14}C]HCO_3^-$ incorporation in the presence of different acyl-CoA substrates. Both ACCase I and II utilized propionyl-Co-A 40 to 50% as rapidly as acetyl-CoA at 50 to 500 $\mu$M substrate even though they contained no biotinylated polypeptides (FIG. 5) the size of known propionyl CoA carboxylases (70 to 75 kD; see E. S. Wurtele et al., Archives of Biochemistry and Biophysics, 278, 179–186 (1990)). Activities in the presence of both acetyl-CoA and propionyl-CoA (250 or 500 $\mu$M each) were approximately 90 (ACCase I) to 130% (ACCase II) that of 500 $\mu$M acetyl-CoA alone. Crude leaf extracts utilized propionyl-CoA and methylcrotonyl-CoA 60% as efficiently as acetyl-CoA. Methylcrotonyl CoA carboxylase activity was reduced 85% by gel filtration and was completely removed by Blue Sepharose affinity chromatography.

Figure 7:
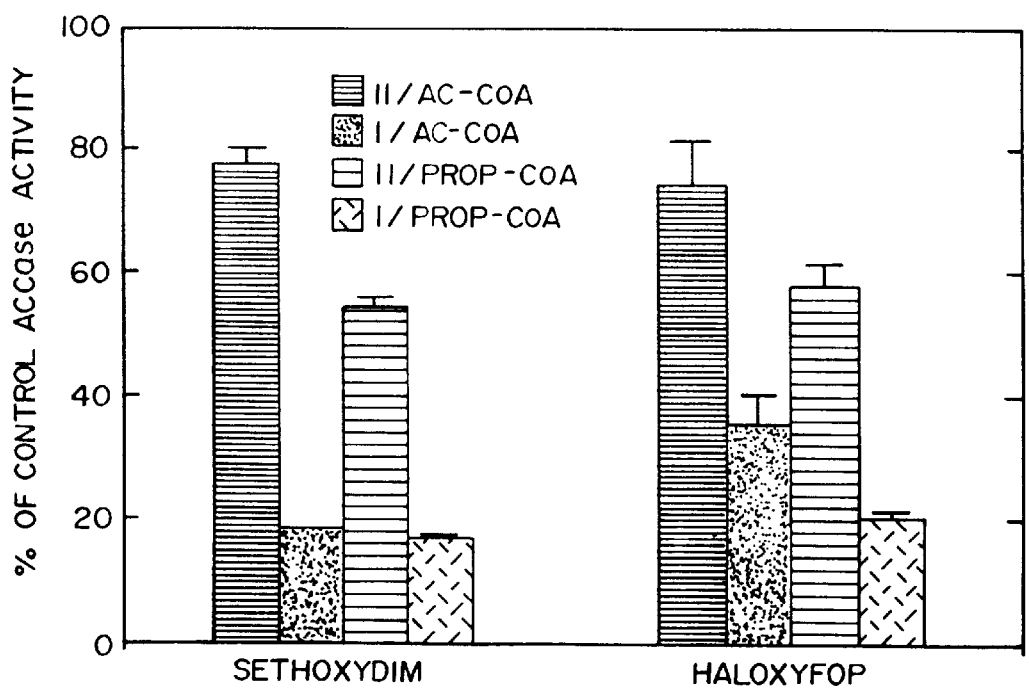
FIG. 7: Herbicide inhibition of acetyl-(AcCoA) or propionyl-CoA (Prop-CoA)-dependent $H^{14}CO_3^-$ incorporation into acid-stable product by ACCase I and II Mono-Q fractions. Activities in the presence of haloxyfop (1 μM) are expressed relative to the minus herbicide control.

ACCase I and II differed significantly in their inhibition by either haloxyfop or sethoxydim (FIG. 7). Acetyl-CoA or propionyl-CoA-dependent $H^{14}CO_3^-$ incorporation by ACCase I was strongly inhibited (65 to 80%) by 1 $\mu$M haloxyfop or 10 $\mu$M sethoxydim, while ACCase II activity was inhibited less than 50% for all herbicide/substrate combinations examined.

C. Cloning and Identification of Maize cDNA Clones Encoding ACCase

Maize cDNA clones encoding a portion of the ACCase game were identified by screening a DNA library generated from maize. The cDNA clones were used to identify the sequence of the ACCase gene and to identify the genomic DNA fragments encoding the gene or genes for ACCase.

A $\lambda$ gt11 cDNA library from maize inbred A188 seedlings was prepared by standard method for oligo-dT priming, as described for pea cDNA. (Gantt and Key, Eur. J. Biochem., 166:119–125 (1987). Plaque lifts of the maize cDNA library were screened with maize ACCase antiserum (Egli et al., Plant Physiol., 101, 499 (1993)) to identify plaques expressing ACCase-like proteins, as described by Sambrook et al., cited supra. (1989). The initial screen of 800,000 plaques yielded 120 positives. Rescreening and plaque purification reduced the number of positives to 14. All 14 clones bound ACCase antibodies that, when eluted from plaque lifts (J. Hammarback et al., J. Biol. Chem., 265:12763 (1990)), recognized a 227-kD biotinylated polypeptide on SDS-PAGE western blots of embryo and leaf crude extracts. The strongest western blot reaction was obtained with cDNA clone #15-14. The six best clones were digested with EcoRI to excise maize cDNA inserts. Total insert sizes ranged from 1.2 to 5.1 kb indicating the clones most likely did not contain the full coding sequences for the mature 219-kD and 227-kD ACCase polypeptides (minimum estimates of 6.1 and 6.3 kb, respectively).

Figure 8:
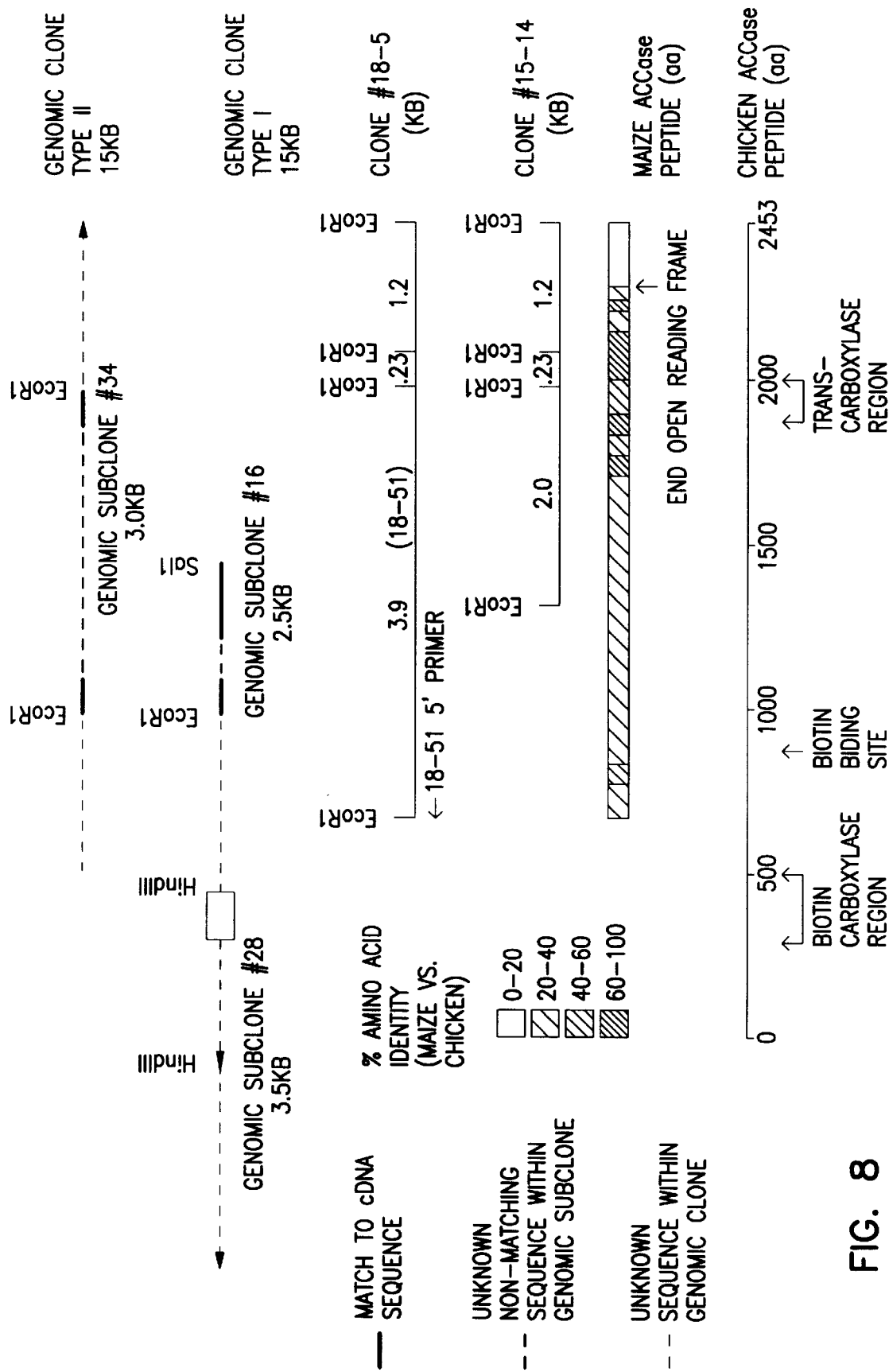
FIG. 8: Comparison of the peptide sequence of maize cDNA clones #15-14 and #18-5 with chicken ACCase. The approximate locations of the biotin carboxylase, biotin binding site, and biotin transcarboxylase functional domains are indicated for the chicken sequence. The percentages of amino acid identity are indicated by cross-hatched boxes for the maize coding sequence. Regions of genomic DNA Type I and Type II clone sequences that align with cDNA #18-5 are indicated by solid heavy lines. The approximate locations of subclone #28 and #16 from genomic Type I and subclone #34 from genomic Type II clones are indicated.

Clone #15-14 contained three EcoRI fragments of 2.0, 1.2 and 0.23 kb shown in FIG. 8. Southern blots showed that the 1.2 and 2.0-kb fragments of clone #15-14 each hybridized to different fragments in the other five clones, with the exception of clone #4-4 which only contained a 1.2-kb fragment. The six maize cDNA clones contained EcoRI fragments that hybridized to a large transcript (ca. 7.8 kb) on Northern blots of total RNA from maize leaves, embryos and endosperm (FIG. 9). BMS cell culture RNA also contained a 7.8 kb transcript, but the hybridization signal is not evident on this exposure (FIG. 9). The relative abundance of the 7.8-kb transcript in embryos was higher than the other sources which is consistent with their ACCase activity.

The three EcoRI fragments were subcloned from cDNA clone #15-14 into BlueScript vector and sequenced by the dideoxy chain termination method (Sequenase 2.0 USB) initially using T3 and T7 primers and then oligonucleotide primers based on insert sequence. A clone #16-6 was also sequenced in a similar manner. Clone #16-6 included three EcoRI fragments of 3.1 kb, 1.2 kb, and 0.23 kb and had additional sequence located upstream from that of clone #15-14. After comparing the sequence and determining that the sequence was the same, the additional 1.2 kb sequence at the 5' end was sequenced.

Clone #18-5 was sequenced in a similar manner. Clone #18-5 included 3.9 kb, 1.2 kb, and 0.23 kb EcoRI fragments and contains an additional 1.9 kb 5' sequence upstream from clone #15-14. Subclone #18-51 (3.9 kb EcoRI fragment) has been deposited with the American Type Culture Collection and given Accession No. 69236.

GenBank, PIR-29, and Swiss-Prot 19 data banks have been searched for amino acid homology with the corresponding amino acid sequences of the three subclones of clone #18-5. Peptide sequences corresponding to the maize cDNA subclones had higher similarity to chicken, rat, and yeast ACCases than to any other peptide sequence in the data banks. FIG. 8 illustrates the relative organization of the 3.9, 1.2 and 0.23-kb EcoRI fragments of clone #18-5 and their co-linearity and extent of amino acid identity with chicken ACCase cDNA sequence. This comparison shows that the maize clone #18-5 has a large region near the 3' end with high amino acid identity (40 to 61%) to chicken ACCase, a longer region with 23% identity in the middle of the 3.9-kb sequence, and a short region with 52% identify near the 5' of the 3.9 kb sequence.

Portions of the sequence of the #18-51 subclone have been identified as encoding domains of the ACCase enzyme of functional significance. Those functional regions include a fragment th at spans the presumed transcarboxylase active site in the enzyme having the following presumed sequence SEQ ID NO: 2:

```
1112-856
GTT CCT GCA AAC ATT GGT GGA CCT CTT CCT ATT ACC AAA
CCT CTG GAC CCT CCA GAC AGA CCT GTT GCT TAC ATC CCT
GAG AAC ACA TGC GAT CCA CGT GCA GCT ATC TGT GGT GTA
GAT GAC AGC CAA GGG AAA TGG TTG GGT GGT ATG TTT GAC
AAA GAC AGC TTT GTG GAG ACA TTT GAA GGA TGG GCA AAA
ACA GTG GTT ACT GGC AGA GCA AAG CTT GGA GGA ATT CCT
GTG GGC GTC ATA GCT GTG GAG ACA
```

This functional domain is contained in the sequence 1112 to 856 base pair from the 3' stop codon or carboxy terminus region of the ACCase coding, sequence of maize. This transcarboxylase active sequence is also present in clone 415-14.

Another functional region that has been identified spans the 12 base pair sequence encoding the biotin binding site having the following peptide sequence SEQ ID NO: 3:

```
5' GTT ATG AAG ATG 3'
    Val Met Lys Met
```

The biotin binding site is encoded approximately 30% in from the 5' (N-terminus) end of rat, chicken and yeast ACCase genes. These functional domains are useful in mapping and further identifying other cDNA and/or genomic fragments encoding ACCase genes.

The cDNA clones encoding portions of the acetyl CoA carboxylase genes are useful to identify the sequence of the gene or genes and are useful as probes to locate the genomic copies of the gene or genes. Because the ACCase antibodies used to screen the λ gt11 library recognize both the 219 and 227 kD ACCase polypeptides, it has not been determined which polypeptide is encoded these less than full length clones. It is likely that the majority of the clones code the 227 kD polypeptide since that polypeptide is more abundant in the f tissue source of the DNA library and the antibodies have a higher affinity for 227 kD ACCase polypeptide.

EXAMPLE VI

Isolation and Sequencing of Genomic Encoded ACCase Genes and a Complete cDNA Sequence of a Maize ACCase Gene The maize genome has been analyzed to identify copy number and location of the genomic copies of ACCase gene or genes. Portions of the genomic copies of the acetyl CoA carboxylase genes from maize have been cloned and sequenced.

A maize genomic lambda library (Clontech, Palo Alto, Calif.) was screened with the 2 kb subclone from #15-14 and several clones of about 15 kb were identified as having homology to the ACCase cDNA. Restriction mapping and partial sequence analysis revealed two types of genomic clones (Type I and Type II) that differed in restriction sites and in their position relative to the ACCase partial cDNA sequence as shown in FIG. 8.

The 2.5 kb EcoRI-SII fragment (#16) from the Type I genomic clone and the 3.0 kb EcoRI-EcoRI fragment (#34) from the Type II genomic clone were shown to hybridize to the 3.9 kb probe from #18-5 and were subcloned into the Bluescript vector and sequenced. Approximately 1.5 kb of DNA sequence from the genomic 1 2.5 kb fragment were 100% identical to coding sequence from the 3.9 kb cDNA subclone #18-51 described in Example V; the remaining sequence exhibited no identity with the cDNA clone and presumably represents noncoding intron sequence. A 350 nucleotide sequence derived from the genomic II 3.0 kb fragment was about 95% identical to the cDNA clone indicating that its coding sequence differs from that of genomic Type 1. These results also indicate that the genome could carry at least two different genes encoding acetyl CoA carboxylase activity.

To identify and clone the remainder of the gene representing the amino-terminus of maize ACCase, additional regions from the Type I genomic clone have been subcloned and partly sequenced. The 3.5 kb HindIII—HindIII fragment (#28) has been sequenced for about 400 nucleotides from each end. The 3' end of #28 shows significant homology to the amino acid sequence from the chicken sequence located about 0.5 kb from the start of the chicken gene. The complete sequence for fragment #28 will be obtained and analyzed to determine whether it contains the 5' end of the ACCase coding region. The start of the transcribed region, and thus the likely start of the coding region for ACCase, can be identified by using the genomic clones in RNAse protection analysis (J. Sambrook ct al., "Molecular Cloning—A Laboratory Manual," Cold Spring Harbor Press, Cold Spring Harbor, N.Y. (1989)). Based on sequence data from the genomic clone, alignment, as shown in FIG. 8, with sequences of other ACCases and identification of potential open reading frames, oligonucleotide primers will be constructed to synthesize cDNA molecules representing the amino terminus of the ACCase gene. These molecules will be hybridized to genomic I DNA fragments such as #28 and the nonhybridizing portions digested with SI nuclease. The end of the protected fragment will be determined by analysis on a DNA sequencing gel.

To synthesize the remaining coding region between the end of the cDNA clone #18-5 and the start of transcription, two oligonucleotide primers were synthesized. Primer 1 is complementary to the DNA sequence: (SEQ ID NO:4)

5' GCCAGATTCC ACCAAAGCAT ATATCC 3' near the 5' end of cDNA subclone #18-51 and can be used as a primer for synthesis of cDNA molecules from maize seedling leaf or embryo RNA. A primer corresponding to a DNA sequence near the transcription start site can be used in combination with primer 1 for the amplification of DNA according to the polymerase chain reaction (PCR) procedure. Several independent clones will be sequenced and their sequences compared to the known sequence of the type I genomic clone to determine the exact coding sequence corresponding to that maize gene for ACCase. A similar strategy may be used to obtain the complete coding sequence for genomic type II ACCase.

The remaining cDNA sequence was obtained by three successive rounds of RT-PCR using oligonucleotide primers based on genomic apparent exon (5') and known cDNA (3') sequences. The primers used to amplify nucleotides 1–240 of the cDNA were 28sst-a5+ (SEQ ID NO. 7) and 28sst-6at3+ (SEQ ID NO:8), nucleotides 217–610 of the cDNA were 28sst-5+ (SEQ ID NO:9) and 28-2t3+ (SEQ ID NO:10), and nucleotides 537-2094 of the cDNA were ACCPCR5' (SEQ ID NO:11) and I55⁻ (SEQ ID NO:4) (Table V). PCR products corresponding to nucleotides 1–240, 217–610, and 537–2094 of the final sequence were cloned into PCR-script (Stratagene).

TABLE V

| cDNA Position | 5' primer designation | 5' primer sequence | 3' primer designation | 3' primer sequence |
|---|---|---|---|---|
| nt-1-240 | 28sst-a5+ | GGTCTTCAATTGTGCTGTCTGG (SEQ ID NO:7) | 28sst-6at3+ | CCTTGACGAACAGACTGGCTGTGC (SEQ ID NO:8) |
| nt 217-610 | 28sst-5+ | CACAGCCAGTCTGTTCGTCAAGG (SEQ ID NO:9) | 28-2t3+ | CCTCTACGTAATTGGTCAGC (SEQ ID NO:10) |
| nt 537-2094 | ACCPCR5' | CATAGCTATGGCAACTCCGG (SEQ ID NO:11) | I55⁻ | GGATATATGCTTTGGTGGAATCTGGC (SEQ ID NO:4) |

The original 5.4-kb cDNA clone #18-5 and PCR products from at least three individual PCR per oligonucleotide pair were sequenced in both directions by the dideoxy chain-termination method, using either Sequenase II (U.S. Biochemicals) or ABI 373 (Applied Biosystems, Inc.) protocols. No sequence differences were found in regions of clone overlaps. The complete sequence of the cDNA of maize ACCase (nucleotides 1–7470 SEQ ID NO:5) and its corresponding amino acid sequence (amino acids 1–2325 SEQ ID NO:6) are shown in FIGS. 13 and 14. The 7470 bp cDNA includes a 459 nucleotide 3' untranslated region and 36 nucleotides of 5' untranslated sequences.

The first Met codon in the cDNA (nucleotides 37–39) was identified as the start codon based on its similarity to consensus initiation sequences (Kozak, J. Cell. Biol., 108, 229 (1989); Lutcke et al., Embo. J., 6, 43 (1987)). An in-frame stop was found in the genomic sequence 6 nucleotides upstream of the sequenced cDNA, and RT-PCR analysis of this region suggested that the in frame stop codon was also present in the cDNA. The 3' end of the coding sequence was defined by two stop codons present in the large open reading frame after nucleotide 7011. The translated coding sequence predicted a polypeptide of 2325 amino acids (257 kD; SEQ ID NO:6) which was 79 to 81% identical to multifunctional (MF) ACCase from alfalfa (Shorrosh et al., Proc. Nat'l. Acad. Sci., 91, 4323 (1994)), wheat (Gornicki et al., Proc. Nat'l Acad. Sci., 91, 6860 (1994)), and to a 118-amino acid predicted polypeptide of a rice expressed sequence tag (Genbank accession # D39099, T. Sasaki), but only 53 to 55% identical to ACCase from other eukaryotes. In a pileup alignment of plant ACCases (Genetics Computer Group, Madison, Wis.), Met 1 of both maize and Brassica naplis ACCases was located about 130 amino acids upstream of the conserved sequence VDEFCKALGG, compared to only 25 amino acids upstream for other plant ACCases. The predicted 2325 amino acids of maize ACCase contains a biotinylation site at position 806, within the conserved MKM motif (Ton et al., Eur. J. Biochem., 215, 687 (1993)). The arrangement and amino acid sequence of binding sites (Shorrosh et al., Proc. Nat'l. Acad. Sci., 91, 4323 (1994)) for ATP (amino acids 318–333), biotin (amino acids 799–811; biotin at 806), acetyl-CoA (amino acids 1952–1961), and carboxybiotin (amino acids 1662–1711) were highly conserved among all MF ACCases.

The initial restriction fragment length polymorphism (RFLP) analysis of EcoRI-digested total DNA from three maize inbred lines showed one band when probed with the 2 kb subclone from #15-14 (internal to gene) and two bands when probed with the 1.2 kb subclone (near the 3' end of the gene). Fragments homologous to the 2 kb probe were monomorphic and the more intense of the two bands hybridizing with the 1.2 kb probe was dimorphic. As discussed in Example V, these results support the view that maize contains at least two distinguishable ACCase genes and that they may be quite similar for much of the coding region. Additional genomic Southern blots of a set of recombinant inbred lines were used to map polymorphisms for the ACCase probes to maize chromosomes. One polymorphism was mapped to the short arm of chromosome 2; other polymorphisms were not evident in these initial tests to identify a chromosomal location for other maize ACCase genes. The chromosomal location of different ACCase genes will be verified by additional RFLP mapping in recombinant inbreds using gene-specific probes obtained from Type I and Type II genomic clones. The copy number for each locus will be determined by Southern blot restriction comparisons or quantitation on DNA slot blots. A probe derived from nucleotides 3400-5932 hybridized to a single 8.3 kilobase mRNA in a Northern blot.

EXAMPLE VII

Expression of the Maize ACCase Chloroplast Transit Peptide

Several characteristics of a chloroplast transit peptide were noted within the first approximately 73 amino acids of the predicted N-terminal sequence of maize ACCase. The CTP cleavage site motif is not found in maize in the putative maize ACCase CTP, however, only about 30% of known CTFPs contain this consensus sequence (Gavel and von Hejne, FEBS Lett., 261, 455 (1990)). The maize ACCase N-terminus instead appears to have several of the properties typical of known CTPs: (1) a lack of acidic residues in amino acids 1–10, (2) high Ser+Thr content (69% within amino acids 23–35), and (3) a predicted turn →4B sheet within amino acids 58–73 (von Hejne and Nishikawa, FEBS Lett., 278, 1 (1991)).

The ability of the amino acid sequence contained within the N-terminal 100 amino acids of the translated maize acetyl-CoA carboxylase (ACCase) cDNA to direct the N-terminal portion of the maize ACCase biotin carboxylase domain into chloroplasts will be tested in vitro by methods used extensively in the literature (see Cline et al., J. Biol. Chem., 260, 3691 (1985); Lubben and Keegstra, Proc. Nat'l. Acad. Sci., 83, 5502 (1986)). The criteria for import will be that (1) an in vitro-synthesized, $^{35}$S-labelled protein is imported into chloroplasts and (2) the transported protein is smaller than the original translation product, by an amount which corresponds to the removal of the expected CTP. Import studies will utilize either maize or pea chloroplasts, as maize chloroplasts are relatively fragile and pea chloroplasts are reported to correctly import proteins from many different species, including maize (Nieto-Sotelo et al., Plant Physiol., 93, 1321 (1990)). Alternatively, the function of the putative maize ACCase CTP will be tested by inserting the first 258 coding nucleotide of maize ACCase in frame with and 5' of a GUS reporter gene in pBI221 (Clontech). This construct and the pBAR plasmid will be used to co-transform maize "Black Mexican Sweet" suspension cells by particle bombardment. Basta-resistant transformants will be selected, and GUS activity and/or protein will be assayed in surviving cultures or in plasmids isolated from transformants.

A partial ACCase construct consisting of nucleotides 1–833 of SEQ ID NO: 5 including the putative CTP (nucleotides 37 to 256) and the first domain within the biotin carboxylase region (identified by amino acid sequence comparison with *E. coli* biotin carboxylase; see Waldrop et al., *Biochem.*, 33, 6249 (1994)) was amplified by PCR and cloned into the EcoRV site of PCR-script (Stratagene) to create the plasmid pBCN1. pBCN1 was transformed into *E. coli* SURE cells (Stratagene). Restriction analysis with BamH1 and HindIII indicated that the 5' end of the ACCase was located adjacent to the T 7 RNA polymerase binding site in PCR-Script. A partial sequence of pBCN1 obtained by using the T7 sequencing primer and the ABI373 automated sequencing protocol confirmed this orientation and showed that the pBCN1 insert sequence was identical to maize ACCase cDNA for at least the first 300 nucleotides and that it included the maize ACCase Met 1 ATG.

Negative controls analogous to pBCN1 but producing peptides beginning at amino acid 83 (Val→Met mutation introduced by PCR at amino acid 83) or at amino acid 101 (Met) of maize ACCase will be constructed. An acyl carrier protein clone containing a CTP (spinach ACPII, a gift of Dr. John Ohlrogge, Michigan State University) will be used as a positive control. These constructs can be used for in vitro transcription, translation, chloroplast import, and SDS-PAGE analysis of products in the same manner as pBCN1.

Purified pBCN1 was digested with EcoRI to linearize the plasmid at the 3' end of the BCN1 insert, electrophoresed in 1.5% agarose, and the plasmid band at approximately 3.8 kb was excised and Gene-Cleaned (BioLab 101). The purified band was digested with 20 ug proteinase K to remove any residual RNAse, extracted with phenol and then chloroform under RNAse-free conditions. DNA content was estimated by ethidium bromide fluorescence in droplets, relative to λ DNA standards (Sambrook et al., *Molecular Cloning: A Laboratory Manual*, 2nd ed. (1989). One ug of pBCN1 DNA was translated into capped RNA with the T7/mMessage mMachine kit (Ambion). RNA yield was estimated by determining the % incorporation of a $^{32}$P-ATP (Amersham) into a precipitable product, according to the Ambion kit instructions. Electrophoresis and autoradiography of $^{32}$P-labelled product showed that it contained a single RNA band of approximately 895 nucleotides, as expected.

The T7-driven RNA transcripts from pBCN1 were translated into $^{35}$S-labelled polypeptides with Ambion's wheat germ IVT kit and approximately 45 µCi $^{35}$S-methionine (Amersham; 37 TBq/mmol) in a 50-µl reaction. An additional RNA, Xenopus elongation factor 1 (Xen ef-1; Ambion), which lacks a transit peptide, was also translated. Labelled proteins were held on ice 6 hours prior to their use in chloroplast import experiments.

Pea (cv. "Little Marvel") and maize (inbred A188) plants were grown in a growth chamber at 25° C., 16 hour day length. Chloroplasts were isolated from pea and maize at 17 and 7 days after planting, respectively, as previously described (Burton et al., *Pestic Biochem. and Physiol.*, 34, 76 (1989); Egli et al., Plant Physiol., 101, 499 (1993)). Intact chloroplasts were washed in resuspension buffer [50 mM HEPES-KOH, pH 7.8 plus 0.33 M (pea) or 0.66M (maize) sorbitol] in preparation for import assays. Suspensions were diluted to obtain 75 µg chlorophyll/0.3 ml (Arnon, *Plant Physiol.*, 24, 1 (1949)).

Import experiments were carried out essentially as described by Cline et al.(*J. Biol. Chem.*, 260, 3691 (1985)). Import reactions containing 0.3 ml pea chloroplast suspension, 40 µl $^{35}$S-translation mixture, 3 mM Mg-ATP and 10 mM Met were incubated under light for 30 minutes at 25° C. Unimported proteins were digested for 30 minutes with 40 µg of thermolysin, and proteolysis was stopped with 10 mM EDTA.

Chloroplasts were re-isolated by centrifuging them through 1-ml 40% v/v Percoll gradients in the presence of resuspension buffer plus 3 mM Mg-ATP, 10 mM Met, and 10 mM EDTA, washed twice in the same buffer, and resuspended in 65 µl of 1 mM MgCl$_2$/10 mM Tris buffer, pH 8.0. Chloroplasts were lysed by three cycles of freeze-thawing in liquid N$_2$, microfuged, and aliquots of the supernatants and of the original in vitro-translated proteins were analyzed by SDS-PAGE in 4–15% gradient Phast gels (Pharmacia), followed by direct detection of radiolabelled proteins in the wet gels (AMBIS).

In vitro translation of BCN1 and Xen-ef1 RNAs yielded $^{35}$S-polypeptides of approximately 30 and 50 kD, respectively. A second $^{35}$S-labelled labelled protein of about 23 kD was also present in the BCN1 translation. No $^{35}$S-labelled protein from the Xen-ef1 translation was imported into pea chloroplasts. In contrast, pea chloroplasts contained a $^{35}$S-polypeptide that was slightly smaller than the major BCN1 translation product, which may represent the mature (cleaved) BCN1 polypeptide. Similar results were seen when maize chloroplasts were analyzed with BCN1 and Xen-ef1 in vitro translation products. Therefore, nucleotides 1–833 of the maize ACCase gene encode a CTP.

EXAMPLE VIII

Expression of a cDNA Clone or Genomic Clones Encoding the ACCase Gene

The cDNA and genomic clones encoding all or a portion of the ACCase gene can be subcloned into a known expression system and the gene products reactive with the antibodies specific for maize ACCase can be identified using a Western blot. The gene products can also be further characterized structurally and/or enzymatically. This will ensure that the genomic and cDNA clones that encode acetyl CoA carboxylase can be screened for promoters that provide for overproduction of the native or herbicide tolerant ACCase enzyme in plants.

For example, the 2 kb EcoRI fragment from clone #15-14 can be subcloned into a plant transformation plasmid pBI121 or pBI221 downstream from the 35S CaMV promoter and upstream from the nopaline 3' polyadenylation signal sequence, as described in Jefferson, *Plant Molec. Biol. Reptr.*, 5, 387–405 (1987). This plasmid can then be used to transform plant cells such as tobacco, Brassica and Arabidopsis cells using protoplast or biolistic transformation, as described by W. J. Gordon-Kamm et al., *Plant Cell*, 2, 603–618 (1990); M. E. Fromm et al., *Bio/Technology*, 8, 833–839 (1990); An, *Methods in Enzymology*, 153, 292 (1987); and D'Elafluin, *The Plant Cell*, 4, 1495 (1992). An increase in transient expression can be detected using quantitative Western blotting with antibodies specific for the ACCase enzymes. Polyclonal antibodies to maize ACCase most likely do not substantially crossreact with ACCase from dicots like tobacco or Arabidopsis.

Alternatively, the ACCase gene can be subcloned along with the 35S CaMV promoter into a binary Ti vector pGA482, as described in An, cited supra., which is a binary Ti vector system and can be used to transform plant cells via Agrobacterium. Stable transformed plants can be generated by standard methods as described in Example III, and levels of expression of ACCase genes can be determined by quantitative Western blots, as described in Harlow and Lane, *Antibodies*, Cold Spring Harbor Laboratories (1988). The ability to monitor expression of cloned ACCase genes will allow for the identification of promoters that provide for an enhanced expression of the ACCase gene. The expression system can be used to screen for those promoters that enhance gene expression of the ACCase gene at least about 5 to 10-fold over the endogenous levels of ACCase produced normally in the plant cells. Because the 35S CaMV promoter is known as a strong promoter, it is likely this promoter will provide for at least a 5-fold increase in the expression of ACCase over that normally produced in the plant cell.

In addition, this expression system can be used to screen antisense DNA sequences. For example, an antisense sequence can be obtained that is complementary to an about 0.5 kb region of the maize ACCase cDNA that has high homology with a portion of the chicken ACCase gene and contains the sequence for the presumed transcarboxylase active site domain, as shown in FIG. 8. The antisense sequence could be subcloned into a pBI121 or pBI221 expression under the control of an inducible plant promoter, such as nitrite reductase promoter (Back et al., *Plant Molec. Biol.*, 17:9–18 (1991)). The ability of the antisense sequence to inhibit expression of the native ACCase gene can be evaluated in transformed cells, for example as described in Hamilton et al., *Nature*, 346:284–287 (1990).

EXAMPLE IX

Identification and Cloning of the Gene From Herbicide Resistant Maize Cell Lines Herbicide resistant maize cell lines were generated as described in Examples I, II, and IV. These herbicide resistant cell lines have been shown to produce an ACCase enzyme that is less sensitive to inhibition by sethoxydim or haloxyfop. The genes encoding the herbicide resistant forms of the ACCase will be identified and cloned using standard methods as described in Sambrook et al., *Guide to Molecular Cloning: A Laboratory Manual* (1989). The genes encoding the herbicide resistant forms of ACCase can then be introduced into herbicide sensitive plant species by standard methods to confer herbicide resistance. For example, the ACCase enzyme in the maize cell line 2167-9/2160-154 S-1 is at least 100-fold less sensitive to sethoxydim than the wild-type.

DNA from the cell line or plants will be obtained and digested with EcoRI and/or other appropriate restriction enzymes, according to standard methods. The restriction enzyme digest will be separated out by agarose gel electrophoresis and probed with either the 2 kb or the 3.9 kb cDNA ACCase probe described in Example V. Fragments hybridizing to the 2 kb or 3.9 kb probe will be subcloned into a Bluescript vector and portions of the gene will be sequenced, as described in Example V, to verify that the entire ACCase gene has been isolated. To confirm that the clone encodes the ACCase gene, it will be subcloned into the pBI121 or pBI221 expression vector, as described in Example VIII. The ACCase gene product expressed by the clone in either Black Mexican sweet corn cells or tobacco cells will be evaluated for reactivity with ACCase specific antibodies, enzyme activity, and/or resistance of the enzyme activity to inhibition with sethoxydim and/or haloxyfop. It is likely that the cloned gene encodes an ACCase which is resistant to inhibition by sethoxydim and haloxyfop. This gene can then be introduced into an herbicide-sensitive embryogenic plant cell or an embryo, including maize cells or immature embryos, to confer herbicide resistance to that plant species.

The complete coding sequence encoding the herbicide resistant form of the ACCase enzyme will be cloned into a plant transformation vector such as pBI121 or pBI221 as described in Jefferson, *Plant Molec. Biol. Reporter*, 5:387–405 (1987). This vector contains the 35S CaMV constitutive promoter, the β-glucuronidase structural gene, and the nopaline synthase 3' polyadenylation signals. The β-glucuronidase gene is replaced with a cloned ACCase gene. Optionally, the cloned ACCase gene can be combined with natural or synthetically produced chloroplast transit peptide sequence from pea, as described in Keegstra & Olsen, *Ann. Rev. Plant. Physiol./Mol. Biol.*, 40:471–501 (1989) and/or unique restriction sites so the cloned gene can be distinguished from the endogenous maize ACCase gene. Standard methods of subcloning will be utilized as described in Sambrook et al., cited supra.

For transformation of maize cells, type II calli can be transformed using biolistic transformation, as described by W. J. Gordon-Kamm et al., *Plant Cell*, 2, 603–618 (1980); M. E. Fromm et al., *Bio/Technology*, , 833–839 (1990); and D. A. Walters et al., *Plant Molecular Biology*, 18, 189–200 (1992). Alternatively, type I embryogenic calli can be transformed using electroporation after mechanically or enzymatically wounding calli, as described by D'Hafluin et al., *The Plant Cell*, 4:1495 (1992). Once the cloned gene is introduced in these calli and transformants are selected, typically by antibiotic resistance, fertile transgenic maize plants can be regenerated, as described by D'Hafluin et al. cited supra. Fertile transgenic plants can be evaluated for herbicide tolerance, as described in Example III. It is likely that the fertile transgenic plants having and expressing a cloned ACCase gene as an ACCase resistant to sethoxydim and/or haloxyfop will exhibit herbicide tolerance.

EXAMPLE X

Generation of Transgenic Plants Having an Increase in Oil Content

Once identified and cloned, the gene or genes from maize acetyl CoA carboxylase can be introduced into plant species, including maize, with a promoter that provides for overexpression of the ACCase enzyme. The overexpression of the ACCase enzyme is likely to lead to an increase in the oil content of the plants and seeds.

Naturally occurring soybeans that have a high oil content and soybeans that have a low oil content have been identified. The acetyl CoA carboxylase from both types of soybeans was isolated, as described in Example V. The activity of the enzyme was measured as a function of the time of seed development and the results are shown in FIG. 11.

Figure 11:
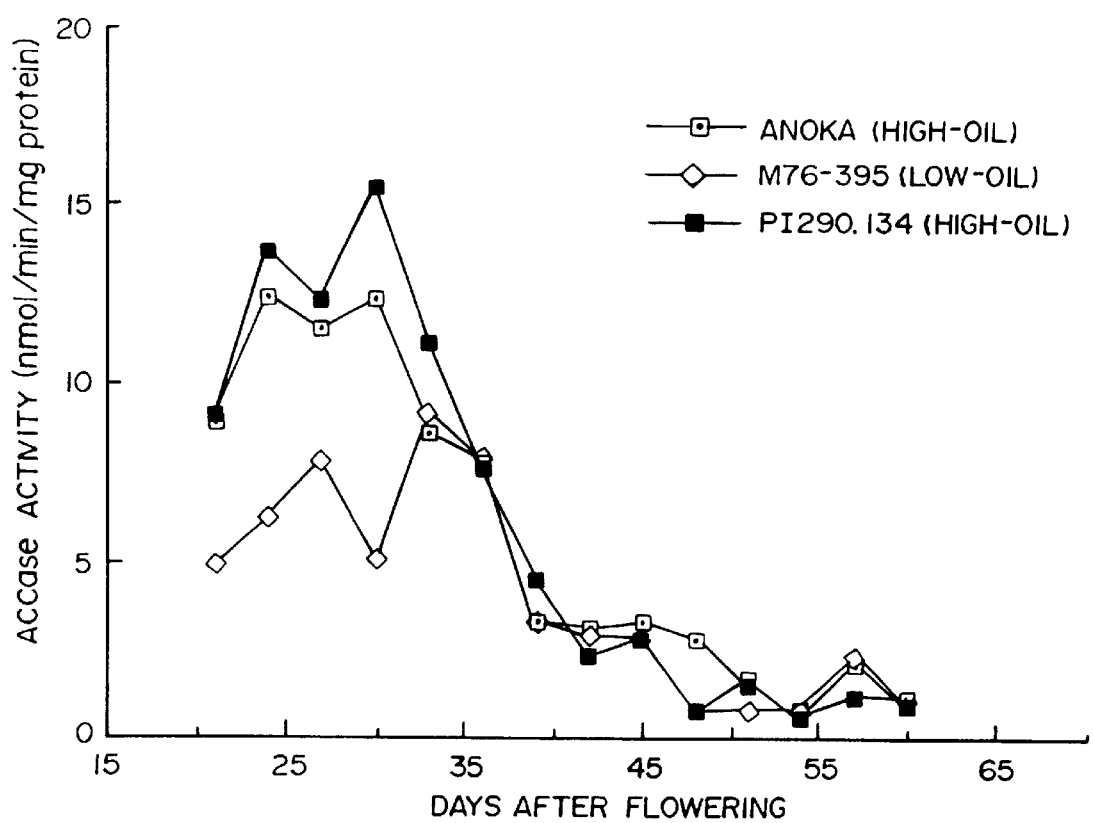
FIG. 11: Graph of ACCase activity during seed development in two high oil soybean cell lines and one low oil soybean cell line.
Figure 12:
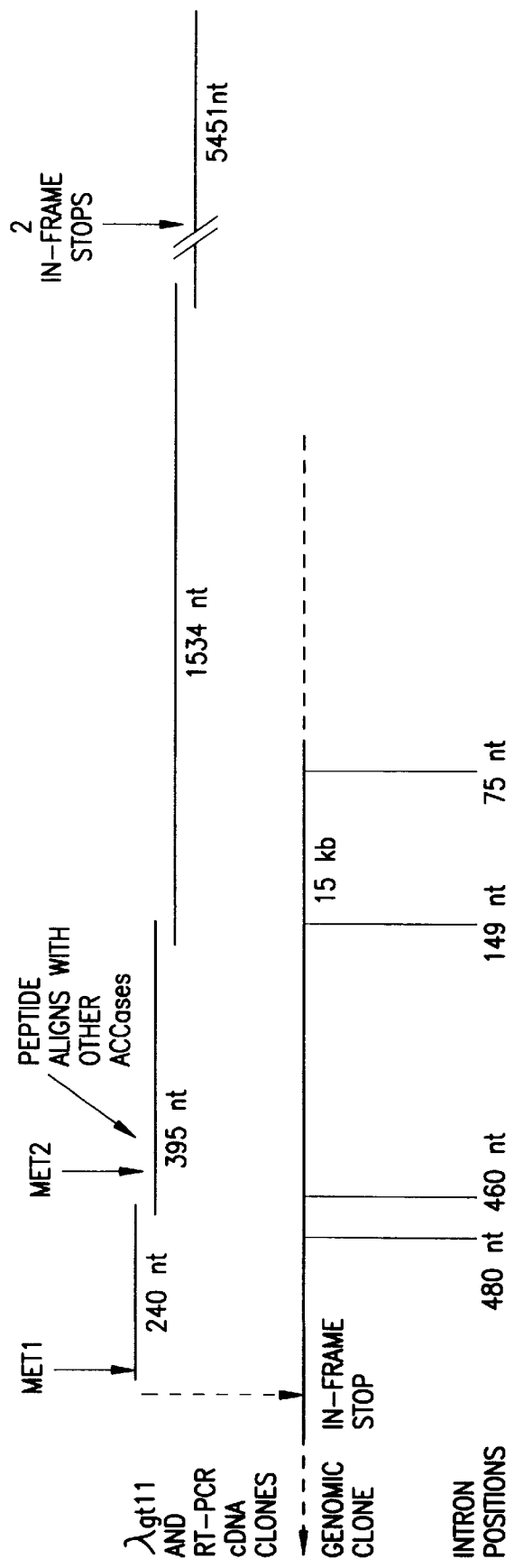
FIG. 12: Cloning strategy to obtain the complete coding sequence of the maize ACCase gene.

The results in the FIG. 11 indicate that higher oil content soybean is associated with a 2-fold increase in the ACCase activity during early to mid stages of development when compared with a low oil content soybean. Thus, increased expression of the ACCase gene correlates with an increase in the oil content of the seed. Total oil content of the seed was also measured at maturity (60 days). The high oil producing cell lines, Anoka and PI28C.134, have a total oil content of 21.8% and 19.9%, respectively. In contrast, the low oil soybean line of M76-395, has an oil content of 13.6% oil. Thus, the increase of ACCase expression early in seed development correlates with a higher total oil content in the seed at maturity.

A gene encoding a genomic maize acetyl CoA carboxylase can be isolated, as described in Example V, and used to transform plant species by protoplast or biolistic transformation. If the gene is combined with a strong promoter, such as the 35S cauliflower mosaic virus promoter, overexpression of the ACCase gene is likely. Alternatively, selecting transformed cells with multiple copies of the gene can also result in transformed cells overexpressing the ACCase gene. The gene can be cloned into a vector such as pBI121 or pBI221, as described by Jefferson, cited supra. This vector contains the 35S cauliflower mosaic virus promoter, the β-glucuronidase structural gene, and the nopaline synthase 3' polyadenylation signals. The cloned ACCase gene can replace the β-glucuronidase gene and then be used to transform plant cells, including maize, as described in Example VIII.

Transformed cells can be screened for overproduction of ACCase. The presence of the cloned gene can be verified by identifying the unique restriction enzyme sites incorporated into the cloned gene. ACCase levels can be assessed by standard enzyme assay methods and quantitative Western blots using antibodies specific for maize ACCase. Fatty acid and lipid content in cells lines overproducing ACCase are likely to be elevated and can be assessed using standard methodologies, as described in Clark & Snyder, *JACS*, 66:1316 (1989). Transformed cell lines exhibiting overproduction of ACCase and an increase in total oil content will be used to regenerate fertile transgenic plants and seeds, as described in D'Hafluin, cited supra.

While the present invention has been described in connection with the preferred embodiment thereof, it will be understood many modifications will be readily apparent to those skilled in the art, and this application is intended to cover any adaptations or variations thereof. It is manifestly intended this invention be limited only by the claims and equivalents thereof.

All patents and publications described herein are hereby incorporated by reference.

What is claimed is:

1. An isolated and purified DNA molecule comprising a DNA segment encoding a maize acetyl CoA carboxylase comprising an amino terminal chloroplast transit peptide.

2. An isolated and purified DNA molecule comprising SEQ ID NO:1 or SEQ ID NO:5.

3. The DNA molecule of claim 1 which encodes a maize acetyl CoA carboxylase comprising SEQ ID NO:6.

4. An isolated and purified DNA molecule which is complementary to SEQ ID NO:1 or SEQ ID NO:5.

5. A method of expressing a maize acetyl CoA carboxylase gene in a host cell comprising:

(a) introducing into a host cell in vitro an expression cassette comprising a DNA molecule encoding a maize acetyl CoA carboxylase comprising an amino terminal chloroplast transit peptide, wherein said DNA molecule is operably linked to a promoter functional in the host cell, so as to yield a transformed host cell; and (b) identifying a transformed host cell which expresses the DNA molecule.

6. The method according to claim 5, wherein the host cell is a plant cell.

7. The method according to claim 5, wherein the host cell is selected from the group consisting of an insect cell, a prokaryotic cell, a diatom, a yeast cell and an algal cell.

8. The method of claim 5 wherein the DNA molecule comprises SEQ ID NO:5.

9. The method according to claim 6, which further comprises regenerating a differentiated plant from the transformed host cell.

10. The method according to claim 9, wherein the differentiated plant is a monocot.

11. The method according to claim 9, wherein the differentiated plant is a dicot.

\* \* \* \* \*

UNITED STATES PATENT AND TRADEMARK OFFICE
CERTIFICATE OF CORRECTION

PATENT NO.: 6,069,298
DATED: May 30, 2000
INVENTOR(S): Gengenbach et al.

It is certified that errors appear in the above-identified patent and that said Patent is hereby corrected as shown below:

In the title delete "AND AN ALTERATION IN OIL CONTENT OF PLANTS".

Signed and Sealed this

First Day of May, 2001

*Attest:*

NICHOLAS P. GODICI

*Attesting Officer*   *Acting Director of the United States Patent and Trademark Office*